(12) United States Patent
Ni et al.

(10) Patent No.: US 7,041,803 B2
(45) Date of Patent: May 9, 2006

(54) GALECTIN 11

(75) Inventors: Jian Ni, Germantown, MD (US); Reiner L. Gentz, Belo Horizonte-Mg (BR); Craig A. Rosen, Laytonsville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 146 days.

(21) Appl. No.: 10/455,366

(22) Filed: Jun. 6, 2003

(65) Prior Publication Data

US 2003/0208044 A1 Nov. 6, 2003

Related U.S. Application Data

(60) Division of application No. 09/557,170, filed on Apr. 21, 2000, now Pat. No. 6,605,699, which is a continuation-in-part of application No. 09/109,864, filed on Jul. 6, 1998, now abandoned, which is a continuation-in-part of application No. 09/010,146, filed on Jan. 21, 1998, now abandoned.

(60) Provisional application No. 60/169,932, filed on Dec. 10, 1999, provisional application No. 60/130,390, filed on Apr. 21, 1999, provisional application No. 60/034,204, filed on Jan. 21, 1997, provisional application No. 60/034,205, filed on Jan. 21, 1997.

(51) Int. Cl.
*C07K 16/00* (2006.01)
*C07K 16/28* (2006.01)

(52) U.S. Cl. .............................. 530/387.1; 530/389.2; 530/388.24; 530/391.1

(58) Field of Classification Search ........... 530/388.28, 530/387.1, 388.24, 389.2, 391.1; 435/326

See application file for complete search history.

(56) References Cited

U.S. PATENT DOCUMENTS 5,011,912 A 4/1991 Hopp et al.
6,168,920 B1 1/2001 Hillman et al.

FOREIGN PATENT DOCUMENTS

| DE | 196 49 207 | 2/1998 |
|---|---|---|
| JP | 11-46765 | 2/1999 |
| WO | WO-97/33993 | 9/1997 |
| WO | WO-98/17687 | 4/1998 |
| WO | WO-98/31799 | 7/1998 |
| WO | WO-98/50546 | 11/1998 |
| WO | WO-98/51706 | 11/1998 |
| WO | WO-98/55508 | 12/1998 |
| WO | WO-00/01728 | 1/2000 |
| WO | WO-00/09690 | 2/2000 |
| WO | WO-00/23572 | 4/2000 |
| WO | WO-00/63221 | 10/2000 |

OTHER PUBLICATIONS

Lederman S, et al. A single amino acid substitution in a common African allele of the CD4 molecule ablates binding of the monoclonal antibody, OKT4. Mol Immunol. 28(11): 1171-81, 1991.*
Li CH, Yamashiro D, Tseng LF, Chang WC, Ferrara P. beta-Endorphin omission analogs: dissociation of immunoreactivity from other biological activities. Proc Natl Acad Sci U S A. 77(6):3211-3214, 1980.*
Colman PM. Effects of amino acid sequence changes on antibody-antigen interactions. Res Immunol. 145(1):33-36, 1994.*
Adams, et al., "Complementary DNA sequencing: expressed sequence tags and human genome project," *Science*, 252 (5013):1651-1656 (1991).
Adams, et al., "Initial assessment of human gene diversity and expression patterns based upon 83 million nucleotides of cDNA sequence," *Nature*, 377(6547 Suppl):3-174 (Sep. 28, 1995).
Attwood, *Science*, 290:471-473 (2000).
Barondes, et al., "Galectins: a family of animal beta-galactoside-binding lectins," *Cell*, 76:597-598 (1994).
Bendayan, *J. Histochem. Cytochem.*, 43:881-886 (1995).
Bost, et al., *Immunol. Invest.*, 17:577-586 (1988).
Cai, et al., "An effective method for coupling single-mode fiber to thin-film waveguide," *J. of Lightwave Tech.*, 5:577-583 (1991).
Crocker, et al., "Sialoadhesin, a macrophage sialic acid binding receptor for haemopoietic cells with 17 immunoglobulin-like domains," *EMBO J.*, 13(19):4490-4503 (1994).
Genbank Accession No. T48852, Hillier, et al. (Feb. 8, 1995).
Eugchi, *Intern. Med.*, 40:275-284 (2001).
Genbank Accession No. G14442, Myers, et al. (Jan. 4, 1996).
Genbank Accession No. U71382, Patel, et al. (Nov. 12, 1996).
Genbank Accession No. AA344713, Adams, et al. (Apr. 21, 1997).

(Continued)

*Primary Examiner*—Christina Chan
*Assistant Examiner*—Maher Haddad
(74) *Attorney, Agent, or Firm*—Human Genome Sciences, Inc.

(57) ABSTRACT

The present invention relates to novel galectin 11 proteins which are members of the galectin superfamily. In particular, isolated nucleic acid molecules are provided encoding the human galectin 11 proteins. Galectin 11 polypeptides are also provided as are vectors, host cells and recombinant methods for producing the same. The invention further relates to screening methods for identifying agonists and antagonists of galectin 11 activity. Also provided are diagnostic and therapeutic methods.

49 Claims, 10 Drawing Sheets

OTHER PUBLICATIONS

Genbank Accession No. G22008, Hudson, et al. (May 31, 1996).
Genbank Accession No. B05004, Evans, et al. (Jun. 26, 1996).
Genbank Accession No. R59292, Hillier, et al. (May 24, 1995).
Genbank Accession No. AA33451, Adams, et al. (Apr. 21, 1997).
Genbank Accession No. AA31108, Adams, et al. (Apr. 19, 1997).
Genbank Accession No. H30148, Hillier, et al. (Aug. 16, 1995).
Genbank Accession No. R59291, Hillier, et al. (May 24, 1995).
Genbank Accession No. H27468, Hillier, et al. (Aug. 16, 1995).
Genbank Accession No. AA349100, Hillier, et al. (Apr. 21, 1997).
Genbank Accession No. AA020729, Hillier, et al. (Jan. 30, 1997).
Genbank Accession No. AA001029, Hillier, et al. (Nov. 29, 1996).
Genbank Accession No. AF222695, Yang, et al. (Feb. 16, 2000).
Genbank Accession No. AF222694, Yang, et al. (Feb. 16, 2000).
Genbank Accession No. U73641, Evans, et al. (Jul. 25, 1997).
Genbank Accession No. AW075917, National Cancer Institute, et al. (Oct. 13, 1999).
Genbank Accession No. H50946, Hillier, et al. (Sep. 18, 1995).
Gitt, et al., "Sequence and mapping of galectin-5, a beta-galectosidase-binding lectin, found in rat erythrocytes," *Journal of Biological Chem.*, 270(10):5032-5038 (1995).
Hiller, et al., "Generation and analysis of 280,000 human expressed sequence tags," *Genome Res.*, 6(9):807-828 (1996) abstract only.
Hotta, et al., "Galectin-12, an adipose-expressed Galectin-like molecule possessing apoptosis-inducing activity," *J. Biol. Chem.*, 276(36):34089-34097 (Sep. 7, 2001).
Kelm, et al., "The Sialoadhesins: a family of sialic acid-dependent cellular recognition molecules within the immunoglobulin superfamily," *Glycoconj. J.*, 13(6):913-926 (1996).
Levi, et al., "Prevention and therapy with electrolectin of experimental autoimmune myasthenia gravis in rabbits," *Eur. J. Immunol.*, 13:500-507 (1983).
Meikratz, et al., "Apoptosis and the cell cycle," *J. of Cell. Biochem.*, 58:160-174 (1995).
Metzler, et al., *Nature Structural Biol.*, 4:527-531 (1997).
Mountz, et al., *Curr. Rheumatol. Rep.*, 3:70-78 (2001).
Offner, et al., "Recombinant human beta-galactoside binding tectin suppresses clinical and histological signs of experimental autoimmune encephalomyelitis," *J. Neuroimmunology*, 28:177-184 (1990).
Perillo, et al., "Apoptosis of T cells mediated by galectin-1," *Nature*, 378:736-739 (1995).
Rose, et al., *Brit. J. Rheumatol.*, 36:158-163 (1997).
Simmons, et al., "Isolation of a cDNA encoding CD33, a differentiation antigen of myeloid progenitor cells," *J. Immunology*, 141(8):2797-2800 (1988).
Skolnick, et al., *Trends in Biotech.*, 18(1):34-39 (2000).
Su, et al., "Surface-epitope masking and expression cloning identifies the human prostate carcinoma tumor antigen gene PCTA-1 a member of the galectin gene family," *PNAS*, 93:7252-7257 (1996).
Takei, et al., "Molecular cloning of a novel gene similar to myeloid antigen DC33 and its specific expression in placenta," *Cytogenet. Cell Genet.*, 78:295-300 (1997).
Yang, et al., "Cell cycle regulation by Galectin-12, a new member of the Galectin superfamily," *J. Biol. Chem.*, 276 (23):20252-20260 (Jun. 8, 2001).
Yonish-Rouach, "The p53 tumour suppressor gene: a mediator of a G1 growth arrest and of apoptosis," *Experentia*, 52(10-11):1001-1007 (1996).
Zannettino, et al., "A powerful technique for isolating genes encoding surface antigens using retroviral expression cloning," *J. Immunol.*, 156(2):611-620 (1996).

\* cited by examiner

```
  1  TTTGTGGAGGGCAGCAGAGAGTACCCAGCTGGACATCCTTTCCTGCTGATGAGCCCCAGG   60
  1                                                      M  S  P  R    4

61  CTGGAGGTGCCCTGCTCACATGCTCTTCCCCAGGGTCTCTCGCCTGGGCAGGTCATCATA  120
  5   L  E  V  P  C  S  H  A  L  P  Q  G  L  S  P  G  Q  V  I  I   24

121  GTACGGGGACTGGTCTTGCAAGAGCCGAAGCATTTTACTGTGAGCCTGAGGGACCAGGCT  180
 25   V  R  G  L  V  L  Q  E  P  K  H  F  T  V  S  L  R  D  Q  A   44

181  GCCCATGCTCCTGTGACACTCAGGGCCTCCTTCGCAGACAGAACTCTGGCCTGGATCTCC  240
 45   A  H  A  P  V  T  L  R  A  S  F  A  D  R  T  L  A  W  I  S   64

241  CGCTGGGGGCAGAAGAAACTGATCTCAGCCCCCTTCCTCTTTTACCCCAGAGATTCTTT   300
 65   R  W  G  Q  K  K  L  I  S  A  P  F  L  F  Y  P  Q  R  F  F   84

301  GAGGTGCTGCTCCTGTTCCAGGAGGGAGGGCTGAAGCTGGCGCTCAATGGGCAGGGGCTG  360
 85   E  V  L  L  L  F  Q  E  G  G  L  K  L  A  L  N  G  Q  G  L  104

361  GGGGCCACCAGCATGAACCAGCAGGCCCTGGAGCAGCTGCGGGAGCTCCGGATCAGTGGA  420
105   G  A  T  S  M  N  Q  Q  A  L  E  Q  L  R  E  L  R  I  S  G  124

421  AGTGTCCAGCTCTACTGTGTCCACTCCTGAAGGATGGTTCCAGGAAATACCGCAGAAAAC  480
125   S  V  Q  L  Y  C  V  H  S  *                                 134

481  AAGAGTCAGCCACTCCCCAGGGCCCCACTCTCCTCCCCTCATTAAACCATCCACCTGAAC  540

541  ACCAGCACATCAGGGCCTGGTTCACCTCTGGGGTCACGAGACTGAGTCTACAGGAGCTTT  600

601  GGGCCTGAGGGAAGGCACAAGAGTGCAAAGGTTCCTCGAACTCTGCACCTTCCTCCACCA  660

661  GGAGCCTGGGATATGGCTCCATCTGCCTTCAGGGCCTGGACTGCACTCACAGAGGCAAGT  720

721  GTTGTAGACTAACAAAGATACTCCAAAATACAATGGCTTAAAGAATGTGGTCATTTATTC  780

781  TTTATTATTTATTTATTTGTGGTCAAATAAATAAATAAGGTTATTTATTTAAAAAAAAA   840

841  AAAAAAAAAAAAAAAAAAAAAAAA   865
```

FIG. 1

```
                    10              20              30              40
 1  M S - - - - - - - P R L E - - - - - - - - - V P C S H A L P Q G L S P G Q V   HJACE54.aa
 1  M S S F S T Q T P Y P N L A - - - - - - - - V P F F T S I P N G L Y P S K S   rGalectin-5.aa
 1  M M - - - - - - - L S L N N L Q N I I Y N P V I P F V G T L P D Q L D P G T L hGalectin-8.aa 50              60              70              80
23  I I V R G L V L Q E P K H F T V S L R D Q A A - - - - - - - - - - - - - - -   HJACE54.aa
31  I V I S G V V L S D A K R F Q I N L R C - G G - - - - - - - - - - - - - - -   rGalectin-5.aa
33  I V I R G H V P S D A D R F Q V D L Q N - G S S M K P R A D V A F H F N P R F K hGalectin-8.aa 90             100             110             120
46  - - - - - - - - - - - - - - - - - - - - - - - - - - - - - - - - - - - - -   HJACE54.aa
53  - - - - - - - - - - - - - - - - - - - - - - - - - - - - - - - - - - - - -   rGalectin-5.aa
72  R A G C I V C N T L I N E K W G R E E I T Y D T P F Q K E K K S F E I V I M V L hGalectin-8.aa 130             140             150             160
46  - - - - - - - - - - - - - - - - - - - - - - - - - - - - - - - - - - - - -   HJACE54.aa
53  - - - - - - - - - - - - - - - - - - - - - - - - - - - - - - - - - - - - -   rGalectin-5.aa
112 K A K F Q V A V N G K H T L L Y G H R I G P E K I D T L G I Y G K V N I H S I G hGalectin-8.aa 170             180             190             200
46  - - - - - - - - - - - - - - - - - - - - - - - - - - - - - - - - - - - - -   HJACE54.aa
53  - - - - - - - - - - - - - - - - - - - - - - - - - - - - - - - - - - - - -   rGalectin-5.aa
152 F S F S S D L Q S T Q A S S L E L T E I S R E N V P K S G T P Q L R L P F A A R hGalectin-8.aa 210             220             230             240
46  - - - - - - - - - - - - - - - - - - - - - - - - - - - H A P V T L             HJACE54.aa
53  - - - - - - - - - - - - - - - - - - - - - - - - - - - D I A F H L             rGalectin-5.aa
192 L N T P M G P G R T V V V K G E V N A N A K S F N V D L L A G K S K D L I A L H L hGalectin-8.aa 250             260             270             280
52  R A S F A D R T L A W I S - - - R W G - Q K K L I S A P F L F Y P Q R F F E V   HJACE54.aa
59  N P R F D E N A V V R N T Q I N N S W G P E E R S L P G S M P F S R G Q R F S V rGalectin-5.aa
232 N P R L N I K A F V R N S F L Q E S W G - E E E R N I T S F P F S P G M Y F E M hGalectin-8.aa 290             300             310             320
87  L L L F Q E G G L K L A L N G Q G L G A T S M N Q Q A L E Q L R E L R I S G S V HJACE54.aa
99  W I L C E G H C F K V A V D G Q H I C E Y S H R L M N L P D I N T L E V A G D I rGalectin-5.aa
271 I I Y C D V R E F K V A V N G V H S L E Y K H R F K E L S S I D T L E I N G D I hGalectin-8.aa 330
127 Q L Y C V H S         HJACE54.aa
139 Q L - - T H V E T     rGalectin-5.aa
311 H L - - L E V R S W   hGalectin-8.aa Decoration 'Decoration #1': Box residues that match the consensus named 'Consensus #2'
exactly.

Decoration 'Decoration #2': Shade (with solid black) residues that match the consensus named
 Consensus #1' exactly
```

FIG. 2

```
                                                   agcccttctccaaa
 16  cctgcatggatgagttcctttctgttcaggtggttcctta tgtcacgacgatttt ggaggcctgcatgcaggcaag
 95  atg gtc atg ctg caa gtg cct gga gtg cct cta gat gca cac agg ttc cag gtg gac ttc cag
  1   M   V   M   L   Q   V   P   G   V   P   L   D   A   H   R   F   Q   V   D   F   Q
155  tgt ggc tgc agc ctg tgt ccc cgg gtc ccc aac ttc cac gcc ttc aac cct cgc ttc cat
 21   C   G   C   S   L   C   P   R   V   P   N   F   H   A   F   N   P   R   F   H
215  acc acc aag ccc cat gtc tgc atc gtc cat ctg gga cat ggg caa cgc caa agg gag gcc
 41   T   T   K   P   H   V   C   I   V   H   L   G   H   G   Q   R   Q   R   E   A
275  cgg tgg ccc cac ctg gcc cga aga ctc tcc agc ctg ttt ctc atc ttt ctc ttc ggg
 61   R   W   P   H   L   A   R   R   L   S   S   L   F   L   I   F   L   F   G
335  aat gag gaa gtg aag gtg aat gtg ggt gac cac ctg cac atc cgc cac tac cgg ctc
 81   N   E   E   V   K   V   N   V   G   D   H   L   H   I   R   H   Y   R   L
395  cca ctg tct cat gtg gac atc aat cca cag cac ttt ggt gac atc ctg gag gct gtt gga
101   P   L   S   H   V   D   I   N   P   Q   H   F   G   D   I   L   V   E   A   V   G
455  ttc ctg aac atc cca agg agt aga gga gtg gag ggc tac cca gct ggt cca cat cct ttc
121   F   L   N   I   P   R   S   R   G   V   E   G   Y   P   A   G   H   P   F
515  ctg ctg atg agc cag gtc ata gta cgg gag gtg ccc tgc tca gct ctt ccc aag ctc tcg
141   L   L   M   S   Q   V   I   V   R   E   V   P   C   S   A   L   P   K   L   S
575  cct ggg cag ctg cgg gac gtc ttg caa gag cgg gga ctg gtc ctg aca cat ttt act gtg
161   P   G   Q   L   R   D   V   L   Q   E   R   G   L   V   L   T   H   F   T   V
635  agc ctg agg gac cag gat gcc cat ggg tgg gtg aag aag tcc ttc gcc gac aga
181   S   L   R   D   Q   D   A   H   G   W   V   K   K   S   F   A   D   R
695  act ctg gcc tgg atc ttc cgc atc ctg gag gtg ctg ctg ctt
201   T   L   A   W   I   F   R   I   L   E   V   L   L   L
755  tac ccc cag aga cag atg ctc ctc agc atg aac cag aag cag ctg aag cag ctg cgg
221   Y   P   Q   R   Q   M   L   L   S   M   N   Q   K   Q   L   K   Q   L   R
815  ctc aat ggg cag cag ggg ctg ttt cag gcc acc gcc ctg gag cag ctg cgg
241   L   N   G   Q   Q   G   L   F   Q   A   T   A   L   E   Q   L   R
875  gag ctc cgg agt gga atc gtc cag gtc tac tgt gtc cac tcc tgaggatggttccagggaaa
261   E   L   R   S   G   I   V   Q   V   Y   C   V   H   S   *
```

FIG. 6A taccgccagaaacaagaaggtcagcgcccactctcctccctcattaaaccatccacctgacaccag
cacatcaggcctggttcacctctggggtcacgagactgagtctacaggagctttgggcctgaggaaggcacaagagtgc
aaaggttcctcgaactctgcacctcctccaccaggagcctgggatatggctccatctgccttcagggcctgactgcac
tcacagaggcaagtgttgtagactaacaaagatactccaaaatacaatggcttaaagaatgtggtcattattctttatt
atttattttgtggtcaaataaataaggttatttatttaaaaaaaaaaaaaaaaaaaaaaaaa

FIG. 6B

MVMLQGVVPLDAHRFQVDFQCGCSLCPRP α
         |||||||||||||
MSFFSCSGGSLCHDDFWRPACRQDGHAAARSGPSRCTQVDFQCGCSLCPRP β

FIG. 8

SEQUENCE LISTING

```
<160> NUMBER OF SEQ ID NOS: 27

<210> SEQ ID NO 1
<211> LENGTH: 865
<212> TYPE: DNA
<213> ORGANISM: Homo sapiens

<400> SEQUENCE: 1
tttgtggagg gcagcagaga gtacccagct ggacatcctt tcctgctgat gagcccagg      60 ctggaggtgc cctgctcaca tgctcttccc cagggtctct cgcctgggca ggtcatcata     120
gtacggggac tggtcttgca agagccgaag cattttactg tgagcctgag ggaccaggct    180
gcccatgctc ctgtgacact cagggcctcc ttcgcagaca gaactctggc ctggatctcc    240
cgctgggggc agaagaaact gatctcagcc cccttcctct tttaccccca gagattcttt    300
gaggtgctgc tcctgttcca ggagggaggg ctgaagctgg cgctcaatgg gcaggggctg    360
ggggccacca gcatgaacca gcaggccctg gagcagctgc gggagctccg gatcagtgga    420
agtgtccagc tctactgtgt ccactcctga aggatggttc caggaaatac cgcagaaaac    480
aagagtcagc cactccccag ggccccactc tcctcccctc attaaaccat ccacctgaac    540
accagcacat cagggcctgg ttcacctctg gggtcacgag actgagtcta caggagcttt    600
```

```
gggcctgagg gaaggcacaa gagtgcaaag gttcctcgaa ctctgcacct tcctccacca    660
ggagcctggg atatggctcc atctgccttc agggcctgga ctgcactcac agaggcaagt    720
gttgtagact aacaaagata ctccaaaata caatggctta agaatgtggg tcatttattc    780
tttattattt atttatttgt ggtcaaataa ataaataagg ttatttattt aaaaaaaaaa    840
aaaaaaaaaa aaaaaaaaaa aaaaa                                         865
```

<210> SEQ ID NO 2
<211> LENGTH: 133
<212> TYPE: PRT
<213> ORGANISM: Homo sapiens

<400> SEQUENCE: 2

```
Met Ser Pro Arg Leu Glu Val Pro Cys Ser His Ala Leu Pro Gln Gly
  1               5                  10                  15

Leu Ser Pro Gly Gln Val Ile Ile Val Arg Gly Leu Val Leu Gln Glu
             20                  25                  30

Pro Lys His Phe Thr Val Ser Leu Arg Asp Gln Ala Ala His Ala Pro
         35                  40                  45

Val Thr Leu Arg Ala Ser Phe Ala Asp Arg Thr Leu Ala Trp Ile Ser
     50                  55                  60

Arg Trp Gly Gln Lys Lys Leu Ile Ser Ala Pro Phe Leu Phe Tyr Pro
 65                  70                  75                  80

Gln Arg Phe Phe Glu Val Leu Leu Phe Gln Glu Gly Gly Leu Lys
                 85                  90                  95

Leu Ala Leu Asn Gly Gln Gly Leu Gly Ala Thr Ser Met Asn Gln Gln
            100                 105                 110

Ala Leu Glu Gln Leu Arg Glu Leu Arg Ile Ser Gly Ser Val Gln Leu
        115                 120                 125

Tyr Cys Val His Ser
    130
```

<210> SEQ ID NO 3
<211> LENGTH: 145
<212> TYPE: PRT
<213> ORGANISM: Homo sapiens

<400> SEQUENCE: 3

```
Met Ser Ser Phe Ser Thr Gln Thr Pro Tyr Pro Asn Leu Ala Val Pro
  1               5                  10                  15

Phe Phe Thr Ser Ile Pro Asn Gly Leu Tyr Pro Ser Lys Ser Ile Val
             20                  25                  30

Ile Ser Gly Val Val Leu Ser Asp Ala Lys Arg Phe Gln Ile Asn Leu
         35                  40                  45

Arg Cys Gly Gly Asp Ile Ala Phe His Leu Asn Pro Arg Phe Asp Glu
     50                  55                  60

Asn Ala Val Val Arg Asn Thr Gln Ile Asn Asn Ser Trp Gly Pro Glu
 65                  70                  75                  80

Glu Arg Ser Leu Pro Gly Ser Met Pro Phe Ser Arg Gly Gln Arg Phe
                 85                  90                  95

Ser Val Trp Ile Leu Cys Glu Gly His Cys Phe Lys Val Ala Val Asp
            100                 105                 110

Gly Gln His Ile Cys Glu Tyr Ser His Arg Leu Met Asn Leu Pro Asp
        115                 120                 125

Ile Asn Thr Leu Glu Val Ala Gly Asp Ile Gln Leu Thr His Val Glu
    130                 135                 140
```

Thr
145

<210> SEQ ID NO 4
<211> LENGTH: 318
<212> TYPE: PRT
<213> ORGANISM: Homo sapiens

<400> SEQUENCE: 4

```
Met Met Leu Ser Leu Asn Asn Leu Gln Asn Ile Ile Tyr Asn Pro Val
 1               5                  10                  15

Ile Pro Phe Val Gly Thr Ile Pro Asp Gln Leu Asp Pro Gly Thr Leu
                20                  25                  30

Ile Val Ile Arg Gly His Val Pro Ser Asp Ala Asp Arg Phe Gln Val
            35                  40                  45

Asp Leu Gln Asn Gly Ser Ser Met Lys Pro Arg Ala Asp Val Ala Phe
        50                  55                  60

His Phe Asn Pro Arg Phe Lys Arg Ala Gly Cys Ile Val Cys Asn Thr
 65                  70                  75                  80

Leu Ile Asn Glu Lys Trp Gly Arg Glu Glu Ile Thr Tyr Asp Thr Pro
                85                  90                  95

Phe Gln Lys Glu Lys Lys Ser Phe Glu Ile Val Ile Met Val Leu Lys
               100                 105                 110

Ala Lys Phe Gln Val Ala Val Asn Gly Lys His Thr Leu Leu Tyr Gly
            115                 120                 125

His Arg Ile Gly Pro Glu Lys Ile Asp Thr Leu Gly Ile Tyr Gly Lys
        130                 135                 140

Val Asn Ile His Ser Ile Gly Phe Ser Phe Ser Ser Asp Leu Gln Ser
145                 150                 155                 160

Thr Gln Ala Ser Ser Leu Glu Leu Thr Glu Ile Ser Arg Glu Asn Val
                165                 170                 175

Pro Lys Ser Gly Thr Pro Gln Leu Arg Leu Pro Phe Ala Ala Arg Leu
            180                 185                 190

Asn Thr Pro Met Gly Pro Gly Arg Thr Val Val Lys Gly Glu Val
        195                 200                 205

Asn Ala Asn Ala Lys Ser Phe Asn Val Asp Leu Leu Ala Gly Lys Ser
    210                 215                 220

Lys Asp Ile Ala Leu His Leu Asn Pro Arg Leu Asn Ile Lys Ala Phe
225                 230                 235                 240

Val Arg Asn Ser Phe Leu Gln Glu Ser Trp Gly Glu Glu Glu Arg Asn
                245                 250                 255

Ile Thr Ser Phe Pro Phe Ser Pro Gly Met Tyr Phe Glu Met Ile Ile
            260                 265                 270

Tyr Cys Asp Val Arg Glu Phe Lys Val Ala Val Asn Gly Val His Ser
        275                 280                 285

Leu Glu Tyr Lys His Arg Phe Lys Glu Leu Ser Ser Ile Asp Thr Leu
    290                 295                 300

Glu Ile Asn Gly Asp Ile His Leu Leu Val Arg Ser Trp
305                 310                 315
```

<210> SEQ ID NO 5
<211> LENGTH: 5
<212> TYPE: PRT
<213> ORGANISM: Homo sapiens
<220> FEATURE:
<221> NAME/KEY: Site

```
<222> LOCATION: (3)
<223> OTHER INFORMATION: Xaa equals any amino acid

<400> SEQUENCE: 5

Trp Ser Xaa Trp Ser
 1               5

<210> SEQ ID NO 6
<211> LENGTH: 28
<212> TYPE: DNA
<213> ORGANISM: Homo sapiens

<400> SEQUENCE: 6
cgcaagcttt caggagtgga cacagtag                                           28

<210> SEQ ID NO 7
<211> LENGTH: 32
<212> TYPE: DNA
<213> ORGANISM: Homo sapiens

<400> SEQUENCE: 7
cgccccgggg cctatgagcc ccaggctgga gg                                      32

<210> SEQ ID NO 8
<211> LENGTH: 28
<212> TYPE: DNA
<213> ORGANISM: Homo sapiens

<400> SEQUENCE: 8
cgcggtacct caggagtgga cacagtag                                           28

<210> SEQ ID NO 9
<211> LENGTH: 44
<212> TYPE: DNA
<213> ORGANISM: Homo sapiens

<400> SEQUENCE: 9
cgccccgggg ccatcatggc ctatcatgag ccccaggctg gagg                         44

<210> SEQ ID NO 10
<211> LENGTH: 23
<212> TYPE: DNA
<213> ORGANISM: Homo sapiens

<400> SEQUENCE: 10
cgccgccacc atgagcccca ggc                                                23

<210> SEQ ID NO 11
<211> LENGTH: 22
<212> TYPE: DNA
<213> ORGANISM: Homo sapiens

<400> SEQUENCE: 11
ggaatctaga tcaggagtgg ac                                                 22

<210> SEQ ID NO 12
<211> LENGTH: 865
<212> TYPE: DNA
<213> ORGANISM: Homo sapiens

<400> SEQUENCE: 12
tttttttttt tttttttttt tttttttttt ttttaaata aataacctta tttatttatt         60
tgaccacaaa taaataaata ataaagaata aatgaccaca ttctttaagc cattgtattt       120
```

```
tggagtatct tgttagtct acaacacttg cctctgtgag tgcagtccag gccctgaagg    180
cagatggagc catatcccag gctcctggtg gaggaaggtg cagagttcga ggaacctttg    240
cactcttgtg ccttccctca ggcccaaagc tcctgtagac tcagtctcgt gaccccagag    300
gtgaaccagg ccctgatgtg ctggtgttca ggtggatggt ttaatgaggg gaggagagtg    360
gggccctggg gagtggctga ctcttgtttt ctgcggtatt tcctggaacc atccttcagg    420
agtggacaca gtagagctgg acacttccac tgatccggag ctcccgcagc tgctccaggg    480
cctgctggtt catgctggtg gcccccagcc cctgcccatt gagcgccagc ttcagccctc    540
cctcctggaa caggagcagc acctcaaaga atctctgggg gtaaagagg aaggggctg     600 agatcagttt cttctgcccc cagcgggaga tccaggccag agttctgtct gcgaaggagg    660
ccctgagtgt cacaggagca tgggcagcct ggtccctcag gctcacagta aaatgcttcg    720
gctcttgcaa gaccagtccc cgtactatga tgacctgccc aggcgagaga ccctggggaa    780
gagcatgtga gcagggcacc tccagcctgg ggctcatcag caggaaagga tgtccagctg    840
ggtactctct gctgccctcc acaaa                                          865
```

<210> SEQ ID NO 13
<211> LENGTH: 733
<212> TYPE: DNA
<213> ORGANISM: Homo sapiens

<400> SEQUENCE: 13

```
gggatccgga gcccaaatct tctgacaaaa ctcacacatg cccaccgtgc ccagcacctg     60
aattcgaggg tgcaccgtca gtcttcctct ccccccaaa acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca accccatcg    360 agaaaaccat ctccaaagcc aaagggcagc ccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                       733
```

<210> SEQ ID NO 14
<211> LENGTH: 86
<212> TYPE: DNA
<213> ORGANISM: Homo sapiens

<400> SEQUENCE: 14

```
gcgcctcgag atttccccga aatctagatt tccccgaaat gatttccccg aaatgatttc     60
cccgaaatat ctgccatctc aattag                                          86
```

<210> SEQ ID NO 15
<211> LENGTH: 27
<212> TYPE: DNA
<213> ORGANISM: Homo sapiens

```
<400> SEQUENCE: 15
gcggcaagct ttttgcaaag cctaggc                                27

<210> SEQ ID NO 16
<211> LENGTH: 271
<212> TYPE: DNA
<213> ORGANISM: Homo sapiens

<400> SEQUENCE: 16
ctcgagattt ccccgaaatc tagatttccc cgaaatgatt tccccgaaat gatttccccg    60
aaatatctgc catctcaatt agtcagcaac catagtcccg cccctaactc cgcccatccc   120
gcccctaact ccgcccagtt ccgcccattc tccgccccat ggctgactaa ttttttttat   180
ttatgcagag gccgaggccg cctcggcctc tgagctattc cagaagtagt gaggaggctt   240
ttttggaggc ctaggctttt gcaaaaagct t                                  271

<210> SEQ ID NO 17
<211> LENGTH: 32
<212> TYPE: DNA
<213> ORGANISM: Homo sapiens

<400> SEQUENCE: 17
gcgctcgagg gatgacagcg atagaacccc gg                                 32

<210> SEQ ID NO 18
<211> LENGTH: 31
<212> TYPE: DNA
<213> ORGANISM: Homo sapiens

<400> SEQUENCE: 18
gcgaagcttc gcgactcccc ggatccgcct c                                  31

<210> SEQ ID NO 19
<211> LENGTH: 12
<212> TYPE: DNA
<213> ORGANISM: Homo sapiens

<400> SEQUENCE: 19
ggggactttc cc                                                       12

<210> SEQ ID NO 20
<211> LENGTH: 73
<212> TYPE: DNA
<213> ORGANISM: Homo sapiens

<400> SEQUENCE: 20
gcggcctcga ggggactttc ccggggactt tccggggact tccgggact ttccatcctg    60 ccatctcaat tag                                                      73

<210> SEQ ID NO 21
<211> LENGTH: 27
<212> TYPE: DNA
<213> ORGANISM: Homo sapiens

<400> SEQUENCE: 21
gcggcaagct ttttgcaaag cctaggc                                       27

<210> SEQ ID NO 22
<211> LENGTH: 256
<212> TYPE: DNA
<213> ORGANISM: Homo sapiens
```

```
<400> SEQUENCE: 22
ctcgagggga ctttcccggg gactttccgg ggactttccg ggactttcca tctgccatct      60
caattagtca gcaaccatag tcccgcccct aactccgccc atcccgcccc taactccgcc     120
cagttccgcc cattctccgc cccatggctg actaattttt tttatttatg cagaggccga     180
ggccgcctcg gcctctgagc tattccagaa gtagtgagga ggcttttttg gaggcctagg     240
cttttgcaaa aagctt                                                     256

<210> SEQ ID NO 23
<211> LENGTH: 30
<212> TYPE: DNA
<213> ORGANISM: Homo sapiens

<400> SEQUENCE: 23
cgcccatgga tgagcccag gctggaggtg                                         30

<210> SEQ ID NO 24
<211> LENGTH: 1337
<212> TYPE: DNA
<213> ORGANISM: Homo sapiens
<220> FEATURE:
<221> NAME/KEY: CDS
<222> LOCATION: (95)..(919)

<400> SEQUENCE: 24 agcccttct ccaaacctgc atggatgagt ttctttttctt gttcaggtgg ttccttatgt       60
cacgacgatt tttggaggcc tgcatgcagg caag atg gtc atg ctg caa gga gtg     115
                                    Met Val Met Leu Gln Gly Val
                                      1               5 gtc cct cta gat gca cac agg ttt cag gtg gac ttc cag tgt ggc tgc        163
Val Pro Leu Asp Ala His Arg Phe Gln Val Asp Phe Gln Cys Gly Cys
         10                  15                  20 agc ctg tgt ccc cgg cca gat atc gcc ttc cac ttc aac cct cgc ttc        211
Ser Leu Cys Pro Arg Pro Asp Ile Ala Phe His Phe Asn Pro Arg Phe
     25                  30                  35 cat acc acc aag ccc cat gtc atc tgc aac acc ctg cat ggt gga cgc        259
His Thr Thr Lys Pro His Val Ile Cys Asn Thr Leu His Gly Gly Arg
 40                  45                  50                  55 tgg caa agg gag gcc cgg tgg ccc cac ctg gcc ctg cga aga ggc tcc        307
Trp Gln Arg Glu Ala Arg Trp Pro His Leu Ala Leu Arg Arg Gly Ser
                 60                  65                  70 agc ttc ctc atc ctc ttt ctc ttc ggg aat gag gaa gtg aag gtg agt        355
Ser Phe Leu Ile Leu Phe Leu Phe Gly Asn Glu Glu Val Lys Val Ser
             75                  80                  85 gtg aat gga cag cac ttt ctc cac ttc cgc tac cgg ctc cca ctg tct        403
Val Asn Gly Gln His Phe Leu His Phe Arg Tyr Arg Leu Pro Leu Ser
         90                  95                 100 cat gtg gac acg ctg ggt ata ttt ggt gac atc ctg gta gag gct gtt        451
His Val Asp Thr Leu Gly Ile Phe Gly Asp Ile Leu Val Glu Ala Val
    105                 110                 115 gga ttc ctg aac atc aat cca ttt gtg gag ggc agc aga gag tac cca        499
Gly Phe Leu Asn Ile Asn Pro Phe Val Glu Gly Ser Arg Glu Tyr Pro
120                 125                 130                 135 gct gga cat cct ttc ctg ctg atg agc ccc agg ctg gag gtg ccc tgc        547
Ala Gly His Pro Phe Leu Leu Met Ser Pro Arg Leu Glu Val Pro Cys
                140                 145                 150 tca cat gct ctt ccc cag ggt ctc tcg cct ggg cag gtc atc ata gta        595
Ser His Ala Leu Pro Gln Gly Leu Ser Pro Gly Gln Val Ile Ile Val
            155                 160                 165
```

| | | | | | | | | | | | | | | | | |
|---|---|---|---|---|---|---|---|---|---|---|---|---|---|---|---|---|
| cgg | gga | ctg | gtc | ttg | caa | gag | ccg | aag | cat | ttt | act | gtg | agc | ctg | agg | 643 |
| Arg | Gly | Leu | Val | Leu | Gln | Glu | Pro | Lys | His | Phe | Thr | Val | Ser | Leu | Arg | |
| | | 170 | | | | | 175 | | | | | 180 | | | | |
| gac | cag | gct | gcc | cat | gct | cct | gtg | aca | ctc | agg | gcc | tcc | ttc | gca | gac | 691 |
| Asp | Gln | Ala | Ala | His | Ala | Pro | Val | Thr | Leu | Arg | Ala | Ser | Phe | Ala | Asp | |
| 185 | | | | | 190 | | | | | 195 | | | | | | |
| aga | act | ctg | gcc | tgg | atc | tcc | cgc | tgg | ggg | cag | aag | aaa | ctg | atc | tca | 739 |
| Arg | Thr | Leu | Ala | Trp | Ile | Ser | Arg | Trp | Gly | Gln | Lys | Lys | Leu | Ile | Ser | |
| 200 | | | | | 205 | | | | | 210 | | | | | 215 | |
| gcc | ccc | ttc | ctc | ttt | tac | ccc | cag | aga | ttc | ttt | gag | gtg | ctg | ctc | ctg | 787 |
| Ala | Pro | Phe | Leu | Phe | Tyr | Pro | Gln | Arg | Phe | Phe | Glu | Val | Leu | Leu | Leu | |
| | | | | 220 | | | | | 225 | | | | | 230 | | |
| ttc | cag | gag | gga | ggg | ctg | aag | ctg | gcg | ctc | aat | ggg | cag | ggg | ctg | ggg | 835 |
| Phe | Gln | Glu | Gly | Gly | Leu | Lys | Leu | Ala | Leu | Asn | Gly | Gln | Gly | Leu | Gly | |
| | | | 235 | | | | | 240 | | | | | 245 | | | |
| gcc | acc | agc | atg | aac | cag | cag | gcc | ctg | gag | cag | ctg | cgg | gag | ctc | cgg | 883 |
| Ala | Thr | Ser | Met | Asn | Gln | Gln | Ala | Leu | Glu | Gln | Leu | Arg | Glu | Leu | Arg | |
| | | | 250 | | | | | 255 | | | | | 260 | | | |
| atc | agt | gga | agt | gtc | cag | ctc | tac | tgt | gtc | cac | tcc | tgaaggatgg | | | | 929 |
| Ile | Ser | Gly | Ser | Val | Gln | Leu | Tyr | Cys | Val | His | Ser | | | | | |
| | | 265 | | | | | 270 | | | | | 275 | | | | |

| | |
|---|---|
| ttccaggaaa taccgcagaa acaagagtc agccactccc cagggcccca ctctcctccc | 989 |
| ctcattaaac catccacctg aacaccagca catcagggcc tggttcacct ctggggtcac | 1049 |
| gagactgagt ctacaggagc tttgggcctg agggaaggca caagagtgca aaggttcctc | 1109 |
| gaactctgca ccttcctcca ccaggagcct gggatatggc tccatctgcc ttcagggcct | 1169 |
| ggactgcact cacagaggca agtgttgtag actaacaaag atactccaaa atacaatggc | 1229 |
| ttaaagaatg tggtcattta ttctttatta tttatttatt tgtggtcaaa taataaata | 1289 |
| aggttattta tttaaaaaaa aaaaaaaaaa aaaaaaaaaa aaaaaaa | 1337 |

<210> SEQ ID NO 25
<211> LENGTH: 275
<212> TYPE: PRT
<213> ORGANISM: Homo sapiens

<400> SEQUENCE: 25

| | | | | | | | | | | | | | | |
|---|---|---|---|---|---|---|---|---|---|---|---|---|---|---|
| Met | Val | Met | Leu | Gln | Gly | Val | Val | Pro | Leu | Asp | Ala | His | Arg | Phe | Gln |
| 1 | | | | 5 | | | | | 10 | | | | | 15 | |
| Val | Asp | Phe | Gln | Cys | Gly | Cys | Ser | Leu | Cys | Pro | Arg | Pro | Asp | Ile | Ala |
| | | | 20 | | | | | 25 | | | | | 30 | | |
| Phe | His | Phe | Asn | Pro | Arg | Phe | His | Thr | Thr | Lys | Pro | His | Val | Ile | Cys |
| | | 35 | | | | | 40 | | | | | 45 | | | |
| Asn | Thr | Leu | His | Gly | Gly | Arg | Trp | Gln | Arg | Glu | Ala | Arg | Trp | Pro | His |
| | 50 | | | | | 55 | | | | | 60 | | | | |
| Leu | Ala | Leu | Arg | Arg | Gly | Ser | Ser | Phe | Leu | Ile | Leu | Phe | Leu | Phe | Gly |
| 65 | | | | | 70 | | | | | 75 | | | | | 80 |
| Asn | Glu | Glu | Val | Lys | Val | Ser | Val | Asn | Gly | Gln | His | Phe | Leu | His | Phe |
| | | | | 85 | | | | | 90 | | | | | 95 | |
| Arg | Tyr | Arg | Leu | Pro | Leu | Ser | His | Val | Asp | Thr | Leu | Gly | Ile | Phe | Gly |
| | | | 100 | | | | | 105 | | | | | 110 | | |
| Asp | Ile | Leu | Val | Glu | Ala | Val | Gly | Phe | Leu | Asn | Ile | Asn | Pro | Phe | Val |
| | | 115 | | | | | 120 | | | | | 125 | | | |
| Glu | Gly | Ser | Arg | Glu | Tyr | Pro | Ala | Gly | His | Pro | Phe | Leu | Leu | Met | Ser |
| | 130 | | | | | 135 | | | | | 140 | | | | |
| Pro | Arg | Leu | Glu | Val | Pro | Cys | Ser | His | Ala | Leu | Pro | Gln | Gly | Leu | Ser |

-continued

```
            145                 150                 155                 160
Pro Gly Gln Val Ile Ile Val Arg Gly Leu Val Leu Gln Glu Pro Lys
                    165                 170                 175
His Phe Thr Val Ser Leu Arg Asp Gln Ala Ala His Ala Pro Val Thr
            180                 185                 190
Leu Arg Ala Ser Phe Ala Asp Arg Thr Leu Ala Trp Ile Ser Arg Trp
        195                 200                 205
Gly Gln Lys Lys Leu Ile Ser Ala Pro Phe Leu Phe Tyr Pro Gln Arg
    210                 215                 220
Phe Phe Glu Val Leu Leu Leu Phe Gln Glu Gly Leu Lys Leu Ala
225                 230                 235                 240
Leu Asn Gly Gln Gly Leu Gly Ala Thr Ser Met Asn Gln Gln Ala Leu
                245                 250                 255
Glu Gln Leu Arg Glu Leu Arg Ile Ser Gly Ser Val Gln Leu Tyr Cys
            260                 265                 270
Val His Ser
        275

<210> SEQ ID NO 26
<211> LENGTH: 1330
<212> TYPE: DNA
<213> ORGANISM: Homo sapiens
<220> FEATURE:
<221> NAME/KEY: CDS
<222> LOCATION: (25)..(912)

<400> SEQUENCE: 26 agcccttct  ccaaacctgc atgg atg agt ttc ttt tct tgt tca ggt ggt        51
                         Met Ser Phe Phe Ser Cys Ser Gly Gly
                          1               5 tcc tta tgt cac gac gat ttt tgg agg cct gca tgc agg caa gat ggt       99
Ser Leu Cys His Asp Asp Phe Trp Arg Pro Ala Cys Arg Gln Asp Gly
 10              15                  20                  25 cat gct gca agg agt ggt ccc tct aga tgc aca cag gtg gac ttc cag      147
His Ala Ala Arg Ser Gly Pro Ser Arg Cys Thr Gln Val Asp Phe Gln
             30                  35                  40 tgt ggc tgc agc ctg tgt ccc cgg cca gat atc gcc ttc cac ttc aac      195
Cys Gly Cys Ser Leu Cys Pro Arg Pro Asp Ile Ala Phe His Phe Asn
         45                  50                  55 cct cgc ttc cat acc acc aag ccc cat gtc atc tgc aac acc ctg cat      243
Pro Arg Phe His Thr Thr Lys Pro His Val Ile Cys Asn Thr Leu His
     60                  65                  70 ggt gga cgc tgg caa agg gag gcc cgg tgg ccc cac ctg gcc ctg cga      291
Gly Gly Arg Trp Gln Arg Glu Ala Arg Trp Pro His Leu Ala Leu Arg
 75                  80                  85 aga ggc tcc agc ttc ctc atc ctc ttt ctc ttc ggg aat gag gaa gtg      339
Arg Gly Ser Ser Phe Leu Ile Leu Phe Leu Phe Gly Asn Glu Glu Val
 90                  95                 100                 105 aag gtg agt gtg aat gga cag cac ttt ctc cac ttc gcc tac cgg ctc      387
Lys Val Ser Val Asn Gly Gln His Phe Leu His Phe Arg Tyr Arg Leu
                 110                 115                 120 cca ctg tct cat gtg gac acg ctg ggt ata ttt ggt gac atc ctg gta      435
Pro Leu Ser His Val Asp Thr Leu Gly Ile Phe Gly Asp Ile Leu Val
             125                 130                 135 gag gct gtt gga ttc ctg aac atc aat cca ttt gtg gag ggc agc aga      483
Glu Ala Val Gly Phe Leu Asn Ile Asn Pro Phe Val Glu Gly Ser Arg
         140                 145                 150 gag tac cca gct gga cat cct ttc ctg ctg atg agc ccc agg ctg gag      531
Glu Tyr Pro Ala Gly His Pro Phe Leu Leu Met Ser Pro Arg Leu Glu
```

```
                155                 160                 165
gtg ccc tgc tca cat gct ctt ccc cag ggt ctc tcg cct ggg cag gtc       579
Val Pro Cys Ser His Ala Leu Pro Gln Gly Leu Ser Pro Gly Gln Val
170             175                 180                 185 atc ata gta cgg gga ctg gtc ttg caa gag ccg aag cat ttt act gtg       627
Ile Ile Val Arg Gly Leu Val Leu Gln Glu Pro Lys His Phe Thr Val
            190                 195                 200 agc ctg agg gac cag gct gcc cat gct cct gtg aca ctc agg gcc tcc       675
Ser Leu Arg Asp Gln Ala Ala His Ala Pro Val Thr Leu Arg Ala Ser
                205                 210                 215 ttc gca gac aga act ctg gcc tgg atc tcc cgc tgg ggg cag aag aaa       723
Phe Ala Asp Arg Thr Leu Ala Trp Ile Ser Arg Trp Gly Gln Lys Lys
            220                 225                 230 ctg atc tca gcc ccc ttc ctc ttt tac ccc cag aga ttc ttt gag gtg       771
Leu Ile Ser Ala Pro Phe Leu Phe Tyr Pro Gln Arg Phe Phe Glu Val
                235                 240                 245 ctc ctg ctg ttc cag gag gga ggg ctg aag ctg gcg ctc aat ggg cag       819
Leu Leu Leu Phe Gln Glu Gly Gly Leu Lys Leu Ala Leu Asn Gly Gln
250                 255                 260                 265 ggg ctg ggg gcc acc agc atg aac cag cag gcc ctg gag cag ctg cgg       867
Gly Leu Gly Ala Thr Ser Met Asn Gln Gln Ala Leu Glu Gln Leu Arg
                270                 275                 280 gag ctc cgg atc agt gga agt gtc cag ctc tac tgt gtc cac tcc           912
Glu Leu Arg Ile Ser Gly Ser Val Gln Leu Tyr Cys Val His Ser
            285                 290                 295 tgaaggatgg ttccaggaaa taccgcagaa acaagagtc agccactccc cagggcccca     972
ctctcctccc ctcattaaac catccacctg aacaccagca catcagggcc tggttcacct   1032
ctggggtcac gagactgagt ctacaggagc tttgggcctg agggaaggca caagagtgca   1092
aaggttcctc gaactctgca ccttcctcca ccaggagcct gggatatggc tccatctgcc   1152
ttcagggcct ggactgcact cacagaggca agtgttgtag actaacaaag atactccaaa   1212
atacaatggc ttaaagaatg tggtcattta ttctttatta tttatttatt tgtggtcaaa   1272
taaataaata aggttattta tttaaaaaaa aaaaaaaaa aaaaaaaaaa aaaaaaa       1330
```

<210> SEQ ID NO 27
<211> LENGTH: 296
<212> TYPE: PRT
<213> ORGANISM: Homo sapiens

<400> SEQUENCE: 27

```
Met Ser Phe Phe Ser Cys Ser Gly Gly Ser Leu Cys His Asp Asp Phe
1               5                   10                  15

Trp Arg Pro Ala Cys Arg Gln Asp Gly His Ala Ala Arg Ser Gly Pro
            20                  25                  30

Ser Arg Cys Thr Gln Val Asp Phe Gln Cys Gly Cys Ser Leu Cys Pro
        35                  40                  45

Arg Pro Asp Ile Ala Phe His Phe Asn Pro Arg Phe His Thr Thr Lys
    50                  55                  60

Pro His Val Ile Cys Asn Thr Leu His Gly Gly Arg Trp Gln Arg Glu
65                  70                  75                  80

Ala Arg Trp Pro His Leu Ala Leu Arg Arg Gly Ser Ser Phe Leu Ile
                85                  90                  95

Leu Phe Leu Phe Gly Asn Glu Glu Val Lys Val Ser Val Asn Gly Gln
            100                 105                 110

His Phe Leu His Phe Arg Tyr Arg Leu Pro Leu Ser His Val Asp Thr
        115                 120                 125
```

```
Leu Gly Ile Phe Gly Asp Ile Leu Val Glu Ala Val Gly Phe Leu Asn
    130                 135                 140
Ile Asn Pro Phe Val Glu Gly Ser Arg Glu Tyr Pro Ala Gly His Pro
145                 150                 155                 160
Phe Leu Leu Met Ser Pro Arg Leu Glu Val Pro Cys Ser His Ala Leu
                165                 170                 175
Pro Gln Gly Leu Ser Pro Gly Gln Val Ile Ile Val Arg Gly Leu Val
                180                 185                 190
Leu Gln Glu Pro Lys His Phe Thr Val Ser Leu Arg Asp Gln Ala Ala
            195                 200                 205
His Ala Pro Val Thr Leu Arg Ala Ser Phe Ala Asp Arg Thr Leu Ala
        210                 215                 220
Trp Ile Ser Arg Trp Gly Gln Lys Lys Leu Ile Ser Ala Pro Phe Leu
225                 230                 235                 240
Phe Tyr Pro Gln Arg Phe Phe Glu Val Leu Leu Leu Phe Gln Glu Gly
                245                 250                 255
Gly Leu Lys Leu Ala Leu Asn Gly Gln Gly Leu Gly Ala Thr Ser Met
                260                 265                 270
Asn Gln Gln Ala Leu Glu Gln Leu Arg Glu Leu Arg Ile Ser Gly Ser
            275                 280                 285
Val Gln Leu Tyr Cys Val His Ser
    290                 295
```

GALECTIN 11

CROSS-REFERENCE TO RELATED APPLICATIONS

This application is a divisional of U.S. application Ser. No. 09/557,170, filed Apr. 21, 2000 now U.S. Pat. No. 6,605,599, which is a continuation-in-part of U.S. application Ser. No. 09/109,864 (abandoned), filed Jul. 6, 1998, which is a continuation-in-part of U.S. application Ser. No. 09/010,146 (abandoned), filed Jan. 21, 1998, which claims benefit under 35 U.S.C. § 119(e) of U.S. Provisional Application No. 60/034,205, filed Jan. 21, 1997 and of U.S. Provisional Application No. 60/034,204, filed Jan. 21, 1997; and said U.S. application Ser. No. 09/557,170 also claims benefit under 35 U.S.C. § 119(e) of U.S. Provisional Application No. 60/169,932, filed Dec. 10, 1999 and of U.S. Provisional Application No. 60/130,390, filed Apr. 21, 1999. Each of the aforementioned non-provisional and provisional applications is hereby incorporated by reference in its entirety.

FIELD OF THE INVENTION

The present invention relates to a novel galectin. More specifically, isolated nucleic acid molecules are provided encoding human galectin 11. Galectin 11 polypeptides are also provided, as are vectors, host cells, recombinant methods for producing the same, and antibodies to galectin 11 polypeptides. The invention further relates to screening methods for identifying agonists and antagonists of galectin 11 activity. Also provided are diagnostic methods for detecting cell growth disorders and therapeutic methods for cell growth disorders, including autoimmune diseases, cancer, and inflammatory diseases.

BACKGROUND OF THE INVENTION

Lectins are proteins that bind to specific carbohydrate structures and can thus recognize particular glycoconjugates. Barondes et al., J. Biol. Chem. 269(33):20807–20810 (1994). Galectins are members of a family of β-galactoside-binding lectins with related amino acid sequences (For review see, Barondes et al., Cell 76:597–598 (1994); Barondes et al., J. Biol. Chem. 269(33):20807–20810 (1994)). Although a large number of glycoproteins containing β-galactoside sugars are produced by the cell, only a few will bind to known galectins in vitro. Such apparent binding specificity suggests a highly specific functional role for the galectins.

Galectin 1 (conventionally termed LGALS1 for lectin, galactoside-binding, soluble-1, but which is also known as: L-14-1, L-14, RL-14.5, galaptin, MGBP, GBP, BHL, CHA, HBP, HPL, HLBP 14, rIML-1) is a homodimer with a subunit molecular mass of 14,500 Daltons. Galectin 1 is expressed abundantly in smooth and skeletal muscle, and to a lesser extent in many other cell types (Couraud et al., J. Biol. Chem. 264:1310–1316 (1989). Galectin 1 is thought to specifically bind laminin, a highly polylactosaminated cellular glycoprotein, as well as the highly polylactosaminated lysosome-associated membrane proteins (LAMPs). Galectin 1 has also been shown to bind specifically to a lactosamine-containing glycolipid found on olfactory neurons and to integrin $a_7b_1$ on skeletal muscle cells.

Other members of the Galectin family have also been reported. Galectin 2 was originally found in hepatoma and is a homodimer with a subunit molecular mass of 14,650 Daltons (Gitt et al., J. Biol. Chem. 267:10601–10606 (1992)). Galectin 3 (a.k.a., Mac-2, EPB, CBP-35, CBP-30, and L-29) is abundant in activated macrophages and epithelial cells and is a monomer with an apparent molecular mass between 26,320 and 30,300 Daltons (Cherayil et al., Proc. Natl. Acad. Sci. USA 87: 7324–7326 (1990)). Galectin 3 has been observed to bind specifically to laminin, immunoglobulin E and its receptor, and bacterial lipopolysaccharides. Galectin 4 has a molecular mass of 36,300 Daltons and contains two carbohydrate-binding domains within a single polypeptide chain (Oda et al., J. Biol. Chem. 268:5929–5939 (1993)). Galectins 5 and 6 are discussed in Barondes et al., Cell 76:597–598 (1994). Human Galectin 7 has a molecular mass of 15,073 Daltons and is found mainly in stratified squamous epithelium (Madsen et al., J. Biol. Chem. 270 (11):5823–5829 (1995)).

Animal lectins, in general, often function in modulating cell-cell and cell-matrix interactions. Galectin 1 has been shown to either promote or inhibit cell adhesion depending upon the cell type in which it is present. Galectin 1 inhibits cell-matrix interactions in skeletal muscle presumably, by galectin 1-mediated disruption of laminin-integrin $a_7b_1$ interactions (Cooper et al., J. Cell Biol. 115:1437–1448 (1991)). In several non-skeletal muscle cell types, Galectin 1 promotes cell-matrix adhesion possibly by cross-linking cell surface and substrate glycoconjugates (Zhou et al., Arch. Bioch. Biophys. 300:6–17 (1993); Skrincosky et al., Cancer Res. 53:2667–2675 (1993)).

Galectin 1 also participates in regulating cell proliferation (Wells et al., Cell 64:91–97 (1991)) and some immune functions (Offner et al., J. Neuroimmunol. 28:177–184 (1990)). Galectin 1 induces the release of tumor necrosis factor from macrophages (Kajikawa et al., Life Sci. 39:1177–1181 (1986). Galectin 1 has also been demonstrated to have therapeutic activity against autoimmune diseases in animal models for experimental myasthenia gravis, and experimental autoimmune encephalomyelitis (Levi et al., Eur. J. Immunol. 13:500–507 (1983); and Offner et al., J. Neuroimmunol. 28:177–184 (1990), respectively). Additionally, galectin 1 has been shown to regulate immune response by mediating apoptosis of T cells (Perillo et al., Nature 378:736–739 (1995)).

Galectin 3 promotes the growth of cells cultured under restrictive culture conditions (Yang et al., Proc. Natl. Acad. Sci. USA 93:6737–6742 (June 1996)). Galectin 3 expression in cells confers resistance to apoptosis which indicates that galectin 3 could be a cell death suppresser which interferes in a common pathway of apoptosis. Id. Galectin 3 has also been observed to function in modulating cell-adhesion, as well as in the activation of certain immune cells by cross-linking IgE and IgE receptors.

Recently, a galectin-like antigen designated HOM-HD-21 was found to be highly expressed in a Hodgkin's Disease cDNA library and another galectin, termed PCTA-1, was identified as a specific cell surface marker on human prostate cancer cell lines and patient-derived carcinomas.

Thus, galectins have been observed to be involved in the regulation of immune cell activity, as well as in such diverse processes as cell adhesion, proliferation, inflammation, autoimmunity, and metastasis of tumor cells. Accordingly, there is a need in the art for the identification of novel galectins which can serve as useful tools in the development of therapeutics and diagnostics for regulating immune response, inflammatory disease and cancer.

SUMMARY OF THE INVENTION

The present invention provides isolated nucleic acid molecules comprising, or alternatively consisting of, a polynucleotide encoding the galectin 11 polypeptide having the amino acid sequence shown in FIG. 1 (SEQ ID NO:2), the amino acid sequence encoded by the cDNA clone deposited in a bacterial host as ATCC Deposit Number 209053, on May 16, 1997, and fragments, variants, derivatives, and analogs thereof.

The present invention also provides isolated nucleic acid molecules comprising a polynucleotide encoding the galectin 11 polypeptide having the amino acid sequence shown in FIGS. 6A–B (SEQ ID NO:14), referred to herein sometimes as "Galectin-11α" and fragments, variants, derivatives, and analogs thereof.

The present invention also provides isolated nucleic acid molecules comprising a polynucleotide encoding the galectin 11 polypeptide having the amino acid sequence shown in FIGS. 6A–B and 8 (SEQ ID NO:16), referred to herein sometimes as "Galectin-11β", and fragments, variants, derivatives, and analogs thereof.

The galectin 11 of FIG. 1 (SEQ ID NOS:1 and 2), the galectin 11α of FIGS. 6A–B (SEQ ID NOS:24 and 25), and the galectin 11β of FIGS. 7–8 (SEQ ID NOS:26 and 27) are often referred to herein collectively as, e.g., "galectin 11."

The galectin 11 polynucleotide of FIG. 1 (SEQ ID NO:1), the galectin 11α polynucleotide of FIGS. 6A–B (SEQ ID NO:24), and the galectin 11β polynucleotide of FIG. 7 (SEQ ID NO:26) are often referred to herein collectively as, e.g., "galectin 11 polynucleotides."

The present invention also relates to recombinant vectors which include the isolated nucleic acid molecules of the invention, and to host cells containing the recombinant vectors, as well as to methods of making such vectors and host cells and for using them for production of galectin 11 polypeptides by recombinant techniques.

The invention further provides isolated galectin 11 polypeptides, including galectin 11 of SEQ ID NO:2 and galectin 11α and β, having an amino acid sequence encoded by a polynucleotide described herein and antibodies which bind these polypeptides. The galectin 11 polypeptide of FIG. 1 (SEQ ID NO:2), the galectin 11α polypeptide of FIGS. 6A–B (SEQ ID NO:25), and the galectin 11β polypeptide of FIG. 7 (SEQ ID NO:27) are often referred to herein collectively as, e.g., "galectin 11 polypeptides."

The present invention also provides screening methods for identifying compounds capable of enhancing or inhibiting a cellular response, such as, for example, apoptosis, induced by galectin 11. Generally, these methods involve contacting galectin 11, the candidate compound, and a cell which expresses a galectin 11 ligand, assaying a cellular response resulting from the binding of galectin 11 with the ligand, and comparing the cellular response to a standard, the standard being assayed when contact of galectin 11 and the galectin 11 ligand is made in the absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on galectin 11 binding to a β-galactoside sugar. In particular, the method involves contacting a β-galactoside sugar with a galectin 11 polypeptide and a candidate compound and determining whether galectin 11 binding to the β-galactoside sugar is increased or decreased due to the presence of the candidate compound.

The invention also provides diagnostic methods useful during diagnosis of disorders associated with elevated, decreased, or otherwise aberrant expression of galectin 11.

The invention further provides for methods for treating an individual in need of an increased level of galectin 11 activity in the body comprising, administering to such an individual a composition comprising a therapeutically effective amount of an isolated galectin 11 polypeptide, fragment, variant, derivative, or analog of the invention, or an agonist thereof.

In another embodiment, the invention provides for methods for treating an individual in need of a decreased level of galectin 11 activity in the body comprising, administering to such an individual a composition comprising a therapeutically effective amount of a galectin 11 fragment, variant, derivative, analog or antibody of the invention or galectin 11 antagonist.

BRIEF DESCRIPTION OF THE FIGURES

FIG. 1 shows the nucleotide sequence (SEQ ID NO:1) and deduced amino acid sequence (SEQ ID NO:2) of galectin 11. The protein has a deduced molecular mass of about 14.8 kDa. The complementary strand of the nucleotide sequence of SEQ ID NO:1 is shown in SEQ ID NO:12.

FIG. 2 shows the regions of similarity between the amino acid sequences of the galectin 11 protein (HJACE54) (SEQ ID NO:2), rat galectin 5 (SEQ ID NO:3), and human galectin 8 (SEQ ID NO:4). Identical amino acids shared between the galectins are shaded, while conservative amino acid changes are boxed. By examining the regions of amino acids shaded and/or boxed, the skilled artisan can readily identify conserved domains between the two polypeptides. These conserved domains are preferred embodiments of the present invention.

Figure 3:
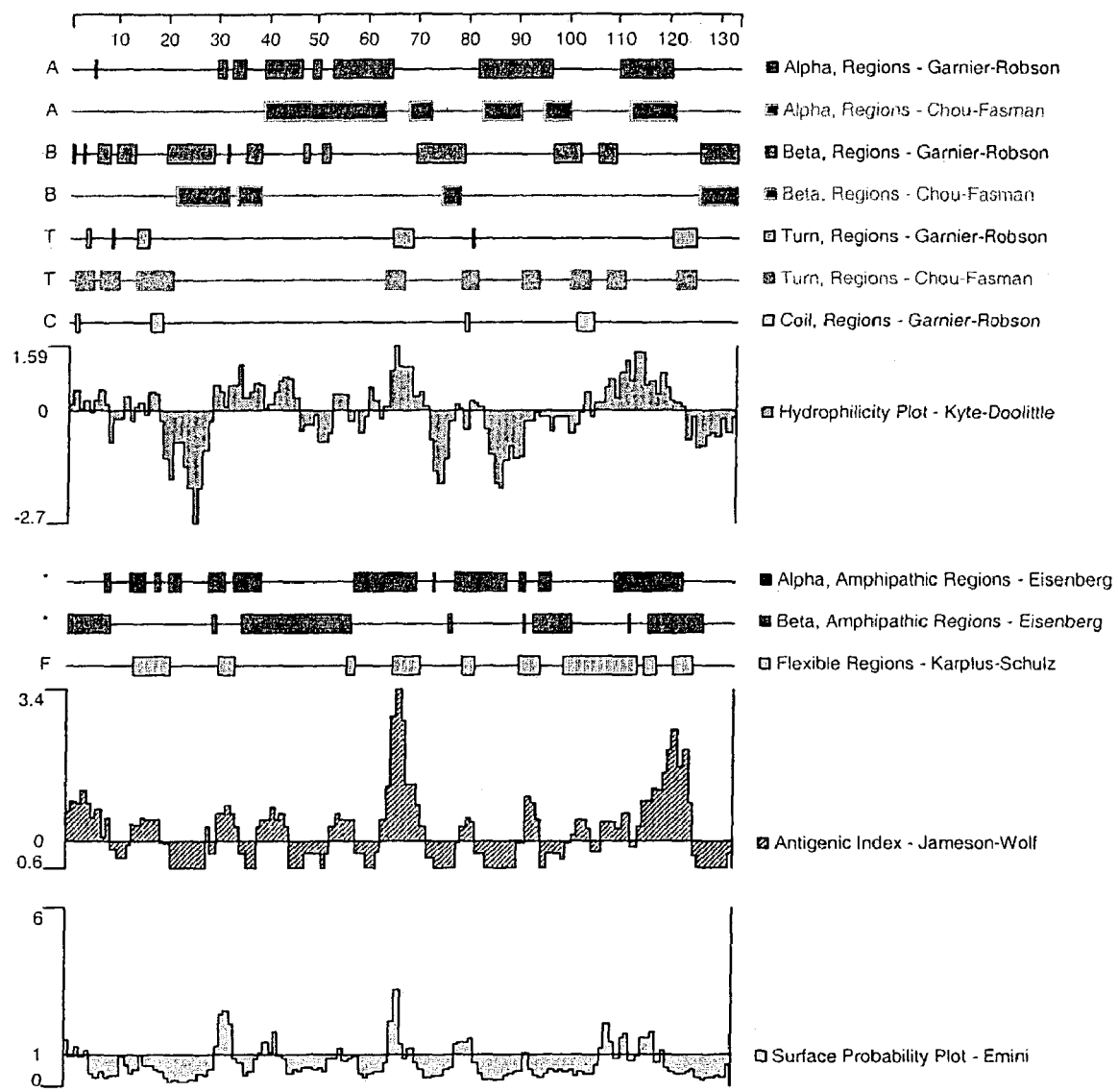
FIG. 3 shows structural and functional features of galectin 11 (SEQ ID NO:2) predicted using the default parameters of the indicated computer programs. Alpha, beta, turn and coil regions; hydrophilicity and hydrophobicity; amphipathic regions; flexible regions; antigenic index and surface probability are shown. In the Antigenic Index—Jameson-Wolf graph, the positive peaks indicate locations of the highly antigenic regions of the galectin 11 protein, i.e., regions from which epitope-bearing peptides of the invention can be obtained. The domains defined by these graphs are contemplated by the present invention, including for example, amino acid residues 65–70 and 118–124 in FIG. 1 (SEQ ID NO:2), which correspond to the shown highly antigenic regions of the galectin 11 polypeptide.

The data presented in FIG. 3 are also represented in tabular form in Table I. The columns are labeled with the headings "Res", "Position", and Roman Numerals I–XIII. The column headings refer to the following features of the amino acid sequence presented in FIG. 3, and Table I: "Res": amino acid residue of SEQ ID NO:2 and FIG. 1; "Position": position of the corresponding residue within SEQ ID NO:2 and FIGS. 1; I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Alpha, Amphipathic Regions—Eisenberg; X: Beta, Amphipathic Regions—Eisenberg; XI: Flexible Regions—Karplus-Schulz; XII: Antigenic Index—Jameson-Wolf; and XIII: Surface Probability Plot—Emini.

Figure 4:
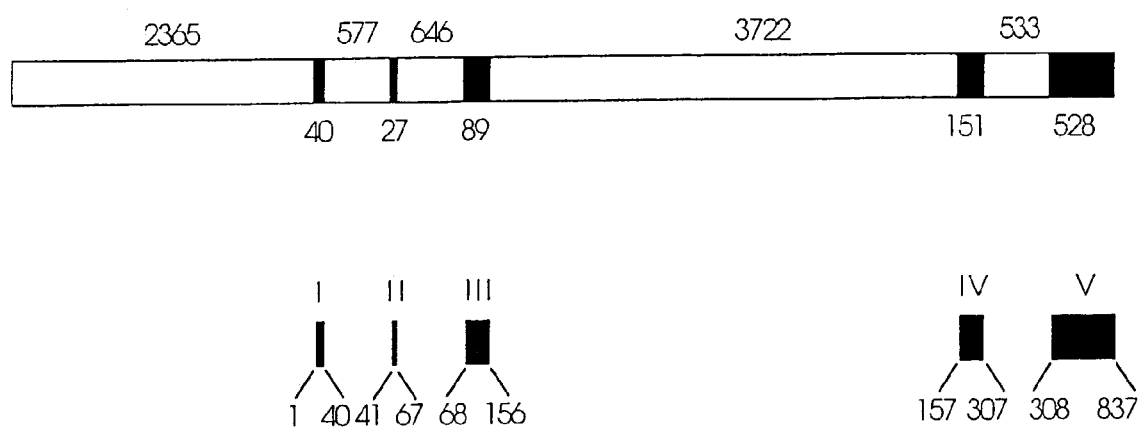

FIG. 4. Structure of human galectin 11 gene. The human galectin 11 gene is located on chromosome 11. This figure shows the structure of the region of chromosome 11 containing the galectin 11 gene and discloses the number of nucleotides corresponding to the transcribed (shaded) and untranscribed (open) portions of this region of the chromosome. The human galectin 11 gene contains 5 exons. The translation initiation site is located on the second exon. The nucleotide numbering identified in exons designated by roman numerals correspond to that presented in FIG. 1 (SEQ ID NO:1).

Figure 5A:
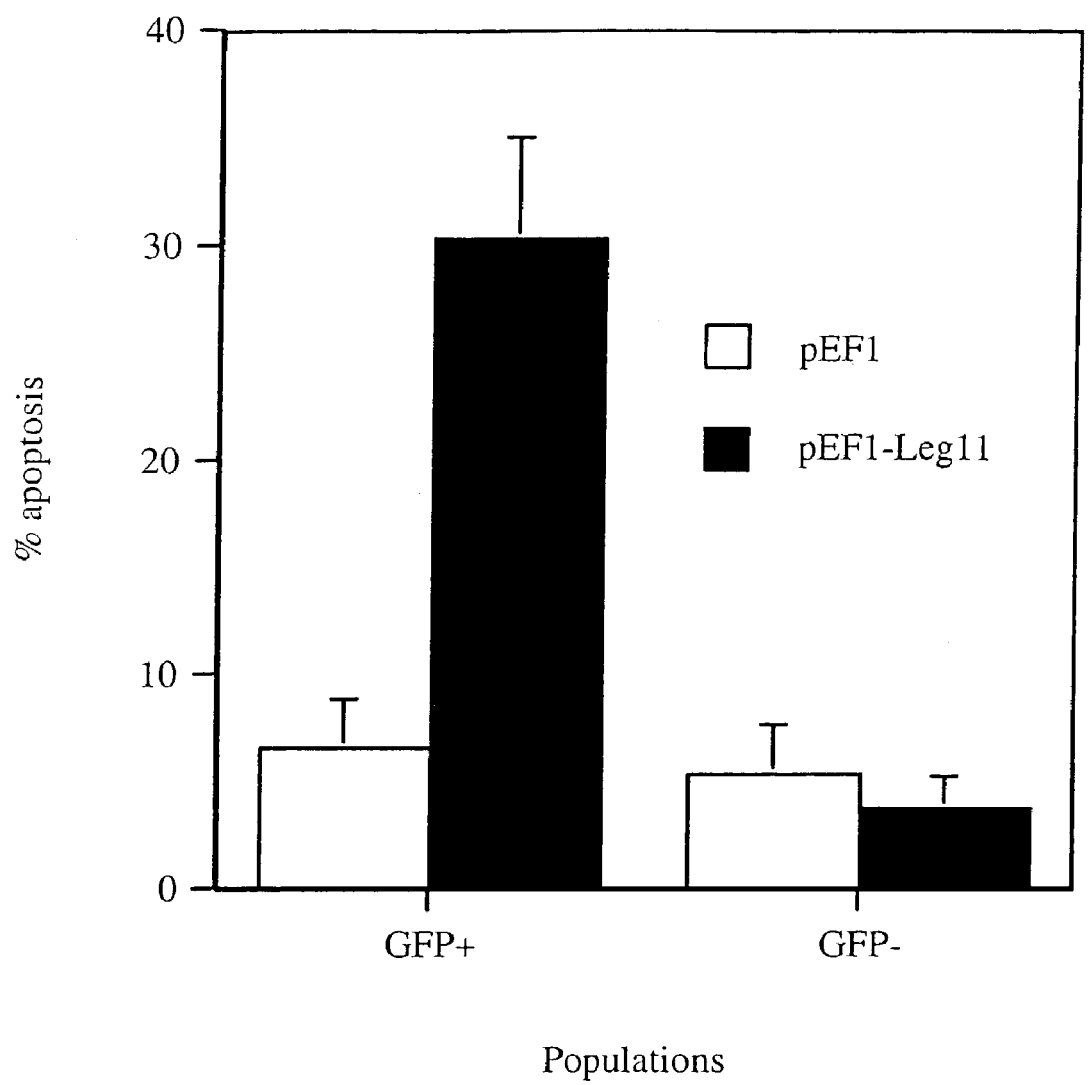

FIG. 5A is a bar graph showing that transfection of Jurkat cells with a galectin 11 expression construct (pEF-Leg11) induces apoptosis of transfected cells. Shaded bars represent % apoptosis of Jurkat cells that have been transfected with the galectin 11 expression construct, whereas open bars represent % apoptosis of Jurkat cells that have been transfected with the pEF control vector. Apoptosis was measured by two-color cytometry using mitoTracker Red.

Figure 5B:
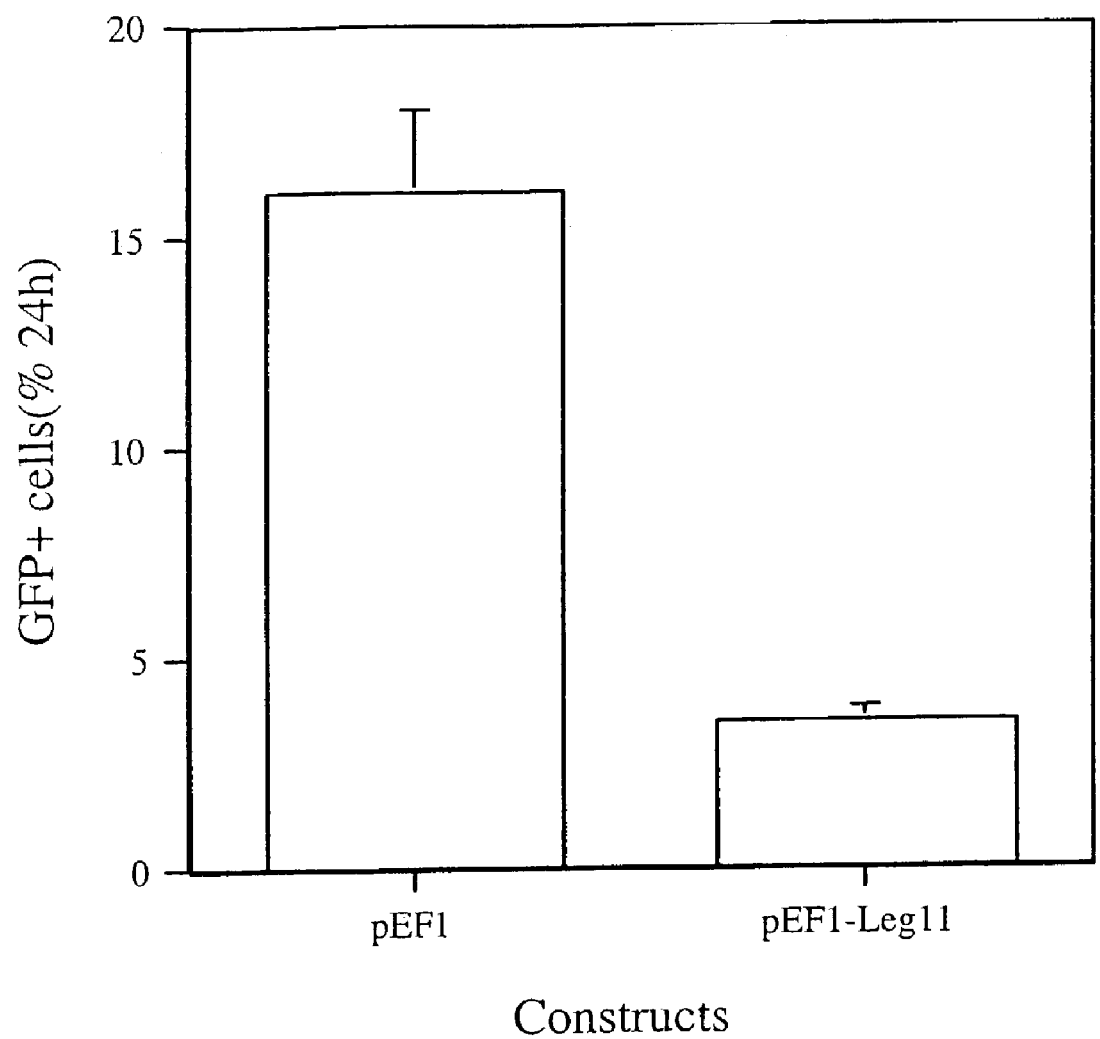

FIG. 5B is a bar graph showing the survival of GFP positive cells that have been successfully transfected, 4 days after transfection. The survival of the transfected cells was examined after co-transfection with either the control vector (pEF1), or the galectin 11 expression vector (pEF-Leg11). There were about 4 times more surviving GFP positive cells after transfection with pEF1 than with pEF-Leg11.

FIGS. 6A–B shows the nucleotide sequence (SEQ ID NO:24) and deduced amino acid sequence (SEQ ID NO:25) of the complete galectin 11α cDNA and protein, respectively.

Figure 7:
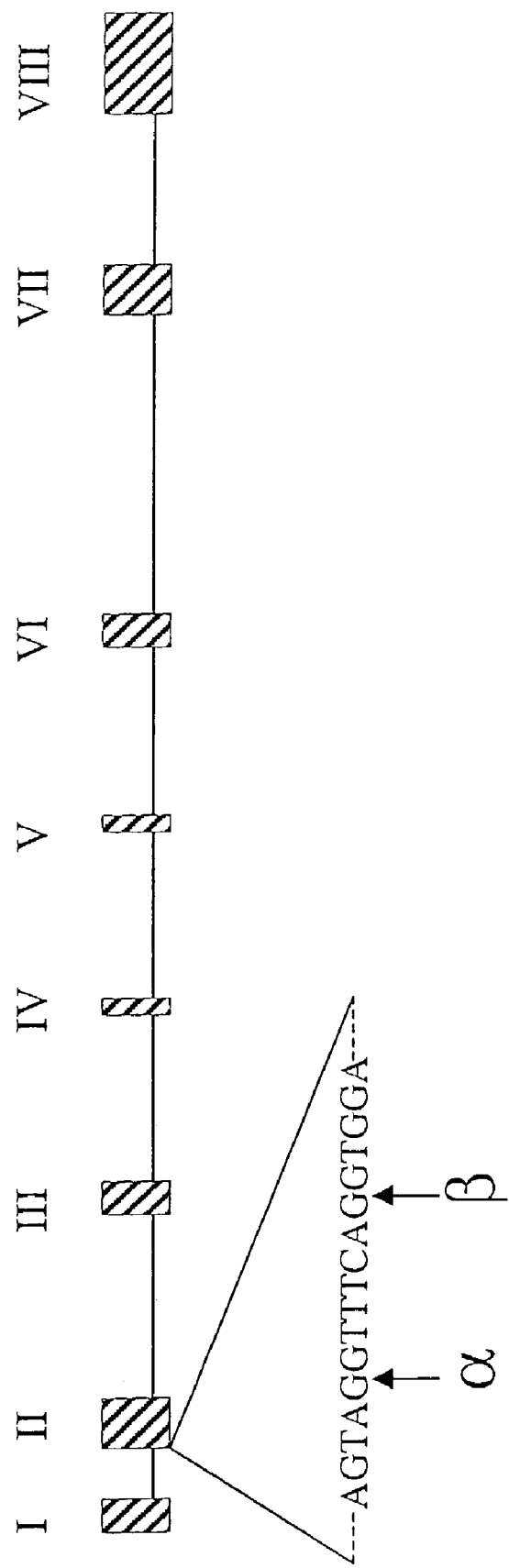

FIG. 7 is a schematic showing the relative positions of the 8 exons which comprise the galectin-11 gene. Also shown is the difference created by alternative splicing between galectin-11α and galectin-11β (galectin-11α being 7 nucleotides longer at the 5' terminus of exon 2) resulting in divergent N-termini between the variants. Nucleotide residues 136–147 of SEQ ID NO:24 (galectin-11α) and nucleotide residues 136–140 of SEQ ID NO:26 (galectin-11β) are shown.

FIG. 8 shows the difference between the polypeptide sequences of galectin-11α and galectin-11β. The complete nucleotide and amino acid sequences of galectin-11β are shown in the sequence listing as SEQ ID NOS: 26 and 27, respectively. Amino acid residues 1–29 of SEQ ID NO:25 (galectin-11α) and amino acid residues 1–50 of SEQ ID NO:27 (galectin-11β) are shown.

DETAILED DESCRIPTION

The present invention provides isolated nucleic acid molecules comprising a polynucleotide encoding a galectin 11 polypeptide having the amino acid sequence shown in FIG. 1 (SEQ ID NO:2), FIGS. 6A–B (SEQ ID NO:25), or FIGS. 6A–B and 8 (SEQ ID NO:27) which were determined by sequencing cloned cDNAs. The nucleotide sequence shown in FIG. 1 (SEQ ID NO:1) was obtained by sequencing the HJACE54 plasmid which was deposited on May 16, 1997 at the American Type Culture Collection, 10801 University Boulevard, Manassas, Va., and given accession number 209053. The galectin 11 polypeptides of the present invention share sequence homology with rat galectin 5, chicken galectin 3, and human galectin 8 gene products (see, e.g., FIG. 2; SEQ ID NOS:3–4).

The invention further provides for fragments, variants, derivatives and analogs of galectin 11 polynucleotides and polypeptides encoded thereby, and antibodies which bind these polypeptides.

Definitions

The following definitions are provided to facilitate understanding of certain terms used frequently herein.

"Functional activity" or "biological activity" refers to galectin 11 polypeptides, fragments, derivatives, variants, and analogs, exhibiting activity similar, but not necessarily identical to, an activity of a galectin 11 polypeptide, including mature forms, as measured in a particular biological assay, with or without dose dependency. In the case where dose dependency does exist, it need not be identical to that of the galectin 11 polypeptide, but rather substantially similar to the dose-dependence in a given activity as compared to the galectin 11 polypeptide (i.e., the candidate polypeptide will exhibit greater activity or not more than about 25-fold less and, preferably, not more than about tenfold less activity, and most preferably, not more than about three-fold less activity relative to the galectin 11 polypeptide.) Such functional activities include, but are not limited to, biological activity (such as, for example, the ability to bind a β-galactoside sugar, the ability to agglutinate trypsin-treated rabbit erythrocytes and/or to induce apoptosis), antigenicity (ability to bind or compete with a galectin 11 polypeptide for binding to an anti-galectin 11 antibody), immunogenicity (ability to generate antibody which binds to a galectin 11 polypeptide), the ability to form dimers with galectin 11 polypeptides of the invention, and the ability to bind to other galectins and/or a receptor or ligand for galectin 11. Polynucleotides encoding polypeptides having galectin 11 functional or biological activity, and the complementary strand of these polynucleotides are also encompassed by the invention.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given galectin 11 polypeptide. Also, a given galectin 11 polypeptide may contain many types of modifications. Galectin 11 polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", Meth Enzymol 182:626–646 (1990) and Rattan et al., "Protein Synthesis: Posttranslational Modifications and Aging", Ann NY Acad Sci 663:48–62 (1992)).

"Variant" as the term is used herein, is a polynucleotide or polypeptide that differs from a reference polynucleotide or polypeptide respectively, but retains functional or biological activity of galectin 11. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Antibodies" as used herein includes polyclonal and monoclonal antibodies, chimeric, single chain, and humanized antibodies, as well as Fab fragments, including the products of an Fab or other immunoglobulin expression library.

Nucleic Acid Molecules

The galectin 11 nucleotide sequence identified as SEQ ID NO:1 was assembled from partially homologous ("overlapping") sequences obtained from the deposited clone. The overlapping sequences were assembled into a single contiguous sequence of high redundancy resulting in a final sequence identified as SEQ ID NO:1.

Therefore, SEQ ID NO:1 and the translated SEQ ID NO:2 are sufficiently accurate and otherwise suitable for a variety of uses well known in the art and described further below. For instance, SEQ ID NO:1 is useful for designing nucleic acid hybridization probes that will detect nucleic acid sequences contained in SEQ ID NO:1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used, for example, to generate antibodies which bind specifically to proteins galectin 11.

Further, unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a human cDNA of galectin 11 deposited with the ATCC. The nucleotide sequence of the deposited galectin 11 clone can readily be determined by sequencing the deposited clone in accordance with known methods. The predicted galectin 11 amino acid sequence can then be verified from such deposits. Moreover, the amino acid sequence of the protein encoded by the deposited clone can also be directly determined by peptide sequencing or by expressing the protein in a suitable host cell containing the deposited human galectin 11 cDNA, collecting the protein, and determining its sequence.

Using the information provided herein, such as the nucleotide sequence in FIG. 1, a nucleic acid molecule of the present invention encoding a galectin 11 polypeptide may be obtained using standard cloning and screening procedures, such as those for cloning cDNAs using mRNA as starting material. Illustrative of the invention, the nucleic acid molecule described in FIG. 1 (SEQ ID NO:1) was discovered in a cDNA library derived from G1 phase Jurkat T-cells. This gene was also identified in cDNA libraries generated from human neutrophil and human infant adrenal gland. Polynucleotides of the invention can also be obtained from natural sources such as mRNA or genomic DNA using techniques known in the art, or can be chemically synthesized using techniques known in the art.

The human galectin 11 gene is located on chromosome 11 and contains 5 exons (see, e.g., FIG. 4). The nucleotide sequence of the galectin 11 cDNA of FIG. 1 (SEQ ID NO:1) is 865 nucleotides in length (830 nucleotides discounting the poly A tail of the cDNA) which encodes a predicted open reading frame of 133 amino acid residues. There is a predicted initiation codon at nucleotides 49–51 of the nucleotide sequence depicted in FIG. 1 (SEQ ID NO:1), located on the second exon of the gene. The galectin 11 protein shown in FIG. 1 (SEQ ID NO:2) shares homology with the translation product of rat galectin 5, chicken galectin 3, and human galectin 8 (see, e.g., FIG. 2). Additionally, as further discussed below, galectin 11 induces apoptosis of transfected T-cells (see Example 5 and FIGS. 5A and 5B). These findings indicate that galectin 11 functions in a manner similar to other previously characterized galectins and therefore, that galectin 11 is important in the regulation of cell growth disorders, autoimmune diseases, cancer, and inflammatory diseases.

The nucleotide sequence of the galectin 11 cDNA of FIGS. 6A–B (SEQ ID NO:24) is 1337 nucleotides in length. This is one of two alternatively spliced forms of galectin 11 and is referred to as galectin 11α. The other form, galectin 11β, differs only in the loss of 7 nucleotides (nucleotides 136–142 as shown in FIGS. 6A–B (SEQ ID NO:24)). See FIG. 7. The sequence of galectin 11β is shown in the sequence listing as SEQ ID NO:26. The resulting translation products of these splice variants are believed to differ only at the N-terminus. The amino acid sequences of galectin 11α and β are shown in the sequence listing as SEQ ID NOS:25 and 27, respectively. The differences between the two proteins are highlighted in FIG. 8.

The galectin 11 polypeptide is comprised of two carbohydrate binding domains (CARD domains) separated by a linker sequence. The first carbohydrate binding domain consists of the first 121 amino acid residues of galectin-11α (SEQ ID NO:25) and the first 142 amino acids of galectin 11β (SEQ ID NO:27). The 29 amino acid residues following the first CARD domain is the linker sequence. Finally, the last 125 amino acid residues in each protein is the C-terminal CARD domain. Preferred polypeptides of the invention comprise either an N-terminal or C-terminal CARD domain. Polynucleotides encoding such polypeptides are also provided.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to SEQ ID NO:1–2, 24–25, 26–27, or the deposited clone, using information from the sequences disclosed herein or the clones deposited with the ATCC. For example, allelic variants and/or species homologs may be isolated and identified by making suitable probes or primers from the sequences provided herein and screening a suitable nucleic acid source for allelic variants and/or the desired homologue.

As one of ordinary skill would appreciate, due to the possibilities of sequencing errors discussed above, as well as the variability of processing sites for different known proteins, the predicted galectin 11 polypeptide encoded by the deposited cDNA comprises about 133 amino acid residues, but may be anywhere in the range of 125–150 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the complementary or anti-sense strand.

By "isolated" nucleic acid molecule(s) is intended a nucleic acid molecule, DNA or RNA, which has been removed from its native environment (e.g., the natural environment if it is naturally occurring), and thus is altered "by the hand of man" from its natural state. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. In a specific embodiment, "isolated" nucleic acid molecules of the invention comprise all or a portion of the coding region of galectin 11, as disclosed in FIG. 1 (SEQ ID NO:1) or galectin 11α as disclosed in FIGS. 6A–B (SEQ ID NO:24), or galectin 11β as disclosed in SEQ ID NO:26. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

Isolated nucleic acid molecules of the present invention include DNA molecules comprising an open reading frame (ORF) or a portion of an ORF shown in FIG. 1 or 6A–B (SEQ ID NO:1, 24, or 26); and DNA molecules which comprise a sequence substantially different from those described above, but which due to the degeneracy of the genetic code, still encode the galectin 11 protein. Of course, the genetic code is well known in the art. Thus, it would be routine for one skilled in the art to generate such degenerate variants.

In specific embodiments, the invention provides isolated nucleic acid molecules encoding the full length galectin 11 polypeptide depicted in FIG. 1 (SEQ ID NO:2), and galectin 11 nucleic acid molecules encoding the galectin 11 polypeptide sequence encoded by the cDNA clone contained in the plasmid deposited as ATCC Deposit No. 209053, on May 16, 1997. In a further embodiment, nucleic acid molecules are provided encoding the full length galectin 11 polypeptide lacking the N-terminal methionine. The invention further provides an isolated nucleic acid molecule having the nucleotide sequence shown in FIG. 1 (SEQ ID NO:1) or the nucleotide sequence of the galectin 11 cDNA contained in the above-described deposited clone, or a nucleic acid molecule having a sequence complementary to one of the above sequences. Such isolated molecules, particularly DNA molecules, have uses which include, but are not limited to, probes for gene mapping by in situ hybridization with chromosomes, and for detecting expression of the galectin 11 gene in human tissue, for instance, by Northern blot analysis. The invention further provides a polynucleotide encoding a polypeptide comprising the full-length amino acid sequence shown as SEQ ID NO:25 or 27, with or without an N-terminal methoinine.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the galectin 11 gene of interest on chromosome II). In other embodiments, the polynucleotides of the invention do not contain the coding sequence of more than 1000, 500, 250, 100, 50, 25, 20, 15, 10, 5, 4, 3, 2, or 1 genomic flanking gene(s).

The present invention is further directed to fragments of the isolated nucleic acid molecules described herein. By a fragment of an isolated nucleic acid molecule having the nucleotide sequence of the deposited cDNA, the nucleotide sequence shown in FIGS. 1 and 6A–B (SEQ ID NOS:1, 24, and 26), or the complementary strand thereto, is intended fragments of at least about 15 nt, and more preferably at least about 20 nt, still more preferably at least about 30 nt, and even more preferably, at least about 40 nt in length. By a fragment at least 20 nt in length, for example, is intended fragments which include 20 or more contiguous bases from the nucleotide sequence of the deposited cDNA or the nucleotide sequence as shown in FIG. 1 (SEQ ID NO:1) or the cDNA shown in FIG. 6 (SEQ ID NOS:24 and 26) or the complementary strand thereto. Also encompassed by the invention are DNA fragments comprising 50, 100, 150, 200, 250, 300, 350, 365, 370, 375, 380, 400, 450, 500, 550, 600, 650, 700, 750, 800, 850 contiguous nucleotides of the sequence shown in FIG. 1 (SEQ ID NO:1), the strand complementary thereto, or contained in the deposited clone. The present invention also encompasses fragments corresponding to most, if not all, of the nucleotide sequence of the deposited cDNA or as shown in FIG. 1 (SEQ ID NO:1) or the complimentary strand thereto. In further embodiments, the polynucleotide fragments of the invention comprise a sequence which encodes amino acids 1–14, 1–20, 1–40, 1–66, 2–67, 3–8, 3–67, 5–108, 5–128, 10–17, 10–20, 12–16, 13–20, 13–68, 14–67, 23–40, 20–50, 40–108, 41–60, 47–61, 47–108, 47–128, 50–100, 61–80, 65–108, 65–128, 66–108, 76–88, 81–100, 88–108, 88–128, 95–101, 101–133, 108–120, 114–128, and/or 114–128 of the amino acid sequence depicted in FIG. 1 (SEQ ID NO:2). In preferred embodiments, polynucleotide fragments of the invention encode a polypeptide which demonstrates a galectin 11 functional activity. Fragments of the invention have numerous uses which include, but are not limited to, diagnostic probes and primers as discussed herein.

Preferred nucleic acid fragments of the present invention include nucleic acid molecules encoding epitope-bearing portions of the galectin 11 protein. In particular, such nucleic acid fragments of the present invention include nucleic acid molecules encoding: a polypeptide comprising amino acid residues from about 65–70 and 118–124 in FIG. 1 (SEQ ID NO:2). The inventors have determined that the above polypeptide fragments are antigenic regions of the galectin 11 protein. Methods for determining other such epitope-bearing portions of the galectin 11 protein are described in detail below.

In other embodiments, the invention provides an isolated nucleic acid molecule comprising, or alternatively consisting of, a polynucleotide which hybridizes under stringent hybridization conditions to all or a portion of a galectin 11 polynucleotides (including fragments) described herein, the complementary strand thereof, the cDNA clone contained in ATCC Deposit No. 209053, on May 16, 1997, or fragments thereof. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at 65° C.

Also contemplated are nucleic acid molecules that hybridize to the galectin 11 polynucleotides under lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M $NaH_2PO_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

By a polynucleotide which hybridizes to a portion of a polynucleotide is intended a polynucleotide (either DNA or RNA) hybridizing to at least about 15 nucleotides (nt), and more preferably at least about 20, still more preferably at least about 30, 50, 60, 75, 100, 150, 175, 200, 250, 300, 350 nt preferable about 30–70 nt, or 80–150 nucleotides, or the entire length of the reference polynucleotide. By a portion of a polynucleotide of at least "20 nt in length", for example, is intended 20 or more contiguous nucleotides from the nucleotide sequence of the reference polynucleotide (e.g., the deposited cDNA or the nucleotide sequence as depicted in FIG. 1 (SEQ ID NO:1). In specific embodiments, the polynucleotide hybridizes to nucleotides 0–20, 0–25, 0–30, 0–50, 51–100, 80–100, 101–200, 201–300, 301–400, 401–450, 451–500, 501–550, 551–600, 601–700, 701–750, 751–780, and/or 780–820 of the nucleotide sequence disclosed in FIG. 1 (SEQ ID NO:1). In other specific embodiments, the polynucleotide hybridizes to a nucleotide sequence which encodes amino acid residues 1–14, 10–20, 20–50, 50–100, 100–133 of the amino acid sequence depicted in FIG. 1 (SEQ ID NO:2). In specific embodiments, the polynucleotide hybridizes to nucleotides 1–20, 1–25, 1–30, 1–50, 51–100, 80–100, 101–200, 201–300, 301–400, 401–450, 451–500, 501–550, 551–600, 601–700, 701–750, 751–800, 801–850, 851–900, 901–950, 951–1,000, 1,001–1050, 1,051–1,100, 1,101–1,150, 1,151–1,200, 1,201–1,250, and/or 1,251–1,337 of the nucleotide sequence disclosed in SEQ ID NO:24. In other specific embodiments, the polynucleotide hybridizes to a nucleotide sequence which encodes amino acid residues 1–14, 10–20, 20–50, 50–100, 100–130, 130–160, 160–210, 210–240 and/or 240–275 of the amino acid sequence depicted in SEQ ID NO:25. In specific embodiments, the polynucleotide hybridizes to nucleotides 1–20, 1–25, 1–30, 1–50, 51–100, 80–100, 101–200, 201–300, 301–400, 401–450, 451–500, 501–550, 551–600, 601–700, 701–750, 751–800, 801–850, 851–900, 901–950, 951–1,000, 1,001–1050, 1,051–1,100, 1,101–1, 150, 1,151–1,200, 1,201–1,250, and/or 1,251–1,330 of the nucleotide sequence disclosed in Figure SEQ ID NO:26. In other specific embodiments, the polynucleotide hybridizes to a nucleotide sequence which encodes amino acid residues 1–14, 10–20, 20–50, 50–100, 100–130, 130–160, 160–210, 210–240, 240–270 and/or 270–296 of the amino acid sequence depicted in SEQ ID NO:27. These polynucleotides have uses which include, but are not limited to, diagnostic probes and primers, as discussed above and in more detail below.

Of course, a polynucleotide which hybridizes only to a poly A sequence (such as the 3' terminal poly(A) tract of the galectin 11 cDNA shown in FIG. 1 (SEQ ID NO:1), FIGS. 6A–B (SEQ ID NO:24) or SEQ ID NO:26 or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using an oligo-dT primer).

As indicated, nucleic acid molecules of the present invention which encode a galectin 11 polypeptide may include, but are not limited to, those encoding the amino acid sequence of the polypeptide, by itself; the coding sequence for the polypeptide and additional sequences, such as those encoding an amino acid leader or secretory sequence, such as a pre-, or pro- or prepro-protein sequence; the coding sequence of the polypeptide, with or without the aforementioned additional coding sequences, together with additional, non-coding sequences, including for example, but not limited to, introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., Proc. Natl. Acad. Sci. USA 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., Cell 37:767–778 (1984). As discussed below, other such fusion proteins include the galectin 11 fused to Fc at the N- or C-terminus.

The present invention is also directed to polynucleotide fragments of the polynucleotides of the invention. In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1, 24, or 26 or the complementary strand thereto, or is a portion of a polynucleotide sequence encoding the polypeptide of SEQ ID NO:2, 25, or 27. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1, 24, or 26. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–48, 49–99, 100–150, 151–201, 202–252, 253–303, 304–354, 355–405, 406–450, 451–501, and 502 to the end of SEQ ID NO:1, or the complementary strand thereto, or the cDNA contained in the deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides.

The exact formulation, route of administration and dosage of the compounds of the invention to be administrated can be chosen by the individual physician in view of the patient's condition (see e.g., Fingl et al., 1975, in "The Pharmacological Basis of Therapeutics." Ch. 1 p. 1). Other methods will be known to the skilled artisan and are within the scope of the invention.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides comprising a nucleotide sequence described by the general formula of a–b, where a is any integer between 1 to 851 of SEQ ID NO:1, b is an integer of 15 to 865, where both a and b correspond to the positions of nucleotide residues shown in SEQ ID NO:1, and where the b is greater than or equal to a+14.

The present invention further relates to variants of the nucleic acid molecules of the present invention, which encode a portion (i.e., fragments), analogs or derivatives of the galectin 11 protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions which may involve one or more nucleotides Particularly preferred are variants in which the nucleotide sequence encoding 1, 2, 3, 4, 5, 6, 7, 8, 9, 10, 11, 12, 13, 14 15, 20, 25, 30, 35, 40, 50, or, 20–15, 15–10, 10–5 1–5, 1–3, or 1–2 amino acids of a polypeptide of the invention are substituted, deleted, or added in any combination. The variants may be altered in coding regions, non-coding regions, or both. Alterations in the coding regions may produce conservative or non-conservative amino acid substitutions, deletions or additions. Especially preferred among these are silent substitutions, additions and deletion, which do not alter the properties and activities of the galectin 11 protein or portions thereof. Also especially preferred in this regard are conservative substitutions.

Further embodiments of the invention include isolated nucleic acid molecules comprising a polynucleotide having a nucleotide sequence at least 75%, 80%, 85%, or 90% identical, and more preferably at least 95%, 96%, 97%, 98% or 99% or 98–99% identical to (a) a nucleotide encoding amino acids 1 to 133 of SEQ ID NO:2; (b) a nucleotide encoding amino acids 2 to 133 of SEQ ID NO:2; (c) a nucleotide sequence of the galectin 11 polypeptide encoded by the cDNA contained in ATCC Deposit No. 209053; (d) a nucleotide encoding amino acids 1 to 275 of SEQ ID NO:25; (e) a nucleotide encoding amino acids 1 to 296 of SEQ ID NO:27; (f) a nucleotide encoding amino acid residues 1 to 121 of SEQ ID NO:25; (g) a nucleotide encoding amino acid residues 1 to 142 of SEQ ID NO:27; (h) a nucleotide encoding amino acids 2 to 275 of SEQ ID NO:25; (i) a nucleotide encoding amino acid residues 2 to 296 of SEQ ID NO:27; (j) a nucleotide encoding amino acids 151 to 275 of SEQ ID NO:25; or (k) fragments and other polynucleotide sequences of the invention as described herein. Polynucleotides which hybridize to these nucleic acid molecules under stringent hybridization conditions or lower stringency conditions are also encompassed by the invention, as are polypeptides encoded by these polynucleotides.

By a polynucleotide having a nucleotide sequence at least, for example, 95% "identical" to a reference nucleotide sequence encoding a galectin 11 polypeptide of the present invention is intended that the nucleotide sequence of the polynucleotide is identical to the reference sequence except that the polynucleotide sequence may include up to five nucleotide mismatches per each 100 nucleotides of the reference nucleotide sequence encoding the galectin 11 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The query sequence may be an entire sequence shown of SEQ ID NO:1, the ORF (open reading frame), or any fragment specified as described herein.

As a practical matter, whether any particular nucleic acid molecule is at least 75%, 80%, 85%, 90%, 92%, 95%, 96%, 97%, 98% or 99% identical to, for instance, the nucleotide sequence shown in SEQ ID NOS:1, 24, and 26 or to the nucleotides sequence of the deposited cDNA clone can be determined conventionally using known computer programs, such as, for example, the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

A preferred method for determining the best overall match between a query sequence (a sequence of the present invention) and a subject sequence, also referred to as a global sequence alignment, is determined using the FASTDB computer program based on the algorithm of Brutlag et al. (Comp. App. Biosci. 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identify are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The galectin 11 variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Galectin 11 polynucleotide variants can be produced for a variety of reasons, e.g., to optimize codon expression for a particular host (change codons in the human mRNA to those preferred by a bacterial host such as *E. coli*).

Naturally occurring galectin 11 variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the galectin 11 polypeptides. For instance, one or more amino acids can be deleted from the N-terminus or C-terminus of the secreted protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein. (Dobeli et al., J. Biotechnology 7:199–216 (1988).)

Moreover, ample evidence demonstrates that variants often retain a biological activity similar to that of the naturally occurring protein. For example, Gayle and coworkers (J. Biol. Chem 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See, Abstract.) In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the secreted form will likely be retained when less than the majority of the residues of the secreted form are removed from the N-terminus or C-terminus. Whether a particular polypeptide lacking N- or C-terminal residues of a protein retains such immunogenic activities can readily be determined by routine methods described herein and otherwise known in the art.

Thus, the invention further includes galectin 11 polypeptide variants which show substantial biological activity. Such variants include deletions, insertions, inversions, repeats, and substitutions selected according to general rules known in the art so as have little effect on activity.

The present application is directed to nucleic acid molecules at least 75%, 80%, 85%, 90%, 92%, 95%, 96%, 97%, 98% or 99% identical to the nucleic acid sequences disclosed herein (e.g., nucleic acid sequence shown in FIG. 1 or 6A–B (SEQ ID NO:1, 24, or 26), nucleic acid sequence of the deposited cDNA clone, and nucleic acid sequences encoding a polypeptide having the amino acid sequence of an N and/or C terminal deletion disclosed below as m–n of SEQ ID NO:2, 25, or 27), irrespective of whether they encode a polypeptide having galectin 11 functional activity. This is because even where a particular nucleic acid molecule does not encode a polypeptide having galectin 11 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having galectin 11 functional activity include, inter alia, (1) isolating the galectin 11 gene or allelic or splice variants thereof in a cDNA library; (2) in situ hybridization (e.g., "FISH") to metaphase chromosomal spreads to provide precise chromosomal location of the galectin 11 gene, as described in Verma et al., *Human Chromosomes: A Manual of Basic Techniques*, Pergamon Press, New York (1988); (3) use in linkage analysis as a marker for chromosome 11; and (4) Northern Blot analysis for detecting galectin 11 mRNA expression in specific tissues.

Preferred, however, are nucleic acid molecules having sequences at least 75%, 80%, 85%, 90%, 92%, 95%, 96%, 97%, 98% or 99% identical to the nucleic acid sequence disclosed herein, shown in FIG. 1 or 6A–B (SEQ ID NO:1, 24, or 26), nucleic acid sequence of the deposited cDNA clone, the nucleic acid encoding the polypeptide shown in FIG. 1 or 6A–B (SEQ ID NO:2, 25, or 27), and fragments thereof, which do, in fact, encode a polypeptide having galectin 11 functional activity. By "a polypeptide having galectin 11 functional activity" is intended polypeptides exhibiting activity similar, but not necessarily identical, to a functional activity of the galectin 11 protein of the invention (e.g., complete (full-length) galectin 11, and mature galectin 11), as measured in a particular assay. For example, galectin 11 protein activity can be measured using a β-galactoside sugar (e.g., thiodigalactoside or lactose) binding assay, an assay for apoptosis and/or an assay for agglutination of trypsin-treated rabbit erythrocytes, as further described below.

Of course, due to the degeneracy of the genetic code, one of ordinary skill in the art will immediately recognize that a large number of the nucleic acid molecules having a sequence at least 75%, 80%, 85%, 90%, 92%, 95%, 96%, 97%, 98%, or 99% identical to the nucleic acid sequence of the deposited cDNA, the nucleic acid sequence shown in FIG. 1 or 6A–B (SEQ ID NO:1, 24, or 26), the nucleic acid encoding the polypeptide shown in FIG. 1 or 6A–B (SEQ ID NO:2, 25, or 27), or fragment thereof, will encode "a polypeptide having galectin 11 functional activity". In fact, since numerous degenerate variants of these nucleotide sequences encode the same polypeptide, this will be clear to the skilled artisan even without performing the above described comparison assay. It will be further recognized in the art that, for such nucleic acid molecules that are not degenerate variants, a reasonable number will also encode a polypeptide having galectin 11 activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., Deciphering the Message in Protein Sequences: Tolerance to Amino Acid Substitutions, Science 247:1306–1310 (1990), wherein the authors indicate that proteins are surprisingly tolerant of amino acid substitutions.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989)). The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val; Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For example, site directed changes at the amino acid level of galectin 11 of FIG. 1 (SEQ ID NO:2) can be made by replacing a particular amino acid with a conservative amino acid. Preferred conservative mutations include: M1 replaced with A, G, I, L, S, T, or V; S2 replaced with A, G, I, L, T, M, or V; R4 replaced with H, or K; L5 replaced with A, G, I, S, T, M, or V; E6 replaced with D; V7 replaced with A, G, I, L, S, T, or M; S10 replaced with A, G, I, L, T, M, or V; H11 replaced with K, or R; A12 replaced with G, I, L, S, T, M, or V; L13 replaced with A, G, I, S, T, M, or V; Q15 replaced with N; G16 replaced with A, I, L, S, T, M, or V; L17 replaced with A, G, I, S, T, M, or V; S18 replaced with A, G, I, L, T, M, or V; G20 replaced with A, I, L, S, T, M, or V; Q21 replaced with N; V22 replaced with A, G, I, L, S, T, or M; I23 replaced with A, G, L, S, T, M, or V; I24 replaced with A, G, L, S, T, M, or V; V25 replaced with A, G, I, L, S, T, or M; R26 replaced with H, or K; G27 replaced with A, I, L, S, T, M, or V; L28 replaced with A, G, I, S, T, M, or V; V29 replaced with A, G, I, L, S, T, or M; L30 replaced with A, G, I, S, T, M, or V; Q31 replaced with N; E32 replaced with D; K34 replaced with H, or R; H35 replaced with K, or R; F36 replaced with W, or Y; T37 replaced with A, G, I, L, S, M, or V; V38 replaced with A, G, I, L, S, T, or M; S39 replaced with A, G, I, L, T, M, or V; L40 replaced with A, G, I, S, T, M, or V; R41 replaced with H, or K; D42 replaced with E; Q43 replaced with N; A44 replaced with G, I, L, S, T, M, or V; A45 replaced with G, I, L, S, T, M, or V; H46 replaced with K, or R; A47 replaced with G, I, L, S, T, M, or V; V49 replaced with A, G, I, L, S, T, or M; T50 replaced with A, G, I, L, S, M, or V; L51 replaced with A, G, I, S, T, M, or V; R52 replaced with H, or K; A53 replaced with G, I, L, S, T, M, or V; S54 replaced with A, G, I, L, T, M, or V; F55 replaced with W, or Y; A56 replaced with G, I, L, S, T, M, or V; D57 replaced with E; R58 replaced with H, or K; T59 replaced with A, G, I, L, S, M, or V; L60 replaced with A, G, I, S, T, M, or V; A61 replaced with G, I, L, S, T, M, or V; W62 replaced with F, or Y; I63 replaced with A, G, L, S, T, M, or V; S64 replaced with A, G, I, L, T, M, or V; R65 replaced with H, or K; W66 replaced with F, or Y; G67 replaced with A, I, L, S, T, M, or V; Q68 replaced with N; K69 replaced with H, or R; K70 replaced with H, or R; L71 replaced with A, G, I, S, T, M, or V; I72 replaced with A, G, L, S, T, M, or V; S73 replaced with A, G, I, L, T, M, or V; A74 replaced with G, I, L, S, T, M, or V; F76 replaced with W, or Y; L77 replaced with A, G, I, S, T, M, or V; F78 replaced with W, or Y; Y79 replaced with F, or W; Q81 replaced with N; R82 replaced with H, or K; F83 replaced with W, or Y; F84 replaced with W, or Y; E85 replaced with D; V86 replaced with A, G, I, L, S, T, or M; L87 replaced with A, G, I, S, T, M, or V; L88 replaced with A, G, I, S, T, M, or V; L89 replaced with A, G, I, S, T, M, or V; F90 replaced with W, or Y; Q91 replaced with N; E92 replaced with D; G93 replaced with A, I, L, S, T, M, or V; G94 replaced with A, I, L, S, T, M, or V; L95 replaced with A, G, I, S, T, M, or V; K96 replaced with H, or R; L97 replaced with A, G, I, S, T, M, or V; A98 replaced with G, I, L, S, T, M, or V; L99 replaced with A, G, I, S, T, M, or V; N100 replaced with Q; G101 replaced with A, I, L, S, T, M, or V; Q102 replaced with N; G103 replaced with A, I, L, S, T, M, or V; L104 replaced with A, G, I, S, T, M, or V; G105 replaced with A, I, L, S, T, M, or V; A106 replaced with G, I, L, S, T, M, or V; T107 replaced with A, G, I, L, S, M, or V; S108 replaced with A, G, I, L, T, M, or V; M109 replaced with A, G. 1, L, S, T, or V; N110 replaced with Q; Q111 replaced with N; Q112 replaced with N; A113 replaced with G, I, L, S, T, M, or V; L114 replaced with A, G, I, S, T, M, or V; E115 replaced with D; Q116 replaced with N; L117 replaced with A, G, I, S, T, M, or V; R118 replaced with H, or K; E119 replaced with D; L120 replaced with A, G, I, S, T, M, or V; R121 replaced with H, or K; I122 replaced with A, G, L, S, T, M, or V; S123 replaced with A, G, I, L, T, M, or V; G124 replaced with A, I, L, S, T, M, or V; S125 replaced with A, G, I, L, T, M, or V; V126 replaced with A, G, I, L, S, T, or M; Q127 replaced with N; L128 replaced with A, G, I, S, T, M, or V; Y129 replaced with F, or W; V131 replaced with A, G, I, L, S, T, or M; H132 replaced with K, or R; and/or S133 replaced with A, G, I, L, T, M, or V.

Using these same principles, similar conservative substitutions can be made in the polypeptide of SEQ ID NO:25 or 27.

The resulting constructs can be routinely screened for activities or functions described throughout the specification and known in the art. Preferably, the resulting constructs have an increased and/or a decreased galectin 11 activity or function, while the remaining galectin 11 activities or functions are maintained. More preferably, the resulting constructs have more than one increased and/or decreased galectin 11 activity or function, while the remaining galectin 11 activities or functions are maintained.

Besides conservative amino acid substitution, variants of galectin 11 include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, galectin 11 polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

For example, preferred non-conservative substitutions of galectin 11 of FIG. 1 (SEQ ID NO:2) include: M1 replaced with D, E, H, K, R, N, Q, F, W, Y, P, or C; S2 replaced with D, E, H, K, R, N, Q, F, W, Y, P, or C; P3 replaced with D, E, H, K, R, A, G, I, L, S, T, M, V, N, Q, F, W, Y, or C; R4 replaced with D, E, A, G, I, L, S, T, M, V, N, Q, F, W, Y, P, or C; L5 replaced with D, E, H, K, R, N, Q, F, W, Y, P, or C; E6 replaced with H, K, R, A, G, I, L, S, T, M, V, N, Q, F, W, Y, P, or C; V7 replaced with D, E, H, K, R, N, Q, F, W, Y, P, or C; P8 replaced with D, E, H, K, R, A, G, I, L, S, T, M, V, N, Q, F, W, Y, or C; C9 replaced with D, E, H, K, R, A, G, I, L, S, T, M, V, N, Q, F, W, Y, or P; S10 replaced with D, E, H, K, R, N, Q, F, W, Y, P, or C; H11 replaced with D, E, A, G, I, L, S, T, M, V, N, Q, F, W, Y, P, or C; A12 replaced with D, E, H, K, R, N, Q, F, W, Y, P, or C; L13 replaced with D, E, H, K, R, N, Q, F, W, Y, P, or C; P14 replaced with D, E, H, K, R, A, G, I, L, S, T, M, V, N, Q, F, W, Y, or C; Q15 replaced with D, E, H, K, R, A, G, I, L, S, T, M, V, F, W, Y, P, or C; G16 replaced with D, E, H, K, R, N, Q, F, W, Y, P, or C; L17 replaced with D, E, H, K, R, N, Q, F, W, Y, P, or C; S18 replaced with D, E, H, K, R, N, Q, F, W, Y, P, or C; P19 replaced with D, E, H, K, R, A, G, I, L, S, T, M, V, N, Q, F, W, Y,or C; G20 replaced with D, E, H, K, R, N, Q, F, W, Y, P, or C; Q21 replaced with D, E, H, K, R, A, G, I, L, S, T, M, V, F, W, Y, P, or C; V22 replaced with D, E, H, K, R, N, Q, F, W, Y, P, or C; I23 replaced with D, E, H, K, R, N, Q, F, W, Y, P, or C; I24 replaced with D, E, H, K, R, N, Q, F, W, Y, P, or C; V25 replaced with D, E, H, K, R, N, Q, F, W, Y, P, or C; R26 replaced with D, E, A, G, I, L, S, T, M, V, N, Q, F, W, Y, P, or C; G27 replaced with D, E, H, K, R, N, Q, F, W, Y, P, or C; L28 replaced with D, E, H, K, R, N, Q, F, W, Y, P, or C; V29 replaced with D, E, H, K, R, N, Q, F, W, Y, P, or C; L30 replaced with D, E, H, K, R, N, Q, F, W, Y, P, or C; Q31 replaced with D, E, H, K, R, A, G, I, L, S, T, M, V, F, W, Y, P, or C; E32 replaced with H, K, R, A, G, I, L, S, T, M, V, N, Q, F, W, Y, P, or C; P33 replaced with D, E, H, K, R, A, G, I, L, S, T, M, V, N, Q, F, W, Y, or C; K34 replaced with D, E, A, G, I, L, S, T, M, V, N, Q, F, W, Y, P, or C; H35 replaced with D, E, A, G, I, L, S, T, M, V, N, Q, F, W, Y, P, or C; F36 replaced with D, E, H, K, R, N, Q, A, G, I, L, S, T, M, V, P, or C; T37 replaced with D, E, H, K, R, N, Q, F, W, Y, P, or C; V38 replaced with D, E, H, K, R, N, Q, F, W, Y, P, or C; S39 replaced with D, E, H, K, R, N, Q, F, W, Y, P, or C; L40 replaced with D, E, H, K, R, N, Q, F, W, Y, P, or C; R41 replaced with D, E, A, G, I, L, S, T, M, V, N, Q, F, W, Y, P, or C; D42 replaced with H, K, R, A, G, I, L, S, T, M, V, N, Q, F, W, Y, P, or C; Q43 replaced with D, E, H, K, R, A, G, I, L, S, T, M, V, F, W, Y, P, or C; A44 replaced with D, E, H, K, R, N, Q, F, W, Y, P, or C; A45 replaced with D, E, H, K, R, N, Q, F, W, Y, P, or C; H46 replaced with D, E, A, G, I, L, S, T, M, V, N, Q, F, W, Y, P, or C; A47 replaced with D, E, H, K, R, N, Q, F, W, Y, P, or C; P48 replaced with D, E, H, K, R, A, G, I, L, S, T, M, V, N, Q, F, W, Y, or C; V49 replaced with D, E, H, K, R, N, Q, F, W, Y, P, or C; T50 replaced with D, E, H, K, R, N, Q, F, W, Y, P, or C; L51 replaced with D, E, H, K, R, N, Q, F, W, Y, P, or C; R52 replaced with D, E, A, G, I, L, S, T, M, V, N, Q, F, W, Y, P, or C; A53 replaced with D, E, H, K, R, N, Q, F, W, Y, P, or C; S54 replaced with D, E, H, K, R, N, Q, F, W, Y, P, or C; F55 replaced with D, E, H, K, R, N, Q, A, G, I, L, S, T, M, V, P, or C; A56 replaced with D, E, H, K, R, N, Q, F, W, Y, P, or C; D57 replaced with H, K, R, A, G, I, L, S, T, M, V, N, Q, F, W, Y, P, or C; R58 replaced with D, E, A, G, I, L, S, T, M, V, N, Q, F, W, Y, P, or C; T59 replaced with D, E, H, K, R, N, Q, F, W, Y, P, or C; L60 replaced with D, E, H, K, R, N, Q, F, W, Y, P, or C; A61 replaced with D, E, H, K, R, N, Q, F, W, Y, P, or C; W62 replaced with D, E, H, K, R, N, Q, A, G, I, L, S, T, M, V, P, or C; I63 replaced with D, E, H, K, R, N, Q, F, W, Y, P, or C; S64 replaced with D, E, H, K, R, N, Q, F, W, Y, P, or C; R65 replaced with D, E, A, G, I, L, S, T, M, V, N, Q, F, W, Y, P, or C; W66 replaced with D, E, H, K, R, N, Q, A, G, I, L, S, T, M, V, P, or C; G67 replaced with D, E, H, K, R, N, Q, F, W, Y, P, or C; Q68 replaced with D, E, H, K, R, A, G, I, L, S, T, M, V, F, W, Y, P, or C; K69 replaced with D, E, A, G, I, L, S, T, M, V, N, Q, F, W, Y, P, or C; K70 replaced with D, E, A, G, I, L, S, T, M, V, N, Q, F, W, Y, P, or C; L71 replaced with D, E, H, K, R, N, Q, F, W, Y, P, or C; I72 replaced with D, E, H, K, R, N, Q, F, W, Y, P, or C; S73 replaced with D, E, H, K, R, N, Q, F, W, Y, P, or C; A74 replaced with D, E, H, K, R, N, Q, F, W, Y, P, or C; P75 replaced with D, E, H, K, R, A, G, I, L, S, T, M, V, N, Q, F, W, Y, or C; F76 replaced with D, E, H, K, R, N, Q, A, G, I, L, S, T, M, V, P, or C; L77 replaced with D, E, H, K, R, N, Q, F, W, Y, P, or C; F78 replaced with D, E, H, K, R, N, Q, A, G, I, L, S, T, M, V, P, or C; Y79 replaced with D, E, H, K, R, N, Q, A, G, I, L, S, T, M, V, P, or C; P80 replaced with D, E, H, K, R, A, G, I, L, S, T, M, V, N, Q, F, W, Y, or C; Q81 replaced with D, E, H, K, R, A, G, I, L, S, T, M, V, F, W, Y, P, or C; R82 replaced with D, E, A, G, I, L, S, T, M, V, N, Q, F, W, Y, P, or C; F83 replaced with D, E, H, K, R, N, Q, A, G, I, L, S, T, M, V, P, or C; F84 replaced with D, E, H, K, R, N, Q, A, G, I, L, S, T, M, V, P, or C; E85 replaced with H, K, R, A, G, I, L, S, T, M, V, N, Q, F, W, Y, P, or C; V86 replaced with D, E, H, K, R, N, Q, F, W, Y, P, or C; L87 replaced with D, E, H, K, R, N, Q, F, W, Y, P, or C; L88 replaced with D, E, H, K, R, N, Q, F, W, Y, P, or C; L89 replaced with D, E, H, K, R, N, Q, F, W, Y, P, or C; F90 replaced with D, E, H, K, R, N, Q, A, G, I, L, S, T, M, V, P, or C; Q91 replaced with D, E, H, K, R, A, G, I, L, S, T, M, V, F, W, Y, P, or C; E92 replaced with H, K, R, A, G, I, L, S, T, M, V, N, Q, F, W, Y, P, or C; G93 replaced with D, E, H, K, R, N, Q, F, W, Y, P,or ,C; G94 replaced with D, E, H, K, R, N, Q, F, W, Y, P, or C; L95 replaced with D, E, H, K, R, N, Q, F, W, Y, P, or C; K96 replaced with D, E, A, G, I, L, S, T, M, V, N, Q, F, W, Y, P, or C; L97 replaced with D, E, H, K, R, N, Q, F, W, Y, P, or C; A98 replaced with D, E, H, K, R, N, Q, F, W, Y, P, or C; L99 replaced with D, E, H, K, R, N, Q, F, W, Y, P, or C; N100 replaced with D, E, H, K, R, A, G, I, L, S, T, M, V, F, W, Y, P, or C; G101 replaced with D, E, H, K, R, N, Q, F, W, Y, P, or C; Q102 replaced with D, E, H, K, R, A, G, I, L, S, T, M, V, F, W, Y, P, or C; G103 replaced with D, E, H, K, R, N, Q, F, W, Y, P, or C; L104 replaced with D, E, H, K, R, N, Q, F, W, Y, P, or C; G105 replaced with D, E, H, K, R, N, Q, F, W, Y, P, or C; A106 replaced with D, E, H, K, R, N, Q, F, W, Y, P, or C; T107 replaced with D, E, H, K, R, N, Q, F, W, Y, P, or C; S108 replaced with D, E, H, K, R, N, Q, F, W, Y, P, or C; M109 replaced with D, E, H, K, R, N, Q, F, W, Y, P, or C; N110 replaced with D, E, H, K, R, A, G, I, L, S, T, M, V, F, W, Y, P, or C; Q111 replaced with D, E, H, K, R, A, G, I, L, S, T, M, V, F, W, Y, P, or C; Q112 replaced with D, E, H, K, R, A, G, I, L, S, T, M, V, F, W, Y, P, or C; A113 replaced with D, E, H, K, R, N, Q, F, W, Y, P, or C; L114 replaced with D, E, H, K, R, N, Q, F, W, Y, P, or C; E115 replaced with H, K, R, A, G, I, L, S, T, M, V, N, Q, F, W, Y, P, or C; Q116 replaced with D, E, H, K, R, A, G, I, L, S, T, M, V, F, W, Y, P, orC; L117 replaced with D, E, H, K, R, N, Q, F, W, Y, P, or C; R118 replaced with D, E, A, G, I, L, S, T, M, V, N, Q, F, W, Y, P, or C; E119 replaced with H, K, R, A, G, I, L, S, T, M, V, N, Q, F, W, Y, P, or C; L120 replaced with D, E, H, K, R, N, Q, F, W, Y, P, or C; R121 replaced with D, E, A, G, I, L, S, T, M, V, N, Q, F, W, Y, P, or C; I122 replaced with D, E, H, K, R, N, Q, F, W, Y, P, or C; S123 replaced with D, E, H, K, R, N, Q, F, W, Y, P, or C; G124 replaced with D, E, H, K, R, N, Q, F, W, Y, P, or C; S125 replaced with D, E, H, K, R, N, Q, F, W, Y, P, or C; V126 replaced with D, E, H, K, R, N, Q, F, W, Y, P, or C; Q127 replaced with D, E, H, K, R, A, G, I, L, S, T, M, V, F, W, Y, P, or C; L128 replaced with D, E, H, K, R, N, Q, F, W, Y, P, or C; Y129 replaced with D, E, H, K, R, N, Q, A, G, I, L, S, T, M, V, P, or C; C130 replaced with D, E, H, K, R, A, G, I, L, S, T, M, V, N, Q, F, W, Y, or P; V131 replaced with D, E, H, K, R, N, Q, F, W, Y, P, or C; H132 replaced with D, E, A, G, I, L, S, T, M, V, N, Q, F, W, Y, P, or C; and S133 replaced with D, E, H, K, R, N, Q, F, W, Y, P, or C. Using these same principles, similar non-conservative substitutions can be made in the polypeptide of SEQ ID NO:25 or 27.

The resulting constructs can be routinely screened for activities or functions described throughout the specification and known in the art. Preferably, the resulting constructs have an increased and/or decreased galectin 11 activity or function, while the remaining galectin 11 activities or functions are maintained. More preferably, the resulting constructs have more than one increased and/or decreased galectin 11 activity or function, while the remaining galectin 11 activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of galectin 11 protein, as well as the N- and C-terminal deletion mutants, having the general formula m-n, [$m^1$-$n^1$, $m^1$-$n^2$, $m^1$-$n^3$, $m^2$-$n^1$, $m^2$-$n^2$, $m^2$-$n^3$, $m^3$-$n^1$, $m^3$-$n^2$ and $m^3$-$n^3$].

A further embodiment of the invention relates to a polypeptide which comprises the amino acid sequence of a galectin 11 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a galectin 11 polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of SEQ ID NOS: 2, 25, or 27 or fragments thereof (e.g., the mature form and/or other fragments described herein), is 1–5, 5–10, 5–25, 5–50, 10–50 or 50–150, conservative amino acid substitutions are preferable.

Vectors, Host Cells and Protein Production

The present invention also relates to vectors which include the isolated DNA molecules of the present invention, host cells which are genetically engineered with the polynucleotides and/or recombinant vectors of the invention, and the production of galectin 11 polypeptides and fragments, variants, derivatives, and analogs thereof, by recombinant techniques.

Galectin 11 polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the DNA of the invention is operatively associated with an appropriate heterologous regulatory element (e.g., promoter or enhancer), such as the phage lambda PL promoter, the *E. coli* lac, trp and tac promoters, the SV40 early and late promoters and promoters of retroviral LTRs, to name a few. Other suitable promoters and enhancers will be known to the skilled artisan.

In embodiments in which vectors contain expression constructs, these constructs will further contain sites for transcription initiation, termination and, in the transcribed region, a ribosome binding site for translation. The coding portion of the transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or G418 neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptococcus staphylococci, Bacillus subtilis, Streptomyces* and *Salmonella typhimurium* cells; fungal cells, such as yeast cells; insect cells such as *Drosophila* S2 and *Spodoptera* Sf9 cells; animal cells such as CHO, COS, HeLa, C127, 3T3, BHK, HEK293, and Bowes melanoma cells; and plant cells. Appropriate culture mediums and conditions for the above-described host cells are known in the art.

Selection of appropriate vectors and promoters for expression in a host cell is a well known procedure and the requisite techniques for expression vector construction, introduction of the vector into the host, and expression in the host are routine skills in the art. A great variety of expression vectors can be used to express galectin 11 polypeptides and fragments, variants, derivatives, and analogs of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used. The appropriate nucleotide sequence may be inserted into an expression vector system by any of a variety of known technique, such as for example, those set forth in Ausubel et al., eds., 1989, Current Protocols in Molecular Biology, Green Publishing Associates, Inc., and John Wiley & Sons, Inc., New York.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

The present invention also relates to host cells containing the vector constructs discussed herein, and additionally encompasses host cells containing nucleotide sequences of the invention that are operably associated with one or more heterologous control regions (e.g., promoters and/or enhancers) using techniques known in the art. As discussed above, the host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the foreign protein expressed.

For secretion of the translated protein into the lumen of the endoplasmic reticulum, into the periplasmic space or into the extracellular environment, appropriate secretion signals may be incorporated into the desired polypeptide using techniques known in the art. These signals may be endogenous to the polypeptide or they may be heterologous signals.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986). It is specifically contemplated that galectin 11 polypeptides may in fact be expressed by a host cell lacking a recombinant vector.

The polypeptide may be expressed in a modified form, such as a fusion protein (comprising the polypeptide joined via a peptide bond to a heterologous protein sequence (of a different protein)), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. Alternatively, such a fusion protein can be made by protein synthetic techniques, e.g., by use of a peptide synthesizer.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-has been fused with Fe portions for the purpose of high-throughput screening assays to identify antagonists of hIL-5. See, Bennett et al., J. Md. Recog. 8:52–58 (1995) and Johanson et al., J. Biol. Chem. 270(16):9459–9471 (1995).

The galectin 11 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, plant, insect, teleost, avian, and mammalian cells. Depending upon the host employed in a recombinant production procedure, the polypeptides of the present invention may be glycosylated or may be non-glycosylated. In addition, polypeptides of the invention may also include an initial modified methionine residue or may be missing an initial methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., galectin 11 coding sequence), and/or to include genetic material (e.g., heterologous polynucleotide sequences) that is operably associated with galectin 11 polynucleotides of the invention, and which activates, alters, and/or amplifies endogenous galectin 11 polynucleotides. For example, techniques known in the art may be used to operably associate heterologous control regions (e.g., promoter and/or enhancer) and endogenous galectin 11 polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105–111 (1984)). For example, a polypeptide corresponding to a fragment of a galectin 11 polypeptide can be synthesized by use of a peptide synthesizer. Furthermore, if desired, nonclassical amino acids or chemical amino acid analogs can be introduced as a substitution or addition into the galectin 11 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses galectin 11 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., Appl. Biochem. Biotechnol. 56:59–72 (1996); Vorobjev et al., Nucleosides Nucleotides 18:2745–2750 (1999); and Caliceti et al., Bioconjug. Chem. 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

The galectin 11 polypeptides of the invention may be in monomers or multimers (i.e., dimers, trimers, tetramers and higher multimers). Accordingly, the present invention relates to monomers and multimers of the galectin 11 polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2, or alternatively SEQ ID NO:25 or 27, or encoded by the cDNA contained in the deposited clone (including fragments, variants, splice variants, and fusion proteins, corresponding to these as described herein). These homomers may contain galectin 11 polypeptides having identical or different amino acid sequences. In a specific embodiment, a homomer of the invention is a multimer containing only galectin 11 polypeptides having an identical amino acid sequence. In another specific embodiment, a homomer of the invention is a multimer containing galectin 11 polypeptides having different amino acid sequences. In specific embodiments, the multimer of the invention is a homodimer (e.g., containing galectin 11 polypeptides having identical or different amino acid sequences) or a homotrimer (e.g., containing galectin 11 polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the galectin 11 polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the galectin 11 polypeptides of the invention. Such covalent associations may involve one or more amino acid residues contained in the polypeptide sequence (e.g., that recited in SEQ ID NO:2, 25, or 27, or contained in the polypeptide encoded by the clone HJACE54). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a galectin 11 fusion protein. In one example, covalent associations are between the heterologous sequence contained in a fusion protein of the invention (see, e.g., U.S. Pat. No. 5,478,925). In a specific example, the covalent associations are between the heterologous sequence contained in a galectin 11-Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In further preferred embodiments, Galectin 11 polynucleotides of the invention are fused to a polynucleotide encoding a "FLAG" polypeptide. Thus, a galectin 11-FLAG fusion protein is encompassed by the present invention. The FLAG antigenic polypeptide may be fused to an galectin 11 polypeptide of the invention at either or both the amino or the carboxy terminus. In preferred embodiments, a galectin 11-FLAG fusion protein is expressed from a pFLAG-CMV-5a or a pFLAG-CMV-1 expression vector (available from Sigma, St. Louis, Mo., USA). See, Andersson, S., et al., *J. Biol. Chem.* 264:8222–29 (1989); Thomsen, D. R., et al., *Proc. Natl. Acad. Sci. USA,* 81:659–63 (1984); and Kozak, M., *Nature* 308:241 (1984) (each of which is hereby incorporated by reference). In further preferred embodiments, a galectin 11-FLAG fusion protein is detectable by anti-FLAG monoclonal antibodies (also available from Sigma).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Galectin 11 Polypeptides and Fragments

The invention further provides an isolated galectin 11 polypeptide having the amino acid sequence encoded by the deposited cDNA, the amino acid sequence depicted in FIG. 1 (amino acid residues 1-133 of SEQ ID NO:2), the amino acid sequence depicted in FIG. 1 less the amino terminal methionine (amino acid residues 2-133 of SEQ ID NO:2), polypeptides which are encoded by a polynucleotide that hybridizes under stringent hybridization conditions to a polynucleotide sequence encoding a polypeptide having the amino acid sequence depicted in FIG. 1 (SEQ ID NO:2) and/or contained in the deposited clone, and fragments, variants, derivatives and analogs of these polypeptides.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the galectin 11 polypeptide can be substantially purified by the one-step method described in Smith and Johnson, Gene 67:31–40 (1988).

It will be recognized in the art that some amino acid sequences of the galectin 11 polypeptide can be varied without significant effect of the structure or function of the protein. If such differences in sequence are contemplated, it should be remembered that there will be critical areas on the protein which determine activity.

Thus, the invention further includes variations of the galectin 11 polypeptide which show substantial galectin 11 polypeptide functional activity or which include regions of galectin 11 protein such as the protein portions discussed below. Such mutants include deletions, insertions, inversions, repeats, and type substitutions.

As indicated above, guidance concerning which amino acid changes are likely to be phenotypically silent can be found in Bowie et al., Deciphering the Message in Protein Sequences: Tolerance to Amino Acid Substitutions, Science 247:1306–1310 (1990). Thus, a fragment, variant, derivative, or analog of the polypeptide of FIG. 1 or 6A–B (SEQ ID NO:2, 25, or 27), or that encoded by the deposited cDNA, include (i) one in which at least one or more of the amino acid residues are substituted with a conserved or non-conserved amino acid residue (preferably a conserved amino acid residue(s), and more preferably at least one but less than ten conserved amino acid residues) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, variants, derivatives and analogs are deemed to be within the scope of those skilled in the art from the teachings herein.

Of particular interest are substitutions of one or more charged amino acids with other charged amino acid and with neutral or negatively charged amino acids. The latter results in proteins with reduced positive charge to improve the characteristics of the galectin 11 protein. The prevention of aggregation is highly desirable. Aggregation of proteins not only results in a loss of activity but can also be problematic when preparing pharmaceutical formulations, because they can be immunogenic (Pinckard et al., Clin. Exp. Immunol. 2:331–340 (1967); Robbins et al., Diabetes 36:838–845 (1987); Cleland et al., Crit. Rev. Therapeutic Drug Carrier Systems 10:307–377 (1993)).

As indicated, changes are preferably of a minor nature, such as conservative amino acid substitutions that do not significantly affect the folding or activity of the protein (see Table 2).

TABLE 2

| Conservative Amino Acid Substitutions | |
| --- | --- |
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In the specific embodiments, the number of additions, substitutions and/or deletions in the amino acid sequence of FIG. 1 or 6A–B (SEQ ID NO:2, 25, or 27) and/or any of the polypeptide fragments described herein is 50, 40, 35, 30, 25, 20, 15, 14, 13, 12, 11, 10, 9, 8, 7, 6, 5, 4, 3, 2, or 1, or 15–20, 15–10, 5–10, 1–5, 1–3, or 1–2.

Amino acid residues of the galectin 11 polypeptide, fragment, variant, derivative, or analog of the present invention that are essential for function can be identified by methods known in the art, such as site-directed mutagenesis or alanine-scanning mutagenesis (Cunningham and Wells, Science 244:1081–1085 (1989)). The latter procedure introduces single alanine mutations at every residue in the molecule. The resulting mutant molecules are then tested for biological activity or functional activity, such as, receptor binding, β-galactoside (e.g., thiodigalactoside or lactose) binding, the ability to agglutinate trypsin-treated rabbit erythrocytes, or the ability in vitro or in vivo to induce apoptosis. Sites that are critical for ligand-receptor binding can also be determined by structural analysis such as crystallization, nuclear magnetic resonance or photoaffinity labeling (Smith et al., J. Mol. Biol. 224:899–904 (1992) and de Vos et al., Science 255:306–312 (1992)).

The present invention also encompasses polypeptides which are at least 75%, 80%, 85%, 90%, 92%, 95%, 96%, 97%, 98%, or 99%, or, 97–99% identical to the polypeptides described above. By a polypeptide having an amino acid sequence at least, for example, 95% "identical" to a reference amino acid sequence of a galectin 11 polypeptide is intended that the amino acid sequence of the polypeptide is identical to the reference sequence except that the polypeptide sequence may include up to five amino acid alterations per each 100 amino acids of the reference amino acid of the galectin 11 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 75%, 80%, 85%, 90%, 92%, 95%, 96%, 97%, 98% or 99% identical to, for instance, the amino acid sequence shown in FIG. 1 or 6A–B (SEQ ID NO:2, 25, or 27), the amino acid sequence encoded by deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention have uses which include, but are not limited to, molecular weight marker on SDS-PAGE gels or on molecular sieve gel filtration columns using methods well known to those of skill in the art.

The present invention also encompasses fragments of the above-described polypeptides of the invention. In specific embodiments, these fragments are at least 20, 25, 30, 40, 50, 75, 90, 100, 110, 120, 125, or 130 amino acid residues in length.

In the present invention, a "polypeptide fragment" refers to an amino acid sequence which is a portion of that contained in SEQ ID NO:2, 25, or 27 or encoded by the cDNA contained in the deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 101–120, or 121 to the end of the coding region. Moreover, polypeptide fragments can be about 20, 30, 40, 50, 60, 70, 80, 90, 100, 110, 120, or 130 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Even if deletion of one or more amino acids from the N-terminus of a protein results in modification of loss of one or more biological functions of the protein, other functional activities (e.g., biological activities, ability to multimerize, ability to bind galectin 11 ligand) may still be retained. For example, the ability of shortened galectin 11 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an galectin 11 mutein with a large number of deleted N-terminal amino acid residues may retain some biological or immunogenic activities. In fact, peptides composed of as few as six galectin 11 amino acid residues may often evoke an immune response.

Accordingly, polypeptide fragments include the secreted galectin 11 protein as well as the mature form. Further preferred polypeptide fragments include the secreted galectin 11 protein or the mature form having a continuous series of deleted residues from the amino or the carboxy terminus, or both. For example, any number of amino acids, ranging from 1–60, can be deleted from the amino terminus of either the secreted galectin 11 polypeptide or the mature form. Similarly, any number of amino acids, ranging from 1–30, can be deleted from the carboxy terminus of the secreted galectin 11 protein or mature form. Furthermore, any combination of the above amino and carboxy terminus deletions are preferred. Similarly, polynucleotides encoding these polypeptide fragments are also preferred.

In one embodiment, the present invention further provides polypeptides having one or more residues deleted from the amino terminus of the amino acid sequence of the galectin 11 polypeptide depicted in FIG. 1 or 6A–B (SEQ ID NO:2, 25, or 27) or encoded by the cDNA of the deposited clone. Particularly, in one embodiment, N-terminal deletions of the galectin 11 polypeptide can be described by the general formula m to 133, where m is a integer from 1 to 128 corresponding to the position of amino acid residue identified in SEQ ID NO:2 and preferably, corresponds to one of the N-terminal amino acid residues identified in the N-terminal deletions specified herein. In specific embodiments, N-terminal deletions of the galectin 11 polypeptide of the invention comprise, or alternatively consist of, amino acid residues: S-2 to S-133; P-3 to S-133; R-4 to S-133; L-5 to S-133; E-6 to S-133; V-7 to S-133; P-8 to S-133; C-9 to S-133; S-10 to S-133; H-11 to S-133; A-12 to S-133; L-13 to S-133; P-14 to S-133; Q-15 to S-133; G-16 to S-133; L-17 to S-133; S-18 to S-133; P-19 to S-133; G-20 to S-133; Q-21 to S-133; V-22 to S-133; I-23 to S-133; I-24 to S-133; V-25 to S-133; R-26 to S-133; G-27 to S-133; L-28 to S-133; V-29 to S-133; L-30 to S-133; Q-31 to S-133; E-32 to S-133; P-33 to S-133; K-34 to S-133; H-35 to S-133; F-36 to S-133; T-37 to S-133; V-38 to S-133; S-39 to S-133; L-40 to S-133; R-41 to S-133; D-42 to S-133; Q-43 to S-133; A-44 to S-133; A-45 to S-133; H-46 to S-133; A-47 to S-133; P-48 to S-133; V-49 to S-133; T-50 to S-133; L-51 to S-133; R-52 to S-133; A-53 to S-133; S-54 to S-133; F-55 to S-133; A-56 to S-133; D-57 to S-133; R-58 to S-133; T-59 to S-133; L-60 to S-133; A-61 to S-133; W-62 to S-133; I-63 to S-133; S-64 to S-133; R-65 to S-133; W-66 to S-133; G-67 to S-133; Q-68 to S-133; K-69 to S-133; K-70 to S-133; L-71 to S-133; 1–72 to S-133; S-73 to S-133; A-74 to S-133; P-75 to S-133; F-76 to S-133; L-77 to S-133; F-78 to S-133; Y-79 to S-133; P-80 to S-133; Q-81 to S-133; R-82 to S-133; F-83 to S-133; F-84 to S-133; E-85 to S-133; V-86 to S-133; L-87 to S-133; L-88 to S-133; L-89 to S-133; F-90 to S-133; Q-91 to S-133; E-92 to S-133; G-93 to S-133; G-94 to S-133; L-95 to S-133; K-96 to S-133; L-97 to S-133; A-98 to S-133; L-99 to S-133; N-100 to S-133; G-101 to S-133; Q-102 to S-133; G-103 to S-133; L-104 to S-133; G-105 to S-133; A-106 to S-133; T-107 to S-133; S-108 to S-133; M-109 to S-133; N-110 to S-133; Q-111 to S-133; Q-112 to S-133; A-113 to S-133; L-114 to S-133; E-115 to S-133; Q-116 to S-133; L-117 to S-133; R-118 to S-133; E-119 to S-133; L-120 to S-133; R-121 to S-133; I-122 to S-133; S-123 to S-133; G-124 to S-133; S-125 to S-133; V-126 to S-133; Q-127 to S-133; and L-128 to S-133 of SEQ ID NO:2. Polynucleotides encoding these polypeptides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind galectin 11 ligand) may still be retained. For example the ability of the shortened galectin 11 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an galectin 11 mutein with a large number of deleted C-terminal amino acid residues may retain some biological or immunogenic activities. In fact, peptides composed of as few as six galectin 11 amino acid residues may often evoke an immune response.

Accordingly, further embodiments of the invention are directed to C-terminal deletions of the galectin 11 polypeptide described by the general formula 1 to n, where n is an integer from 6 to 132 corresponding to the position of amino acid residue identified in SEQ ID NO:2 and preferably, corresponds to one of the C-terminal amino acid residues identified in the C-terminal deletions specified herein. In specific embodiments, C terminal deletions of the galectin 11 polypeptide of the invention comprise, or alternatively, consist of, amino acid residues: M-1 to H-132; M-1 to V-131; M-1 to C-130; M-1 to Y-129; M-1 to L-128; M-1 to Q-127; M-1 to V-126; M-1 to S-125; M-1 to G-124; M-1 to S-123; M-1 to 1–122; M-1 to R-121; M-1 to L-120; M-1 to E-119; M-1 to R-118; M-1 to L-117; M-1 to Q-116; M-1 to E-115; M-1 to L-114; M-1 to A-113; M-1 to Q-112; M-1 to Q-111; M-1 to N-110; M-1 to M-109; M-1 to S-108; M-1 to T-107; M-1 to A-106; M-1 to G-105; M-1 to L-104; M-1 to G-103; M-1 to Q-102; M-1 to G-101; M-1 to N-100; M-1 to L-99; M-1 to A-98; M-1 to L-97; M-1 to K-96; M-1 to L-95; M-1 to G-94; M-1 to G-93; M-1 to E-92; M-1 to Q-91; M-1 to F-90; M-1 to L-89; M-1 to L-88; M-1 to L-87; M-1 to V-86; M-1 to E-85; M-1 to F-84; M-1 to F-83; M-1 to R-82; M-1 to Q-81; M-1 to P-80; M-1 to Y-79; M-1 to F-78; M-1 to L-77; M-1 to F-76; M-1 to P-75; M-1 to A-74; M-1 to S-73; M-1 to 1–72; M-1 to L-71; M-1 to K-70; M-1 to K-69; M-1 to Q-68; M-1 to G-67; M-1 to W-66; M-1 to R-65; M-1 to S-64; M-1 to I-63; M-1 to W-62; M-1 to A-61; M-1 to L-60; M-1 to T-59; M-1 to R-58; M-1 to D-57; M-1 to A-56; M-1 to F-55; M-1 to S-54; M-1 to A-53; M-1 to R-52; M-1 to L-51; M-1 to T-50; M-1 to V-49; M-1 to P-48; M-1 to A-47; M-1 to H-46; M-1 to A-45; M-1 to A-44; M-1 to Q-43; M-1 to D-42; M-1 to R-41; M-1 to L-40; M-1 to S-39; M-1 to V-38; M-1 to T-37; M-1 to F-36; M-1 to H-35; M-1 to K-34; M-1 to P-33; M-1 to E-32; M-1 to Q-31; M-1 to L-30; M-1 to V-29; M-1 to L-28; M-1 to G-27; M-1 to R-26; M-1 to V-25; M-1 to I-24; M-1 to I-23; M-1 to V-22; M-1 to Q-21; M-1 to G-20; M-1 to P-19; M-1 to S-18; M-1 to L-17; M-1 to G-16; M-1 to Q-15; M-1 to P-14; M-1 to L-13; M-1 to A-12; M-1 to H-11; M-1 to S-10; M-1 to C-9; M-1 to P-8; M-1 to V-7; and M-1 to E-6 of SEQ ID NO:2. Polynucleotides encoding these polypeptides are also encompassed by the invention.

In addition, any of the above listed N- or C-terminal deletions can be combined to produce a N- and C-terminal deleted galectin 11 polypeptide. The invention also provides polypeptides having one or more amino acids deleted from both the amino and the carboxyl termini, which may be described generally as having residues m–n of SEQ ID NO:2, where n and m are integers as described above. Polynucleotides encoding these polypeptides are also encompassed by the invention.

In preferred embodiments, the polypeptides of the invention comprise, or alternatively, consist of, amino acid residues: M-1 to L-40; M-1 to W-66; P-3 to L-40; L-5 to L-40; L-5 to S-108; L-5 to L-128; P-3 to L-128; L-5 to L-128; L-5 to G-124; C-9 to C-130; L-13 to L-40; P-14 to L-40; L-40 to S-108; A-47 to S-108; A-47 to L-128; R-65 to S-108; R-65 to L-128; L-88 to S-108; L-88 to L-128; S-108 to L-120; or L-114 to L-128 of SEQ ID NO:2. Polynucleotides encoding these polypeptides are also encompassed by the invention.

Also included are a nucleotide sequence encoding a polypeptide consisting of a portion of the complete galectin 11 amino acid sequence encoded by the cDNA clone contained in ATCC Deposit No. 209053, where this portion excludes any integer of amino acid residues from 1 to about 123 amino acids from the amino terminus of the complete amino acid sequence encoded by the cDNA clone contained in ATCC Deposit No. 209053, or any integer of amino acid residues from 1 to about 123 amino acids from the carboxy terminus, or any combination of the above amino terminal and carboxy terminal deletions, of the complete amino acid sequence encoded by the cDNA clone contained in ATCC Deposit No. 209053. Polynucleotides encoding all of the above deletion mutant polypeptide forms also are provided.

The present application is also directed to proteins containing polypeptides at least 80%, 85%, 90%, 92%, 95%, 96%, 97%, 98% or 99% identical to the galectin 11 polypeptide sequence set forth herein m-n. In preferred embodiments, the application is directed to proteins containing polypeptides at least 80%, 85%, 90%, 92%, 95%, 96%, 97%, 98% or 99% identical to polypeptides having the amino acid sequence of the specific galectin 11 N- and C-terminal deletions recited herein. Polynucleotides encoding these polypeptides are also encompassed by the invention.

Additional preferred polypeptide fragments comprise, or alternatively consist of, the amino acid sequence of residues: M-1 to Q-15; S-2 to G-16; P-3 to L-17; R-4 to S-18; L-5 to P-19; E-6 to G-20; V-7 to Q-21; P-8 to V-22; C-9 to I-23; S-10 to I-24; H-11 to V-25; A-12 to R-26; L-13 to G-27; P-14 to L-28; Q-15 to V-29; G-16 to L-30; L-17 to Q-31; S-18 to E-32; P-19 to P-33; G-20 to K-34; Q-21 to H-35; V-22 to F-36; I-23 to T-37; I-24 to V-38; V-25 to S-39; R-26 to L-40; G-27 to R-41; L-28 to D-42; V-29 to Q-43; L-30 to A-44; Q-31 to A-45; E-32 to H-46; P-33 to A-47; K-34 to P-48; H-35 to V-49; F-36 to T-50; T-37 to L-51; V-38 to R-52; S-39 to A-53; L-40 to S-54; R-41 to F-55; D-42 to A-56; Q-43 to D-57; A-44 to R-58; A-45 to T-59; H-46 to L-60; A-47 to A-61; P-48 to W-62; V-49 to I-63; T-50 to S-64; L-51 to R-65; R-52 to W-66; A-53 to G-67; S-54 to Q-68; F-55 to K-69; A-56 to K-70; D-57 to L-71; R-58 to I-72; T-59 to S-73; L-60 to A-74; A-61 to P-75; W-62 to F-76; I-63 to L-77; S-64 to F-78; R-65 to Y-79; W-66 to P-80; G-67 to Q-81; Q-68 to R-82; K-69 to F-83; K-70 to F-84; L-71 to E-85; I-72 to V-86; S-73 to L-87; A-74 to L-88; P-75 to L-89; F-76 to F-90; L-77 to Q-91; F-78 to E-92; Y-79 to G-93; P-80 to G-94; Q-81 to L-95; R-82 to K-96; F-83 to L-97; F-84 to A-98; E-85 to L-99; V-86 to N-100; L-87 to G-101; L-88 to Q-102; L-89 to G-103; F-90 to L-104; Q-91 to G-105; E-92 to A-106; G-93 to T-107; G-94 to S-108; L-95 to M-109; K-96 to N-110; L-97 to Q-111; A-98 to Q-112; L-99 to A-113; N-100 to L-114; G-101 to E-115; Q-102 to Q-116; G-103 to L-117; L-104 to R-118; G-105 to E-119; A-106 to L-120; T-107 to R-121; S-108 to I-122; M-109 to S-123; N-110 to G-124; Q-111 to S-125; Q-112 to V-126; A-113 to Q-127; L-114 to L-128; E-115 to Y-129; Q-116 to C-130; L-117 to V-131; R-118 to H-132; and E-119 to S-133 of SEQ ID NO:2. These polypeptide fragments may retain the biological activity of galectin 11 polypeptides of the invention and/or may be useful to generate or screen for antibodies, as described further below. Polynucleotides encoding these polypeptide fragments are also encompassed by the invention.

In another embodiment, the present invention further provides polypeptides having one or more residues deleted from the amino terminus of the amino acid sequence of the galectin 11 polypeptide depicted in SEQ ID NO:25 or encoded by the cDNA of the deposited clone. Particularly, in one embodiment, N-terminal deletions of the galectin 11 polypeptide can be described by the general formula m to 275, where m is a integer from 2 to 270 corresponding to the position of amino acid residue identified in SEQ ID NO:25 and preferably, corresponds to one of the N-terminal amino acid residues identified in the N-terminal deletions specified herein. In specific embodiments, N-terminal deletions of the galectin 11 polypeptide of the invention comprise, or alternatively consist of, amino acid residues: V-2 to S-275; M-3 to S-275; L-4 to S-275; Q-5 to S-275; G-6 to S-275; V-7 to S-275; V-8 to S-275; P-9 to S-275; L-10 to S-275; D-11 to S-275; A-12 to S-275; H-13 to S-275; R-14 to S-275; F-15 to S-275; Q-16 to S-275; V-17 to S-275; D-18 to S-275; F-19 to S-275; Q-20 to S-275; C-21 to S-275; G-22 to S-275; C-23 to S-275; S-24 to S-275; L-25 to S-275; C-26 to S-275; P-27 to S-275; R-28 to S-275; P-29 to S-275; D-30 to S-275; I-31 to S-275; A-32 to S-275; F-33 to S-275; H-34 to S-275; F-35 to S-275; N-36 to S-275; P-37 to S-275; R-38 to S-275; F-39 to S-275; H-40 to S-275; T-41 to S-275; T-42 to S-275; K-43 to S-275; P-44 to S-275; H-45 to S-275; V-46 to S-275; I-47 to S-275; C-48 to S-275; N-49 to S-275; T-50 to S-275; L-51 to S-275; H-52 to S-275; G-53 to S-275; G-54 to S-275; R-55 to S-275; W-56 to S-275; Q-57 to S-275; R-58 to S-275; E-59 to S-275; A-60 to S-275; R-61 to S-275; W-62 to S-275; P-63 to S-275; H-64 to S-275; L-65 to S-275; A-66 to S-275; L-67 to S-275; R-68 to S-275; R-69 to S-275; G-70 to S-275; S-71 to S-275; S-72 to S-275; F-73 to S-275; L-74 to S-275; 1–75 to S-275; L-76 to S-275; F-77 to S-275; L-78 to S-275; F-79 to S-275; G-80 to S-275; N-81 to S-275; E-82 to S-275; E-83 to S-275; V-84 to S-275; K-85 to S-275; V-86 to S-275; S-87 to S-275; V-88 to S-275; N-89 to S-275; G-90 to S-275; Q-91 to S-275; H-92 to S-275; F-93 to S-275; L-94 to S-275; H-95 to S-275; F-96 to S-275; R-97 to S-275; Y-98 to S-275; R-99 to S-275; L-100 to S-275; P-101 to S-275; L-102 to S-275; S-103 to S-275; H-104 to S-275; V-105 to S-275; D-106 to S-275; T-107 to S-275; L-108 to S-275; G-109 to S-275; I-110 to S-275; F-111 to S-275; G-112 to S-275; D-113 to S-275; I-114 to S-275; L-115 to S-275; V-116 to S-275; E-117 to S-275; A-118 to S-275; V-119 to S-275; G-120 to S-275; F-121 to S-275; L-122 to S-275; N-123 to S-275; I-124 to S-275; N-125 to S-275; P-126 to S-275; F-127 to S-275; V-128 to S-275; E-129 to S-275; G-130 to S-275; S-131 to S-275; R-132 to S-275; E-133 to S-275; Y-134 to S-275; P-135 to S-275; A-136 to S-275; G-137 to S-275; H-138 to S-275; P-139 to S-275; F-140 to S-275; L-141 to S-275; L-142 to S-275; M-143 to S-275; S-144 to S-275; P-145 to S-275; R-146 to S-275; L-147 to S-275; E-148 to S- 275; V-149 to S-275; P-150 to S-275; C-151 to S-275; S-152 to S-275; H-153 to S-275; A-154 to S-275; L-155 to S-275; P-156 to S-275; Q-157 to S-275; G-158 to S-275; L-159 to S-275; S-160 to S-275; P-161 to S-275; G-162 to S-275; Q-163 to S-275; V-164 to S-275; I-165 to S-275; I-166 to S-275; V-167 to S-275; R-168 to S-275; G-169 to S-275; L-170 to S-275; V-171 to S-275; L-172 to S-275; Q-173 to S-275; E-174 to S-275; P-175 to S-275; K-176 to S-275; H-177 to S-275; F-178 to S-275; T-179 to S-275; V-180 to S-275; S-181 to S-275; L-182 to S-275; R-183 to S-275; D-184 to S-275; Q-185 to S-275; A-186 to S-275; A-187 to S-275; H-188 to S-275; A-189 to S-275; P-190 to S-275; V-191 to S-275; T-192 to S-275; L-193 to S-275; R-194 to S-275;

A-195 to S-275; S-196 to S-275; F-197 to S-275; A-198 to S-275; D-199 to S-275; R-200 to S-275; T-201 to S-275; L-202 to S-275; A-203 to S-275; W-204 to S-275; I-205 to S-275; S-206 to S-275; R-207 to S-275; W-208 to S-275; G-209 to S-275; Q-210 to S-275; K-211 to S-275; K-212 to S-275; L-213 to S-275; I-214 to S-275; S-215 to S-275; A-216 to S-275; P-217 to S-275; F-218 to S-275; L-219 to S-275; F-220 to S-275; Y-221 to S-275; P-222 to S-275; Q-223 to S-275; R-224 to S-275; F-225 to S-275; F-226 to S-275; E-227 to S-275; V-228 to S-275; L-229 to S-275; L-230 to S-275; L-231 to S-275; F-232 to S-275; Q-233 to S-275; E-234 to S-275; G-235 to S-275; G-236 to S-275; L-237 to S-275; K-238 to S-275; L-239 to S-275; A-240 to S-275; L-241 to S-275; N-242 to S-275; G-243 to S-275; Q-244 to S-275; G-245 to S-275; L-246 to S-275; G-247 to S-275; A-248 to S-275; T-249 to S-275; S-250 to S-275; M-251 to S-275; N-252 to S-275; Q-253 to S-275; Q-254 to S-275; A-255 to S-275; L-256 to S-275; E-257 to S-275; Q-258 to S-275; L-259 to S-275; R-260 to S-275; E-261 to S-275; L-262 to S-275; R-263 to S-275; I-264 to S-275; S-265 to S-275; G-266 to S-275; S-267 to S-275; V-268 to S-275; Q-269 to S-275; and L-270 to S-275 of SEQ ID NO:25. Polynucleotides encoding such polypeptides are also encompassed by the invention.

Further embodiments of the invention are directed to C-terminal deletions of the galectin 11 polypeptide described by the general formula 1 to n, where n is an integer from 6 to 275 corresponding to the position of amino acid residue identified in SEQ ID NO:25 and preferably, corresponds to one of the C-terminal amino acid residues identified in the C-terminal deletions specified herein. In specific embodiments, C terminal deletions of the galectin 11 polypeptide of the invention comprise, or alternatively, consist of, amino acid residues: M-1 to H-274; M-1 to V-273; M-1 to C-272; M-1 to Y-271; M-1 to L-270; M-1 to Q-269; M-1 to V-268; M-1 to S-267; M-1 to G-266; M-1 to S-265; M-1 to I-264; M-1 to R-263; M-1 to L-262; M-1 to E-261; M-1 to R-260; M-1 to L-259; M-1 to Q-258; M-1 to E-257; M-1 to L-256; M-1 to A-255; M-1 to Q-254; M-1 to Q-253; M-1 to N-252; M-1 to M-251; M-1 to S-250; M-1 to T-249; M-1 to A-248; M-1 to G-247; M-1 to L-246; M-1 to G-245; M-1 to Q-244; M-1 to G-243; M-1 to N-242; M-1 to L-241; M-1 to A-240; M-1 to L-239; M-1 to K-238; M-1 to L-237; M-1 to G-236; M-1 to G-235; M-1 to E-234; M-1 to Q-233; M-1 to F-232; M-1 to L-231; M-1 to L-230; M-1 to L-229; M-1 to V-228; M-1 to E-227; M-1 to F-226; M-1 to F-225; M-1 to R-224; M-1 to Q-223; M-1 to P-222; M-1 to Y-221; M-1 to F-220; M-1 to L-219; M-1 to F-218; M-1 to P-217; M-1 to A-216; M-1 to S-215; M-1 to I-214; M-1 to L-213; M-1 to K-212; M-1 to K-211; M-1 to Q-210; M-1 to G-209; M-1 to W-208; M-1 to R-207; M-1 to S-206; M-1 to I-205; M-1 to W-204; M-1 to A-203; M-1 to L-202; M-1 to T-201; M-1 to R-200; M-1 to D-199; M-1 to A-198; M-1 to F-197; M-1 to S-196; M-1 to A-195; M-1 to R-194; M-1 to L-193; M-1 to T-192; M-1 to V-191; M-1 to P-190; M-1 to A-189; M-1 to H-188; M-1 to A-187; M-1 to A-186; M-1 to Q-185; M-1 to D-184; M-1 to R-183; M-1 to L-182; M-1 to S-181; M-1 to V-180; M-1 to T-179; M-1 to F-178; M-1 to H-177; M-1 to K-176; M-1 to P-175; M-1 to E-174; M-1 to Q-173; M-1 to L-172; M-1 to V-171; M-1 to L-170; M-1 to G-169; M-1 to R-168; M-1 to V-167; M-1 to I-166; M-1 to I-165; M-1 to V-164; M-1 to Q-163; M-1 to G-162; M-1 to P-161; M-1 to S-160; M-1 to L-159; M-1 to G-158; M-1 to Q-157; M-1 to P-156; M-1 to L-155; M-1 to A-154; M-1 to H-153; M-1 to S-152; M-1 to C-151; M-1 to P-150; M-1 to V-149; M-1 to E-148; M-1 to L-147; M-1 to R-146; M-1 to P-145; M-1 to S-144; M-1 to M-143; M-1 to L-142; M-1 to L-141; M-1 to F-140; M-1 to P-139; M-1 to H-138; M-1 to G-137; M-1 to A-136; M-1 to P-135; M-1 to Y-134; M-1 to E-133; M-1 to R132; M-1 to S-131; M-1 to G-130; M-1 to E-129; M-1 to V-128; M-1 to F-127; M-1 to P-126; M-1 to N-125; M-1 to I-124; M-1 to N-123; M-1 to L-122; M-1 to F-121; M-1 to G-120; M-1 to V-119; M-1 to A-118; M-1 to E-117; M-1 to V-116; M-1 to L-115; M-1 to I-114; M-1 to D-113; M-1 to G-112; M-1 to F-111; M-1 to I-110; M-1 to G-109; M-1 to L-108; M-1 to T-107; M-1 to D-106; M-1 to V-105; M-1 to H-104; M-1 to S-103; M-1 to L-102; M-1 to P-101; M-1 to L-100; M-1 to R-99; M-1 to Y-98; M-1 to R-97; M-1 to F-96; M-1 to H-95; M-1 to L-94; M-1 to F-93; M-1 to H-92; M-1 to Q-91; M-1 to G-90; M-1 to N- 89; M-1 to V-88; M-1 to S-87; M-1 to V-86; M-1 to K-85; M-1 to V-84; M-1 to E-83; M-1 to E-82; M-1 to N-81; M-1 to G-80; M-1 to F-79; M-1 to L-78; M-1 to F-77; M-1 to L-76; M-1 to I-75; M-1 to L-74; M-1 to F-73; M-1 to S-72; M-1 to S-71; M-1 to G-70; M-1 to R-69; M-1 to R-68; M-1 to L-67; M-1 to A-66; M-1 to L-65; M-1 to H-64; M-1 to P-63; M-1 to W-62; M-1 to R-61; M-1 to A-60; M-1 to E-59; M-1 to R-58; M-1 to Q-57; M-1 to W-56; M-1 to R-55; M-1 to G-54; M-1 to G-53; M-1 to H-52; M-1 to L-51; M-1 to T-50; M-1 to N-49; M-1 to C-48; M-1 to I-47; M-1 to V-46; M-1 to H-45; M-1 to P-44; M-1 to K-43; M-1 to T-42; M-1 to T-41; M-1 to H-40; M-1 to F-39; M-1 to R-38; M-1 to P-37; M-1 to N-36; M-1 to F-35; M-1 to H-34; M-1 to F-33; M-1 to A-32; M-1 to I-31; M-1 to D-30; M-1 to P-29; M-1 to R-28; M-1 to P-27; M-1 to C-26; M-1 to L-25; M-1 to S-24; M-1 to C-23; M-1 to G-22; M-1 to C-21; M-1 to Q-20; M-1 to F-19; M-1 to D-18; M-1 to V-17; M-1 to Q-16; M-1 to F-15; M-1 to R-14; M-1 to H-13; M-1 to A-12; M-1 to D-11; M-1 to L-10; M-1 to P-9; M-1 to V-8; M-1 to V-7; and M-1 to G-6 all of SEQ ID NO:25. Polynucleotides encoding such polypeptides are also encompassed by the invention.

Further embodiments of the invention are directed to polypeptide fragments comprising, or alternatively, consisting of, amino acids described by the general formula m to n, where m and n correspond to any one of the amino acid residues specified above for these symbols, respectively. Polynucleotides encoding these polypeptides are also encompassed by the invention.

In yet another embodiment, the present invention further provides polypeptides having one or more residues deleted from the amino terminus of the amino acid sequence of the galectin 11 polypeptide depicted in SEQ ID NO:27. Particularly, in one embodiment, N-terminal deletions of the galectin 11 polypeptide can be described by the general formula m to 296, where m is an integer from 2 to 291 corresponding to the position of amino acid residue identified in SEQ ID NO:27 and preferably, corresponds to one of the N-terminal amino acid residues identified in the N-terminal deletions specified herein. In specific embodiments, N-terminal deletions of the galectin 11 polypeptide of the invention comprise, or alternatively consist of, amino acid residues: S-2 to S-296; F-3 to S-296; F-4 to S-296; S-5 to S-296; C-6 to S-296; S-7 to S-296; G-8 to S-296; G-9 to S-296; S-10 to S-296; L-11 to S-296; C-12 to S-296; H-13 to S-296; D-14 to S-296; D-15 to S-296; F-16 to S-296; W-17 to S-296; R-18 to S-296; P-19 to S-296; A-20 to S-296; C-21 to S-296; R-22 to S-296; Q-23 to S-296; D-24 to S-296; G-25 to S-296; H-26 to S-296; A-27 to S-296; A-28 to S-296; R-29 to S-296; S-30 to S-296; G-31 to S-296; P-32 to S-296; S-33 to S-296; R-34 to S-296; C-35 to S-296; T-36 to S-296; Q-37 to S-296; V-38 to S-296; D-39 to S-296; F-40 to S-296; Q-41 to S-296; C-42 to S-296; G-43 to S-296; C-44 to S-296; S-45 to S-296; L-46 to S-296; C-47 to S-296; P-48 to S-296; R-49 to S-296; P-50 to S-296; D-51 to S-296; I-52 to S-296; A-53 to S-296; F-54 to S-296; H-55 to S-296; F-56 to S-296; N-57 to S-296; P-58 to S-296; R-59 to S-296; F-60 to S-296; H-61 to S-296; T-62 to S-296; T-63 to S-296; K-64 to S-296; P-65 to S-296; H-66 to S-296; V-67 to S-296; I-68 to S-296; C-69 to S-296; N-70 to S-296; T-71 to S-296; L-72 to S-296; H-73 to S-296; G-74 to S-296; G-75 to S-296; R-76 to S-296; W-77 to S-296; Q-78 to S-296; R-79 to S-296; E-80 to S-296; A-81 to S-296; R-82 to S-296; W-83 to S-296; P-84 to S-296; H-85 to S-296; L-86 to S-296; A-87 to S-296; L-88 to S-296; R-89 to S-296; R-90 to S-296; G-91 to S-296; S-92 to S-296; S-93 to S-296; F-94 to S-296; L-95 to S-296; I-96 to S-296; L-97 to S-296; F-98 to S-296; L-99 to S-296; F-100 to S-296; G-101 to S-296; N-102 to S-296; E-103 to S-296; E-104 to S-296; V-105 to S-296; K-106 to S-296; V-107 to S-296; S-108 to S-296; V-109 to S-296; N-110 to S-296; G-111 to S-296; Q-112 to S-296; H-113 to S-296; F-114 to S-296; L-115 to S-296; H-116 to S-296; F-117 to S-296; R-118 to S-296; Y-119 to S-296; R-120 to S-296; L-121 to S-296; P-122 to S-296; L-123 to S-296; S-124 to S-296; H-125 to S-296; V-126 to S-296; D-127 to S-296; T-128 to S-296; L-129 to S-296; G-130 to S-296; I-131 to S-296; F-132 to S-296; G-133 to S-296; D-134 to S-296; I-135 to S-296; L-136 to S-296; V-137 to S-296; E-138 to S-296; A-139 to S-296; V-140 to S-296; G-141 to S-296; F-142 to S-296; L-143 to S-296; N-144 to S-296; I-145 to S-296; N-146 to S-296; P-147 to S-296; F-148 to S-296; V-149 to S-296; E-150 to S-296; G-151 to S-296; S-152 to S-296; R-153 to S-296; E-154 to S-296; Y-155 to S-296; P-156 to S-296; A-157 to S-296; G-158 to S-296; H-159 to S-296; P-160 to S-296; F-161 to S-296; L-162 to S-296; L-163 to S-296; M-164 to S-296; S-165 to S-296; P-166 to S-296; R-167 to S-296; L-168 to S-296; E-169 to S-296; V-170 to S-296; P-171 to S-296; C-172 to S-296; S-173 to S-296; H-174 to S-296; A-175 to S-296; L-176 to S-296; P-177 to S-296; Q-178 to S-296; G-179 to S-296; L-180 to S-296; S-181 to S-296; P-182 to S-296; G-183 to S-296; Q-184 to S-296; V-185 to S-296; I-186 to S-296; I-187 to S-296; V-188 to S-296; R-189 to S-296; G-190 to S-296; L-191 to S-296; V-192 to S-296; L-193 to S-296; Q-194 to S-296; E-195 to S-296; P-196 to S-296; K-197 to S-296; H-198 to S-296; F-199 to S-296; T-200 to S-296; V-201 to S-296; S-202 to S-296; L-203 to S-296; R-204 to S-296; D-205 to S-296; Q-206 to S-296; A-207 to S-296; A-208 to S-296; H-209 to S-296; A-210 to S-296; P-211 to S-296; V-212 to S-296; T-213 to S-296; L-214 to S-296; R-215 to S-296; A-216 to S-296; S-217 to S-296; F-218 to S-296; A-219 to S-296; D-220 to S-296; R-221 to S-296; T-222 to S-296; L-223 to S-296; A-224 to S-296; W-225 to S-296; I-226 to S-296; S-227 to S-296; R-228 to S-296; W-229 to S-296; G-230 to S-296; Q-231 to S-296; K-232 to S-296; K-233 to S-296; L-234 to S-296; I-235 to S-296; S-236 to S-296; A-237 to S-296; P-238 to S-296; F-239 to S-296; L-240 to S-296; F-241 to S-296; Y-242 to S-296; P-243 to S-296; Q-244 to S-296; R-245 to S-296; F-246 to S-296; F-247 to S-296; E-248 to S-296; V-249 to S-296; L-250 to S-296; L-251 to S-296; L-252 to S-296; F-253 to S-296; Q-254 to S-296; E-255 to S-296; G-256 to S-296; G-257 to S-296; L-258 to S-296; K-259 to S-296; L-260 to S-296; A-261 to S-296; L-262 to S-296; N-263 to S-296; G-264 to S-296; Q-265 to S-296; G-266 to S-296; L-267 to S-296; G-268 to S-296; A-269 to S-296; T-270 to S-296; S-271 to S-296; M-272 to S-296; N-273 to S-296; Q-274 to S-296; Q-275 to S-296; A-276 to S-296; L-277 to S-296; E-278 to S-296; Q-279 to S-296; L-280 to S-296; R-281 to S-296; E-282 to S-296; L-283 to S-296; R-284 to S-296; I-285 to S-296; S-286 to S-296; G-287 to S-296; S-288 to S-296; V-289 to S-296; Q-290 to S-296; L-291 to S-296; of SEQ ID NO:27. Polynucleotides encoding such polypeptides are also provided.

Further embodiments of the invention are directed to C-terminal deletions of the galectin 11 polypeptide described by the general formula 1 to n, where n is an integer from 6 to 295 corresponding to the position of amino acid residue identified in SEQ ID NO:27 and preferably, corresponds to one of the C-terminal amino acid residues identified in the C-terminal deletions specified herein. In specific embodiments, C terminal deletions of the galectin 11 polypeptide of the invention comprise, or alternatively, consist of, amino acid residues: M-1 to H-295; M-1 to V-294; M-1 to C-293; M-1 to Y-292; M-1 to L-291; M-1 to Q-290; M-1 to V-289; M-1 to S-288; M-1 to G-287; M-1 to S-286; M-1 to I-285; M-1 to R-284; M-1 to L-283; M-1 to E-282; M-1 to R-281; M-1 to L-280; M-1 to Q-279; M-1 to E-278; M-1 to L-277; M-1 to A-276; M-1 to Q-275; M-1 to Q-274; M-1 to N-273; M-1 to M-272; M-1 to S-271; M-1 to T-270; M-1 to A-269; M-1 to G-268; M-1 to L-267; M-1 to G-266; M-1 to Q-265; M-1 to G-264; M-1 to N-263; M-1 to L 262; M-1 to A-261; M-1 to L-260; M-1 to K-259; M-1 to L-258; M-1 to G-257; M-1 to G-256; M-1 to E-255; M-1 to Q-254; M-1 to F-253; M-1 to L-252; M-1 to L-251; M-1 to L-250; M-1 to V-249; M-1 to E-248; M-1 to F-247; M-1 to F-246; M-1 to R-245; M-1 to Q-244; M-1 to P-243; M-1 to Y-242; M-1 to F-241; M-1 to L-240; M-1 to F-239; M-1 to P-238; M-1 to A-237; M-1 to S-236; M-1 to I-235; M-1 to L-234; M-1 to K-233; M-1 to K-232; M-1 to Q-231; M-1 to G-230; M-1 to W-229; M-1 to R-228; M-1 to S-227; M-1 to I-226; M-1 to W-225; M-1 to A-224; M-1 to L-223; M-1 to T-222; M-1 to R-221; M-1 to D-220; M-1 to A-219; M-1 to F-218; M-1 to S-217; M-1 to A-216; M-1 to R-215; M-1 to L-214; M-1 to T-213; M-1 to V-212; M-1 to P-211; M-1 to A-210; M-1 to H-209; M-1 to A-208; M-1 to A-207; M-1 to Q-206; M-1 to D-205; M-1 to R-204; M-1 to L-203; M-1 to S-202; M-1 to V-201; M-1 to T-200; M-1 to F-199; M-1 to H-198; M-1 to K-197; M-1 to P-196; M-1 to E-195; M-1 to Q-194; M-1 to L-193; M-1 to V-192; M-1 to L-191; M-1 to G-190; M-1 to R-189; M-1 to V-188; M-1 to I-187; M-1 to I-186; M-1 to V-185; M-1 to Q-184; M-1 to G-183; M-1 to P-182; M-1 to S-181; M-1 to L-180; M-1 to G-179; M-1 to Q-178; M-1 to P-177; M-1 to L-176; M-1 to A-175; M-1 to H-174; M-1 to S-173; M-1 to C-172; M-1 to P-171; M-1 to V-170; M-1 to E-169; M-1 to L-168; M-1 to R-167; M-1 to P-166; M-1 to S-165; M-1 to M-164; M-1 to L-163; M-1 to L-162; M-1 to F-161; M-1 to P-160; M-1 to H-159; M-1 to G-158; M-1 to A-157; M-1 to P-156; M-1 to Y-155; M-1 to E-154; M-1 to R-153; M-1 to S-152; M-1 to G-151; M-1 to E-150; M-1 to V-149; M-1 to F-148; M-1 to P-147; M-1 to N-146; M-1 to I-145; M-1 to N-144; M-1 to L-143; M-1 to F-142; M-1 to G-141; M-1 to V-140; M-1 to A-139; M-1 to E-138; M-1 to V-137; M-1 to L-136; M-1 to I-135; M-1 to D-134; M-1 to G-133; M-1 to F-132; M-1 to I-131; M-1 to G-130; M-1 to L-129; M-1 to T-128; M-1 to D-127; M-1 to V-126; M-1 to H-125; M-1 to S-124; M-1 to L-123; M-1 to P-122; M-1 to L-121; M-1 to R-120; M-1 to Y-119; M-1 to R-118; M-1 to F-117; M-1 to H-116; M-1 to L-115; M-1 to F-114; M-1 to H-113; M-1 to Q-112; M-1 to G-111; M-1 to N-110; M-1 to V-109; M-1 to S-108; M-1 to V-107; M-1 to K-106; M-1 to v-105; M-1 to E-104; M-1 to E-103; M-1 to N-102; M-1 to G-101; M-1 to F-100; M-1 to L-99; M-1 to F-98; M-1 to L-97; M-1 to I-96; M-1 to L-95; M-1 to F-94; M-1 to S-92; M-1 to G-91; M-1 to R-90; M-1 to R-89; M-1 to L-88; M-1 to A-87; M-1 to L-86; M-1 to H-85; M-1 to P-84; M-1 to W-83; M-1 to R-82; M-1 to A-81; M-1 to E-80; M-1 to R- 79; M-1 to Q-78; M-1 to W-77; M-1 to R-76; M-1 to G-75; M-1 to G-74; M-1 to H-73; M-1 to L-72; M-1 to T-71; M-1 to N-70; M-1 to C-69; M-1 to I-68; M-1 to V-67; M-1 to H-66; M-1 to P-65; M-1 to K-64; M-1 to T-63; M-1 to T-62; M-1 to H-61; M-1 to F-60; M-1 to R-59; M-1 to P-58; M-1 to N-57; M-1 to F-56; M-1 to H-55; M-1 to F-54; M-1 to A-53; M-1 to I-52; M-1 to D-51; M-1 to P-50; M-1 to R-49; M-1 to P-48; M-1 to C-47; M-1 to L-46; M-1 to S-45; M-1 to C-44; M-1 to G-43; M-1 to C-42; M-1 to Q-41; M-1 to F-40; M-1 to D-39; M-1 to V-38; M-1 to Q-37; M-1 to T-36; M-1 to C-35; M-1 to R-34; M-1 to S-33; M-1 to P-32; M-1 to G-31; M-1 to S-30; M-1 to R-29; M-1 to A-28; M-1 to A-27; M-1 to H-26; M-1 to G-25; M-1 to D-24; M-1 to Q-23; M-1 to R-22; M-1 to C-21; M-1 to A-20; M-1 to P-19; M-1 to R-18; M-1 to W-17; M-1 to F-16; M-1 to D-15; M-1 to D-14; M-1 to H-13; M-1 to C-12; M-1 to L-11; M-1 to S-10; M-1 to G-9; M-1 to G-8; M-1 to S-7; M-1 to C-6, all of SEQ ID NO:27. Polynucleotides encoding such polypeptides are also encompassed by the invention.

Further embodiments of the invention are directed to polypeptide fragments comprising, or alternatively, consisting of, amino acids described by the general formula m to n, where m and n correspond to any one of the amino acid residues specified above for these symbols, respectively. Polynucleotides encoding these polypeptides are also encompassed by the invention.

FIG. 2 provides a comparison of the galectin 11 polypeptide with other galectins. Identical amino acids shared between the galectins are shaded, while conservative amino acid changes are boxed. By examining the regions of amino acids shaded and/or boxed, the skilled artisan can readily identify conserved domains between the two polypeptides. The amino acid sequences falling within these conserved, shaded and/or boxed domains are contained in the preferred polypeptide fragments of the invention. Similar analyses for the full-length galectin-11α and β is deemed to be within the skill of the ordinary artisan given the teachings provided herein.

Representative examples of polypeptide residue fragments of the invention including, for example, fragments from about amino acid number 1–20, 1–66, 5–108, 5–128, 21–40, 40–108, 41–60, 47–108, 47–128, 61–80, 65–108, 65–128, 81–100, 88–128, 108–120; 114–128; and 101 to the end of the galectin 11 polypeptide depicted in FIG. 1 (SEQ ID NO:2). In this context, "about" includes the particularly recited ranges larger or smaller by several, 5, 4, 3, 2, or 1 amino acid at either end or at both extremes. Representative examples of polypeptide residue fragments of the invention including, for example, fragments from about amino acid number 1–20, 1–66, 5–108, 5–128, 21–40, 40–108, 41–60, 47–108, 47–128, 61–80, 65–108, 65–128, 81–100, 88–108, 88–128, 108–120; 114–128; 129–150; 145–175; 170–200; 195–225; 220–250; and 245–275 of SEQ ID NO:25. Additional representative examples of polypeptide residue fragments of the invention including, for example, fragments from about amino acid number 1–20, 1–66, 5–108, 5–128, 21–40, 40–108, 41–60, 47–108, 47–128, 61–80, 65–108, 65–128, 81–100, 88–128, 108–120; 114–128; 129–150; 145–175; 170–200; 195–225; 220–250; 245–275; and 270–296 of SEQ ID NO:27. Polypeptides comprising such amino acid sequences are provided as well as polynucleotides encoding such polypeptides.

Preferably, the polynucleotide fragments of the invention encode a polypeptide which demonstrates a galectin 11 functional activity. By a polypeptide demonstrating a galectin 11 "functional activity" is meant, a polypeptide capable of displaying one or more known functional activities associated with a full-length (complete) galectin 11 protein. Such functional activities include, but are not limited to, biological activity, antigenicity [ability to bind (or compete with a galectin 11 polypeptide for binding) to an anti-galectin 11 antibody], immunogenicity (ability to generate antibody which binds to a galectin 11 polypeptide), ability to form multimers with galectin 11 polypeptides of the invention.

Among the especially preferred fragments of the invention are fragments characterized by structural or functional attributes of galectin 11. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., having an antigenic region of three or more contiguous amino acid residues each of which having an antigenic index of greater than or equal to 1.5) of galectin 11. Certain preferred regions are those set out in FIG. 3 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of galectin 11. Preferred embodiments of the invention in this regard include fragments that comprise alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of galectin 11.

The data representing the structural or functional attributes of galectin 11 set forth in FIG. 1 and/or Table I, as described above, was generated using the various modules and algorithms of the DNA*STAR set on default parameters. In a preferred embodiment, the data presented in columns VIII, XII, and XIII of Table I can be used to determine regions of galectin 11 which exhibit a high degree of potential for antigenicity. Regions of high antigenicity are determined from the data presented in columns VII, XII, and/or XIII by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIG. 1. As set out in FIG. 3 and in Table I, such preferred regions include Garnier-Robson alpha-regions, beta-regions, turn-regions, and coil-regions, Chou-Fasman alpha-regions, beta-regions, and turn-regions, Kyte-Doolittle hydrophilic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII |
|---|---|---|---|---|---|---|---|---|---|---|---|---|---|---|
| Met | 1 | . | . | B | . | . | . | . | 0.13 | . | * | . | 0.65 | 1.50 |
| Ser | 2 | . | . | . | . | . | T | C | 0.52 | . | * | . | 0.90 | 0.97 |
| Pro | 3 | . | . | B | . | . | T | . | 0.06 | . | * | . | 0.85 | 1.32 |
| Arg | 4 | . | . | . | . | T | T | . | 0.23 | . | * | . | 1.10 | 0.99 |
| Leu | 5 | A | . | . | . | . | T | . | −0.04 | . | * | . | 0.85 | 1.14 |
| Glu | 6 | . | . | B | . | . | . | . | 0.26 | . | * | . | 0.50 | 0.39 |
| Val | 7 | . | . | B | . | . | T | . | 0.52 | . | * | . | 0.70 | 0.27 |
| Pro | 8 | . | . | B | . | . | T | . | 0.14 | * | * | . | 0.10 | 0.45 |
| Cys | 9 | . | . | . | . | T | T | . | −0.78 | * | * | . | 0.50 | 0.26 |
| Ser | 10 | . | . | B | . | . | T | . | −0.18 | . | . | . | −0.20 | 0.29 |
| His | 11 | . | . | B | . | . | . | . | −0.18 | . | . | . | −0.40 | 0.29 |
| Ala | 12 | . | . | B | . | . | . | . | 0.33 | . | . | . | −0.40 | 0.93 |
| Leu | 13 | . | . | B | . | . | . | . | −0.27 | * | . | . | −0.10 | 0.69 |
| Pro | 14 | . | . | . | . | T | T | . | 0.10 | * | . | F | 0.35 | 0.42 |
| Gln | 15 | . | . | . | . | T | T | . | 0.19 | * | . | F | 0.35 | 0.55 |
| Gly | 16 | . | . | . | . | T | T | . | −0.12 | * | . | F | 0.50 | 1.04 |
| Leu | 17 | . | . | . | . | . | T | C | 0.47 | . | . | F | 0.45 | 0.66 |
| Ser | 18 | . | . | . | . | . | T | C | 0.42 | * | . | F | 0.45 | 0.66 |
| Pro | 19 | . | . | . | . | . | T | C | −0.26 | * | . | F | 0.45 | 0.50 |
| Gly | 20 | . | . | B | . | . | T | . | −1.14 | . | . | F | −0.05 | 0.42 |
| Gln | 21 | . | . | B | . | . | T | . | −1.66 | * | . | F | −0.05 | 0.22 |
| Val | 22 | . | . | B | B | . | . | . | −0.73 | * | . | . | −0.60 | 0.11 |
| Ile | 23 | . | . | B | B | . | . | . | −0.78 | * | . | . | −0.60 | 0.21 |
| Ile | 24 | . | . | B | B | . | . | . | −1.38 | . | . | . | −0.60 | 0.12 |
| Val | 25 | . | . | B | B | . | . | . | −1.89 | . | . | . | −0.60 | 0.13 |
| Arg | 26 | . | . | B | B | . | . | . | −2.70 | . | . | . | −0.60 | 0.14 |
| Gly | 27 | . | . | B | B | . | . | . | −1.84 | . | . | . | −0.60 | 0.17 |
| Leu | 28 | . | . | B | B | . | . | . | −0.96 | . | . | . | −0.60 | 0.39 |
| Val | 29 | . | . | B | B | . | . | . | −0.28 | * | . | . | 0.30 | 0.34 |
| Leu | 30 | A | . | . | B | . | . | . | 0.62 | * | * | . | −0.30 | 0.54 |
| Gln | 31 | A | . | . | B | . | . | . | 0.48 | * | . | F | 0.60 | 1.30 |
| Glu | 32 | . | . | B | B | . | . | . | 0.12 | * | . | F | 0.60 | 2.39 |
| Pro | 33 | A | . | . | . | . | . | . | 0.62 | . | . | F | 0.80 | 2.51 |
| Lys | 34 | A | . | . | B | . | . | . | 0.62 | * | . | F | 0.60 | 2.09 |
| His | 35 | A | . | . | B | . | . | . | 1.13 | * | . | . | 0.30 | 0.89 |
| Phe | 36 | . | . | B | B | . | . | . | 0.32 | * | * | . | −0.30 | 0.78 |
| Thr | 37 | . | . | B | B | . | . | . | 0.43 | * | * | . | −0.60 | 0.32 |
| Val | 38 | . | . | B | B | . | . | . | 0.64 | * | * | . | −0.60 | 0.46 |
| Ser | 39 | A | A | . | . | . | . | . | 0.60 | * | . | . | 0.30 | 0.89 |
| Leu | 40 | A | A | . | . | . | . | . | 0.04 | . | * | . | 0.45 | 1.07 |
| Arg | 41 | A | A | . | . | . | . | . | 0.16 | . | * | . | 0.45 | 1.45 |
| Asp | 42 | A | A | . | . | . | . | . | 0.43 | . | * | . | 0.75 | 1.09 |
| Gln | 43 | A | A | . | . | . | . | . | 0.70 | . | * | . | 0.45 | 1.80 |
| Ala | 44 | A | A | . | . | . | . | . | 0.79 | . | * | . | 0.60 | 0.93 |
| Ala | 45 | A | A | . | . | . | . | . | 0.74 | . | * | . | 0.30 | 0.86 |
| His | 46 | A | A | . | . | . | . | . | 0.32 | . | * | . | −0.60 | 0.37 |
| Ala | 47 | . | A | B | . | . | . | . | −0.49 | . | * | . | −0.60 | 0.53 |
| Pro | 48 | . | A | B | . | . | . | . | −0.38 | . | * | . | −0.60 | 0.43 |
| Val | 49 | A | A | . | . | . | . | . | −0.38 | . | * | . | −0.30 | 0.62 |
| Thr | 50 | A | A | . | . | . | . | . | −0.09 | . | * | . | −0.30 | 0.62 |
| Leu | 51 | . | A | B | . | . | . | . | −0.76 | . | * | . | −0.30 | 0.54 |
| Arg | 52 | . | A | B | . | . | . | . | −0.76 | . | * | . | −0.60 | 0.63 |
| Ala | 53 | A | A | . | . | . | . | . | −0.54 | . | * | . | −0.30 | 0.44 |
| Ser | 54 | A | A | . | . | . | . | . | 0.42 | . | * | . | 0.30 | 0.89 |
| Phe | 55 | A | A | . | . | . | . | . | 0.42 | . | * | . | 0.60 | 0.89 |
| Ala | 56 | A | A | . | . | . | . | . | 0.42 | . | * | . | 0.45 | 1.27 |
| Asp | 57 | A | A | . | . | . | . | . | −0.28 | . | * | F | 0.45 | 0.78 |
| Arg | 58 | A | A | . | . | . | . | . | 0.02 | * | . | F | 0.45 | 0.91 |
| Thr | 59 | A | A | . | . | . | . | . | −0.57 | * | . | . | −0.30 | 0.95 |
| Leu | 60 | A | A | . | . | . | . | . | −0.17 | * | . | . | −0.30 | 0.40 |
| Ala | 61 | A | A | . | . | . | . | . | 0.53 | * | . | . | −0.60 | 0.27 |
| Trp | 62 | A | A | . | . | . | . | . | 0.24 | * | . | . | −0.60 | 0.37 |
| Ile | 63 | A | A | . | . | . | . | . | −0.21 | * | . | . | −0.26 | 0.47 |
| Ser | 64 | A | . | . | . | . | . | T | 0.10 | * | . | . | 0.48 | 0.46 |
| Arg | 65 | . | . | . | . | T | T | . | 0.96 | * | . | . | 1.22 | 0.76 |
| Trp | 66 | . | . | . | . | T | T | . | 1.59 | * | . | F | 2.76 | 2.17 |
| Gly | 67 | . | . | . | . | T | T | . | 1.07 | * | . | F | 3.40 | 3.24 |
| Gln | 68 | . | A | . | . | T | . | . | 1.07 | * | . | F | 2.66 | 1.36 |
| Lys | 69 | . | A | . | . | T | . | . | 1.07 | * | . | F | 1.27 | 0.91 |
| Lys | 70 | . | A | B | . | . | . | . | 0.37 | * | . | F | 1.28 | 1.23 |
| Leu | 71 | . | A | B | . | . | . | . | 0.44 | . | . | F | 0.79 | 0.72 |
| Ile | 72 | . | A | B | . | . | . | . | 0.09 | . | . | . | 0.30 | 0.55 |
| Ser | 73 | . | . | B | . | . | . | . | −0.72 | . | . | . | −0.40 | 0.24 |
| Ala | 74 | . | . | B | . | . | . | . | −1.47 | * | . | . | −0.40 | 0.24 |
| Pro | 75 | . | . | B | B | . | . | . | −1.76 | . | . | . | −0.60 | 0.30 |
| Phe | 76 | . | . | B | B | . | . | . | −1.16 | . | . | . | −0.60 | 0.35 |
| Leu | 77 | . | . | B | B | . | . | . | −0.27 | . | * | . | −0.60 | 0.53 |

TABLE I-continued

| Res | Position | I | II | III | IV | V | VI | VII | VIII | IX | X | XI | XII | XIII |
|---|---|---|---|---|---|---|---|---|---|---|---|---|---|---|
| Phe | 78 | . | . | B | B | . | . | . | 0.14 | * | . | . | −0.60 | 0.59 |
| Tyr | 79 | . | . | B | . | . | . | T | . | 0.03 | * | . | . | −0.05 | 1.35 |
| Pro | 80 | . | . | . | . | . | . | T | C | −0.46 | * | . | F | 0.30 | 1.41 |
| Gln | 81 | . | . | . | . | T | T | . | 0.24 | * | . | F | 0.50 | 1.41 |
| Arg | 82 | A | . | . | . | . | . | T | . | 0.20 | * | . | F | 0.40 | 1.56 |
| Phe | 83 | A | A | . | . | . | . | . | . | 0.09 | * | . | . | −0.30 | 0.75 |
| Phe | 84 | A | A | . | . | . | . | . | . | −0.48 | * | . | . | −0.30 | 0.36 |
| Gln | 85 | A | A | . | . | . | . | . | . | −1.08 | * | . | . | −0.60 | 0.15 |
| Val | 86 | A | A | . | . | . | . | . | . | −1.78 | * | . | . | −0.60 | 0.14 |
| Leu | 87 | A | A | . | . | . | . | . | . | −1.89 | * | . | . | −0.60 | 0.14 |
| Leu | 88 | A | A | . | . | . | . | . | . | −1.19 | * | . | . | −0.60 | 0.14 |
| Leu | 89 | A | A | . | . | . | . | . | . | −0.83 | . | . | . | −0.60 | 0.33 |
| Phe | 90 | A | A | . | . | . | . | . | . | −1.18 | . | . | . | −0.60 | 0.40 |
| Gln | 91 | A | . | . | . | . | . | T | . | −1.13 | * | . | F | −0.05 | 0.48 |
| Gln | 92 | A | . | . | . | . | . | T | . | −0.28 | * | * | F | −0.05 | 0.48 |
| Gly | 93 | A | . | . | . | . | . | T | . | −0.28 | . | . | F | 1.00 | 1.11 |
| Gly | 94 | A | . | . | . | . | . | T | . | −0.06 | . | * | F | 0.85 | 0.53 |
| Leu | 95 | A | A | . | . | . | . | . | . | −0.17 | * | * | F | 0.45 | 0.31 |
| Lys | 96 | A | A | . | . | . | . | . | . | −0.17 | * | * | . | −0.60 | 0.26 |
| Leu | 97 | . | A | B | . | . | . | . | . | −0.51 | * | . | . | −0.30 | 0.42 |
| Ala | 98 | . | A | B | . | . | . | . | . | −0.17 | . | * | . | −0.30 | 0.50 |
| Leu | 99 | . | A | B | . | . | . | . | . | −0.17 | . | * | . | −0.30 | 0.43 |
| Asn | 100 | . | A | B | . | . | . | . | . | −0.17 | . | * | F | −0.45 | 0.52 |
| Gly | 101 | . | . | B | . | . | T | . | −0.56 | . | * | F | −0.05 | 0.43 |
| Gln | 102 | . | . | B | . | . | T | C | −0.33 | . | * | F | 0.15 | 0.51 |
| Gly | 103 | . | . | . | . | . | T | C | −0.06 | . | . | F | 0.45 | 0.32 |
| Leu | 104 | . | . | . | . | . | T | C | 0.46 | . | . | F | 0.45 | 0.47 |
| Gly | 105 | . | . | . | . | . | . | C | −0.14 | . | . | F | 0.25 | 0.36 |
| Ala | 106 | . | . | . | B | . | . | . | . | 0.20 | . | . | F | −0.25 | 0.36 |
| Thr | 107 | . | . | B | . | . | . | . | . | 0.20 | . | . | F | −0.25 | 0.71 |
| Ser | 108 | . | . | B | . | . | . | . | . | 0.54 | . | . | F | 0.40 | 1.23 |
| Met | 109 | . | . | B | . | . | T | . | 0.77 | . | . | F | 0.40 | 2.12 |
| Asn | 110 | A | . | . | . | . | T | . | 0.30 | * | . | F | 0.40 | 1.48 |
| Gln | 111 | A | . | . | . | . | T | . | 0.89 | * | . | F | 0.25 | 0.91 |
| Gln | 112 | A | A | . | . | . | . | . | . | 1.20 | * | . | F | 0.60 | 1.60 |
| Ala | 113 | A | A | . | . | . | . | . | . | 0.69 | * | * | F | 0.60 | 1.72 |
| Leu | 114 | A | A | . | . | . | . | . | . | 1.40 | * | . | F | −0.15 | 0.82 |
| Gln | 115 | A | A | . | . | . | . | . | . | 1.40 | * | . | . | 0.30 | 0.93 |
| Gln | 116 | A | A | . | . | . | . | . | . | 0.59 | * | . | F | 0.90 | 1.59 |
| Leu | 117 | A | A | . | . | . | . | . | . | 0.70 | * | * | F | 0.90 | 1.59 |
| Arg | 118 | A | A | . | . | . | . | . | . | 0.40 | * | * | F | 1.15 | 1.79 |
| Glu | 119 | A | A | . | . | . | . | . | . | 0.91 | * | * | . | 1.10 | 0.73 |
| Leu | 120 | A | A | . | . | . | . | . | . | 0.57 | * | * | . | 1.50 | 1.18 |
| Arg | 121 | . | A | . | . | T | . | . | 0.27 | * | * | . | 2.00 | 0.60 |
| Ile | 122 | . | . | . | . | T | T | . | 0.22 | * | * | F | 2.50 | 0.46 |
| Ser | 123 | . | . | . | . | T | T | . | 0.11 | * | * | F | 1.65 | 0.42 |
| Gly | 124 | . | . | . | . | T | T | . | −0.70 | . | * | F | 2.00 | 0.37 |
| Ser | 125 | . | . | . | . | T | T | . | −0.13 | . | * | F | 0.85 | 0.43 |
| Val | 126 | . | . | B | B | . | . | . | −0.91 | . | * | . | −0.35 | 0.50 |
| Gln | 127 | . | . | B | B | . | . | . | −0.88 | . | * | . | −0.60 | 0.27 |
| Leu | 128 | . | . | B | B | . | . | . | −0.61 | . | . | . | −0.60 | 0.15 |
| Tyr | 129 | . | . | B | B | . | . | . | −0.57 | . | . | . | −0.60 | 0.28 |
| Cys | 130 | . | . | B | B | . | . | . | −0.66 | . | . | . | −0.60 | 0.21 |
| Val | 131 | . | . | B | B | . | . | . | −0.19 | . | . | . | −0.60 | 0.33 |
| His | 132 | . | . | B | B | . | . | . | −0.58 | . | . | . | −0.60 | 0.27 |
| Ser | 133 | . | . | B | B | . | . | . | −0.16 | . | . | . | −0.30 | 0.65 |

FIG. 2 provides a comparison of the galectin 11 polypeptide with other galectins. Identical amino acids shared between the galectins are shaded, while conservative amino acid changes are boxed. By examining the regions of amino acids shaded and/or boxed, the skilled artisan can readily identify conserved domains between the two polypeptides. The amino acid sequences falling within these conserved, shaded and/or boxed domains are contained in the preferred polypeptide fragments of the invention.

Among highly preferred fragments in this regard are those that comprise regions of galectin 11 that combine several structural features, such as several of the features set out above.

Other preferred polypeptide fragments are biologically active galectin 11 fragments. Biologically active fragments are those exhibiting activity similar, but not necessarily identical, to an activity of the galectin 11 polypeptide. The biological activity of the fragments may include an improved desired activity, or a decreased undesirable activity. Polynucleotides encoding these polypeptide fragments are also encompassed by the invention.

Representative examples of polypeptide residue fragments of the invention including, for example, fragments from about amino acid number 1–20, 1–66, 5–108, 5–128, 21–40, 40–108, 41–60, 47–108, 47–128, 61–80, 65–108, 65–128, 81–100, 88–108, 88–128, 108–120; 114–128; and 101 to the end of the galectin 11 polypeptide depicted in FIG. 1 (SEQ ID NO:2). In this context, "about" includes the particularly recited ranges larger or smaller by several, 5, 4, 3, 2, or 1 amino acid at either end or at both extremes.

As one of skill in the art will appreciate, galectin 11 polypeptides of the present invention such as, for example, epitope-bearing fragments of galectin 11, can be combined with parts of the constant domain of immunoglobulins (IgG), resulting in chimeric polypeptides. Fusion proteins that have a disulfide-linked dimeric structure due to the IgG part can also be more efficient in binding and neutralizing other molecules than the monomeric galectin 11 protein or protein fragment alone (Fountoulakis et al., J. Biochem. 270:3958–3964 (1995)).

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Polypeptides of the invention include polypeptides encoded by polynucleotides that hybridize (e.g., under stringent hybridization conditions) to the polynucleotide sequence depicted in FIG. 1 (SEQ ID NO:1), the complementary strand thereto, and/or the nucleotide sequence contained in the deposited clone. In specific embodiments, the polypeptides of the invention have galectin 11 functional and/or biological activity.

Assays for Galectin 11 Functional Activity

The functional and/or biological activity of galectin 11 polypeptides, fragments, variants, derivatives and analogs of the invention can be assayed by various methods.

For example, in one embodiment, where one is assaying for the ability to bind or compete with galectin 11 polypeptide for binding to anti-galectin 11 antibody, various immunoassays known in the art can be used, including, but not limited to, competitive and non-competitive assay systems using techniques such as radioimmunoassays, ELISA, "sandwich" immunoassays, immunoradiometric assays, and diffusion precipitin reactions, immunodiffusion assays, in situ immunoassays (using colloidal gold, enzyme or radio-isotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Many means are known in the art for detecting binding in an immunoassay and are within the scope of the present invention.

In another embodiment, the ability of galectin 11 polypeptides, fragments, variants, derivatives and analogs of the invention to bind β-galactoside sugars may be determined using, or routinely modifying, assays known in the art. For example, lactose binding activity of the expressed galectin 11 polypeptides and fragments, variants, derivatives, or analogs thereof, may be assayed by immunodetection of in situ binding activity to asialofetuin (Sigma) immobilized on nitrocellulose (Amersham) (Madsen et al., J. Biol. Chem. 270(11):5823–5829 (1995)). For example, in one assay, thirty μg of asialofetuin dissolved in 3 μl of water is spotted on a 1-cm2 strip of nitrocellulose. The nitrocellulose pieces are then placed in a 24-well tissue culture plant and incubated overnight in buffer B (58 mM $NA_2HPO_4$, 18 mM $KH_2PO_4$, 75 mM NaCl, 2 mM EDTA, and 3% BSA, pH 7.2) with constant agitation at 22° C. Following incubation, the blocking medium is aspirated and the nitrocellulose pieces are washed three times in buffer A (58 mM $Na_2HPO_4$ 18 mM $KH_22PO_4$, 75 mM NaCl, 2 mM EDTA, 4 mM β-mercaptoethanol and 0.2% BSA, pH 7.2). Cell extracts (preferably, COS cells) are prepared containing 1% BSA and either with or without 150 mM lactose (105 μl of primary extract, 15 μl of 10% BSA in buffer A and either 30 μl of 0.75 M lactose in buffer A or 30 μl of buffer A). The immobilized asialofetuin is incubated with the extracts for 2 h and washed 5 times in buffer A. The nitrocellulose pieces are then fixed in 2% formalin in PBS (58 mM Na$_2$HPO$_4$, 18 mM KH$_2$PO$_4$, 75 mM NaCl, 2 mM EDTA pH 7.2) for 1 h to prevent loss of bound galectin 11. Following extensive washing in PBS the pieces are incubated with a rabbit anti-galectin 11. Polyclonal serum (generated using techniques known in the art) diluted 1:100 in PBS for 2 h at 22° C. The pieces are then washed in PBS and incubated with peroxidase-labeled goat anti-rabbit antibodies (DAKO). Following incubation for 2 h at 22° C., the pieces are washed in PBS and the substrate is added. Nitrocellulose pieces are incubated until the color developed and the reaction is stopped by washing in distilled water.

The ability of galectin 11 polypeptides, fragments, variants, derivatives and analogs of the invention to agglutinate trypsin-treated rabbit erythrocytes can routinely be assayed using techniques known in the art.

The ability of the galectin 11 polypeptides, fragments, variants, derivatives and analogs of the invention to induce apoptosis of T-cells may be determined using, or routinely modifying, techniques described herein (see e.g., Example 5) or otherwise known in the art. See e.g., Perillo et al., Nature 378:736–739 (1995); Chinnaiyan et al., Cell 81:505–512 (1995); Boldin et al., J. Biol. Chem. 270: 7795–7798 (1995); Kischkel et al., EMBO J. 14:5579–5585 (1995); Chinnaiyan et al., J. Biol. Chem. 271:4961–4965 (1996); the contents of each of which is herein incorporated by reference in its entirety).

The galectin 11 polynucleotides and polypeptides, and fragments, variants derivatives and analogs thereof; and antibodies, agonists and antagonists thereto; can be tested in vivo for the desired therapeutic or prophylactic activity. For example, such compounds can be tested in suitable animal model systems prior to testing in humans. Such animal models include, but are not limited to, rats, mice, chickens, cows, monkeys, rabbits, etc. Such testing may also be utilized to routinely determine dosage for delivery to human patients. For in vivo testing prior to administration to human, any animal model system known in the art may be used (see, for example, Levi et al., Eur. J. Imun. 13:500–507 (1983); and Offner et al., J. Neuroimmunol 28:177–184 (1990)). For example, an animal model useful for the study of the treatment of human MS is experimental allergic encephalomyelitis (EAE). EAE is an experimentally induced disease that shares many of the same clinical and pathological symptoms of MS (Martin et al., Ann. Rev. Immunol. 10:153–187 (1992); Hafler et al., Immunology Today 10: 104–107 (1989)). Several studies in rodents have shown that, similar to MS, CD4+ T cells participate in the pathophysiology of EAE, Traugott et al., Cellular Immunology 91:240–254 (1985); Ben-Nun, Eur. J. Immunol. 11:195–199 (1981); Pettinel et al., J. Immunol. 127:1420–1423 (1981). EAE can be induced in certain strains of mice by immunization with myelin in an adjuvant. The immunization activates CD4+ T cells specific for myelin basic protein (MBP) and proteolipid (PLP), Bernard et al., J. Immunol. 114:1537–1540 (1975); Chou et al., J. Immunol. 130:2183–2186 (1983); Kurchroo et al., J. Immunol. 148: 3776–3782 (1992). The activated T cells enter the central nervous system and their local action causes both the anatomic pathology and clinical signs, e.g., ascending hind limb paresis leading to paralysis, of the disease. As discussed above, the galectin 1 has been demonstrated to suppress clinical and histological signs of experimental autoimmune encephalomyelitis in rats (Offner et al., J. Neuroimmunol. 28:177–184 (1990)).

Another model system that may be utilized to both study the role of the polypeptides, variants, derivatives and analogs of the invention as a suppresser of immune responses, and to determine effective dosages for doing so, is experimental autoimmune myasthenia gravis (EAMG) in rabbits. EAMG is an autoimmune disease induced by immunization with the purified acetylcholine receptor protein (AChR) and is considered to be a good model for the human disease myasthenia gravis. As further discussed above, galectin 1 has been demonstrated to have a prophylactic and therapeutic action on experimental autoimmune myasthenia gravis in rabbits (Levi et al., Eur. J. Immunol. 13:500–507 (1983)).

Other art known model assays that may be used to determine the desired therapeutic or prophylactic activity of compounds of the invention (e.g., as a suppresser of immune responses) include, but are not limited to, T-cell proliferation in mixed lymphocyte reaction assays (an art-accepted model for allogeneic graft rejection), and murine allograft models known in the art.

Assays described herein or otherwise known in the art may be applied to routinely determine which galectin 11 polypeptides, fragments, variants, derivatives and analogs of the invention demonstrate galectin 11 functional activity and the optimal concentration at which these compounds demonstrate this activity. These assays may additionally be utilized to identify molecules which enhance (agonists) or suppress (antagonists) galectin 11 functional activity.

Epitopes

The present invention encompasses polypeptides comprising, or alternatively consisting of, an epitope of the polypeptide having an amino acid sequence of SEQ ID NO:2, 25, or 27, or an epitope of the polypeptide sequence encoded by a polynucleotide sequence contained in ATCC Deposit No: 209053 or encoded by a polynucleotide that hybridizes to the complement of the sequence of SEQ ID NO:1, 24, or 26 or contained in ATCC Deposit No: 209053 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1, 24, or 26), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

Antigenic epitope-bearing peptides and polypeptides of the invention are therefore useful, for example, to raise antibodies, including monoclonal antibodies, that bind specifically to a polypeptide of the invention. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Antigenic epitope-bearing peptides and polypeptides of the invention preferably contain a sequence of at least 7, 9, 15, 20, 25, 30, 35, 40, 45, 50, 75, 100, 110 or 120 contiguous amino acid residues of the amino acid sequence depicted in FIG. 1 or 6A–B (SEQ ID NO:2, 25, or 27). In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof.

Non-limiting examples of antigenic polypeptides or peptides that can be used to generate galectin 11-specific antibodies include: a polypeptide comprising amino acid residues from about 65–70 and 118–124 in FIG. 1 (SEQ ID NO:2). As indicated above, the inventors have determined that the above polypeptide fragments are antigenic regions of the galectin 11 protein.

The epitope-bearing peptides and polypeptides of the invention may be produced by any conventional means. See generally, Houghten, R. A., Proc. Natl. Acad. Sci. USA 82:5131–5135 (1985). This Simultaneous Multiple Peptide Synthesis (SMPS) process is further described in U.S. Pat. No. 4,631,211 to Houghten et al. (1986).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Preferred epitopes of the invention include: amino acids 65–70 and 118–124 of SEQ ID NO:2, as well as polynucleotides that encode these epitopes. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5): 489–498 (1991); Studnicka et al., Protein Engineering 7(6): 805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulin genes, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The polypeptides of the invention and their fragments, variants, derivatives or analogs, or cells expressing them, can also be used as immunogens to produce antibodies immunospecific for galectin 11 polypeptide of the invention. The term "immunospecific" means that the antibodies have substantially greater affinity for the polypeptides of the invention than their affinity for other related polypeptides in the prior art.

The term "antibody" (Ab) or "monoclonal antibody" (mAb) as used herein is meant to include intact molecules as well as fragments thereof (such as, for example, Fab, and F(ab')$_2$ fragments) which are capable of binding an antigen. Fab, Fab', and F (ab')$_2$ fragments lack the Fc fragment of intact antibody, clear more rapidly from the circulation, and may have less non-specific tissue binding of an intact antibody (Wahl et al., J. Nucl. Med. 24:316–325 (1983)).

Antibodies according to the present invention may be prepared by any of a variety of standard methods using galectin 11 immunogens of the present invention. For example, antibodies generated against full-length galectin 11 polypeptides can be obtained by administering the polypeptides or epitope-bearing fragments, variants, derivatives, analogs, or cells, to an animal, preferably a nonhuman, using routine protocols. For preparation of monoclonal antibodies, any technique which provides antibodies produced by continuous cell line cultures can be used. Examples include the hybridoma technique (Kohler et al., Nature 256:495–497 (1975)), the trioma technique, the human B-cell hybridoma technique (Kozbor et al., Immunology Today 4:72 (1983)) and the EBV-hybridoma technique (Cole et al., MONOCLONAL ANTIBODIES AND CANCER THERAPY, pp. 77–96, Alan R. Liss, Inc., 1985). Additionally, techniques for the production of single chain antibodies (U.S. Pat. No. 4,946,778) can also be adapted to produce single chain antibodies to polypeptides of the invention. Also, transgenic mice, or other organisms including other mammals, may be used to express humanized antibodies.

Antibodies of the invention can be used in methods known in the art relating to the localization and activity of the polypeptide sequences of the invention, e.g., for imaging these polypeptides, measuring levels thereof in appropriate physiological samples, etc. The antibodies also have use in immunoassays and in therapeutics as agonists and antagonists of galectin 11. Additionally, the antibodies of the invention may be employed to isolate or to identify clones expressing the polypeptide or to purify the polypeptides by affinity chromatography.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242: 1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101(1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt- cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel. The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2, 25, or 27 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive materials include radioisotopes such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.,* 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell,* 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^{3}$H or $^{125}$I) in the presence of increasing amounts of an unlabeled second antibody. Other suitable radioactive materials include, but are not limited to, radioisotopes such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92 m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Diagnosis and Prognosis

It is believed that certain tissues in mammals with certain diseases (e.g., autoimmune diseases which include, but are not limited to, lupus erythematosus (SLE), rheumatoid arthritis (RA), insulin-dependent diabetes, multiple sclerosis (MS), giant cell arteritis, polyarteritis nodosa, myasthenia gravis, scleroderma, and graft versus host disease; graft rejection; mammalian cancers which include, but are not limited, to, melanoma, renal astrocytoma, Hodgkin's disease, breast, ovarian, prostate, bone, liver, lung, pancreatic, and spleenic cancers; inflammatory diseases; asthma; and allergeic diseases) express significantly altered (e.g., enhanced or decreased) levels of the galectin 11 polypeptide and mRNA encoding the galectin 11 polypeptide when compared to a corresponding "standard" mammal, i.e., a mammal of the same species not having the disease. Further, it is believed that altered levels of the galectin 11 polypeptide can be detected in certain body fluids (e.g., sera, plasma, urine, and spinal fluid) from mammals with the disorder when compared to sera from mammals of the same species not having the disorder. Thus, the invention provides a diagnostic method useful during diagnosis, which involves assaying the expression level of the gene encoding the galectin 11 polypeptide in mammalian cells or body fluid and comparing the gene expression level with a standard galectin 11 gene expression level, whereby an increase or decrease in the gene expression level over the standard is indicative of the disease.

Where a diagnosis has already been made according to conventional methods, the present invention is useful as a prognostic indicator, whereby patients exhibiting altered galectin 11 gene expression will experience a worse clinical outcome relative to patients expressing the gene at a normal level.

By "assaying" the expression level of the gene encoding the galectin 11 polypeptide" is intended qualitatively or quantitatively measuring or estimating the level of the galectin 11 polypeptide or the level of the mRNA encoding the galectin 11 polypeptide in a first biological sample either directly (e.g., by determining or estimating absolute polypeptide or mRNA level) or relatively (e.g., by comparing to the galectin 11 polypeptide level or mRNA level in a second biological sample).

Nucleic acids for diagnosis may be obtained from a biological sample of a subject, such as from blood, urine, saliva, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled galectin 11 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science 230:1242 (1985)). Sequence changes at specific locations may also be revealed by nuclease protection assays, such as RNase and S1 protection or the chemical cleavage method (see Cotton et al., Proc. Natl. Acad. Sci. USA 85:4397–4401 (1985)). In another embodiment, an array of oligonucleotides probes comprising galectin 11 polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., Science 274:610–613 (1996)).

The diagnostic assays offer a process for diagnosing or determining a susceptibility to specific diseases through detection of mutation in the galectin 11 gene by the methods described.

In addition, specific diseases can be diagnosed by methods comprising determining from a sample derived from a subject an abnormally decreased or increased level of galectin 11 polypeptide or mRNA. Decreased or increased expression can be measured at the RNA level using any of the methods well known in the art, which include, but are not limited to, Northern blot analysis, (Harada et al., Cell 63:303–312 (1990), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., Technique 2:295–301 (1990), reverse transcription in combination with the ligase chain reaction (RT-LCR) and other hybridization methods.

Assaying galectin 11 polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, galectin 11 polypeptide expression in tissues can be studied with classical immunohistological methods (Jalkanen et al., J. Cell. Biol. 101: 976–985 (1985); Jalkanen et al., J. Cell. Biol. 105:3087–3096 (1987)).

Suitable labels are known in the art and include enzyme labels, such as, Glucose oxidase, and radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Thus in another aspect, the present invention relates to a diagnostic kit for a disease or susceptibility to a disease which comprises:

(a) a galectin 11 polynucleotide, preferably the nucleotide sequence of SEQ ID NO:1, 24, or 26, or a fragment thereof;

(b) a nucleotide sequence complementary to that of (a);

(c) a galectin 11 polypeptide of the invention, preferably the polypeptide of SEQ ID NO:2, 25, or 27 or a fragment thereof; or (d) an antibody to a galectin 11 polypeptide of the invention, preferably to the polypeptide of SEQ ID NO: 2, 25, or 27.

It will be appreciated that in any such kit, (a), (b), (c) or (d) may comprise a substantial component.

Thus, the invention also provides a diagnostic method useful during diagnosis of a disorder, involving measuring the expression level of polynucleotides of the present invention in cells or body fluid from an individual and comparing the measured gene expression level with a standard level of polynucleotide expression level, whereby an increase or decrease in the gene expression level compared to the standard is indicative of a disorder.

In still another embodiment, the invention includes a kit for analyzing samples for the presence of proliferative and/or cancerous polynucleotides derived from a test subject. In a general embodiment, the kit includes at least one polynucleotide probe containing a nucleotide sequence that will specifically hybridize with a polynucleotide of the present invention and a suitable container. In a specific embodiment, the kit includes two polynucleotide probes defining an internal region of the polynucleotide of the present invention, where each probe has one strand containing a 31'mer-end internal to the region. In a further embodiment, the probes may be useful as primers for polymerase chain reaction amplification.

Where a diagnosis of a disorder, has already been made according to conventional methods, the present invention is useful as a prognostic indicator, whereby patients exhibiting enhanced or depressed polynucleotide of the present invention expression will experience a worse clinical outcome relative to patients expressing the gene at a level nearer the standard level.

By "measuring the expression level of polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of individuals not having a disorder. As will be appreciated in the art, once a standard polypeptide level or mRNA level is known, it can be used repeatedly as a standard for comparison.

By "biological sample" is intended any biological sample obtained from an individual, body fluid, cell line, tissue culture, or other source which contains the polypeptide of the present invention or mRNA. As indicated, biological samples include body fluids (such as semen, lymph, sera, plasma, urine, synovial fluid and spinal fluid) which contain the polypeptide of the present invention, and other tissue sources found to express the polypeptide of the present invention. Methods for obtaining tissue biopsies and body fluids from mammals are well known in the art. Where the biological sample is to include mRNA, a tissue biopsy is the preferred source.

The method(s) provided above may preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject.

The knowledge of such polymorphisms (i.e. their location, as well as, their existence) would be beneficial in identifying disease loci for many disorders, including cancerous diseases and conditions. Such a method is described in U.S. Pat. Nos. 5,858,659 and 5,856,104. The US Patents referenced supra are hereby incorporated by reference in their entirety herein.

Screening Assays for Galectin 11 Agonists or Antagonists

Aberrancies in galectin 11 expression are responsible for many biological functions, including many pathologies. Accordingly, it is desirous to find compounds and drugs which enhance galectin 11 activity or, alternatively, suppress galectin 11 activity. The invention also provides a method of screening compounds to identify those which enhance or suppress galectin 11 activity. An agonist is a compound which increases the natural biological functions of galectin 11 or which functions in a manner similar to galectin 11, while antagonists decrease or eliminate such functions.

Thus, embodiments of the invention are directed to assays designed to identify compounds that interact with (e.g., bind to) galectin 11 polypeptides of the invention, compounds that interfere or enhance the interaction of galectin 11 with its cognate ligands, and to compounds which modulate the galectin 11 gene (i.e., modulate the level of galectin 11 gene expression) or modulate the level of galectin 11 functional or biological activity. Assays may also be used to identify compounds which bind galectin 11 gene regulatory sequences (e.g., promoter sequences) and which may modulate galectin 11 gene expression. See e.g., Platt, J. Biol. Chem. 269:28558–28562 (1994), which is incorporated herein by reference in its entirety.

Thus, polypeptides of the invention may be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., Current Protocols in Immunology 1(2):Chapter 5 (1991). Further examples of compounds that may be screened include, but are not limited to, peptides such as, for example soluble peptides, including but not limited to, those found: in random peptide libraries (see, e.g., Lam et al., Nature 354:84–86 (1991)), and combinatorial chemistry-derived molecular libraries made of D- and L-configuration amino acid; phosphopeptides (including, but not limited to, members of random or partially degenerate, directed phosphopeptide libraries (see e.g., Songyang et al., Cell 72:767–778 (1993)); antibodies (including but not limited to, monoclonal, humanized, anti-idiotypic, chimeric or single chain antibodies, and Fab, F(ab')2, and FAB expression library fragments, and epitope-binding fragments thereof); and small organic or inorganic molecules.

Numerous experimental methods may be used to select and detect compounds that bind galectin 11 polypeptides of the invention and thereby modulate galectin 11 expression or activity, including, but not limited to, protein affinity chromotography, affinity blotting, immunoprecipitation, cross-linking, and library based methods such as protein probing, phage display, the two-hybrid system (Fields and Song, Nature 340:245–246 (1989)), and modified versions of the two-hybrid system (Gyuris et al., Cell 75:791–803 (1993); Zervos et al., Cell 72:223–232 (1993)). See generally, Phizicky et al., Microbiol. Rev. 59:94–123 (1995).

The principle behind assays that identify compounds that bind to galectin 11 polypeptides of the invention involves preparing a reaction mixture of galectin 11 polypeptide and test compound under conditions that allow the two components to interact and bind, thus forming a complex which can be detected in the reaction mixture and purified using techniques known in the art. Accordingly, the assays may simply test binding of a candidate compound to galectin 11.

Further, the assays may simply comprise the steps of combining a candidate compound with a solution containing a galectin 11 polypeptide to form a mixture, and determining the ability of galectin 11 contained in this mixture to bind galectin 11 cognate ligands (e.g., compounds containing a β galactoside sugar and/or molecules expressed on the surface of T-cells), to agglutinate trypsin-treated rabbit erythrocytes, or to induce apoptosis of T-cells, and comparing this ability with that observed for the galectin 11 polypeptide in the same or similar solution under the same or similar conditions, but absent the candidate compound. The ability of the candidate molecule to interfere with binding of galectin 11 to the cognate ligand is reflected in decreased binding of the labeled galectin 11 to the cognate ligand relative to that in the absence of candidate molecule. Molecules which interfere with the ability of galectin 11 to elicit cellular responses (e.g., apoptosis) resulting from galectin 11 binding to its cognate ligand are antagonists. Molecules that enhance galectin 11 induced cellular responses when mixed with galectin 11, or which are able to induce a similar cellular response in the absence of galectin 11, are agonists.

The galectin 11 polynucleotides, polypeptides, and antibodies of the invention may also be used to configure assays for detecting the effect of added compounds on the production of galectin 11 mRNA and protein in cells. For example, an ELISA may be constructed for measuring secreted or cell associated levels of galectin 11 protein using monoclonal and polyclonal antibodies by standard methods known in the art, and this can be used to discover agents which may inhibit or enhance the production of galectin 11 (also called antagonist or agonist, respectively) from suitably manipulated cells or tissues. Standard methods for conducting screening assays are well understood in the art.

Examples of potential galectin 11 antagonists include antibodies or, in some cases, oligonucleotides or proteins which are closely related to the galectin 11 or its cognate ligand, e.g., a fragment of galectin 11 or galectin 11 ligand, or small molecules which bind to the cognate ligand, but do not elicit a response, so that the activity of the galectin 11 is prevented.

Thus in another aspect, the present invention relates to a screening kit for identifying agonists, antagonists, ligands, receptors, substrates, enzymes, etc. for galectin 11 polypeptides; or compounds which decrease or enhance the production of galectin 11, which comprises:

(a) a galectin 11 polypeptide of the invention, such as, for example, that of SEQ ID NO:2, 25, or 27;

(b) a cell expressing a galectin 11 ligand, such as, for example, a T-cell;

(c) a cell membrane expressing a galectin 11 ligand, preferably a membrane of a T-cell;

(d) a compound containing a β galactoside sugar; or (e) antibody to a galectin 11 polypeptide of the invention, preferably that of SEQ ID NO: 2, 25, or 27.

It will be appreciated that in any such kit, (a), (b), (c), (d), or (e) may comprise a substantial component.

Compounds identified via assays such as those described herein, may be useful, for example, in elaborating the biological function of the galectin 11 gene product and for regulating cell growth, cell proliferation and differentiation, and apoptosis. For example, antibodies against galectin 11 and galectin 11 polypeptides, fragments, derivatives, variants or analogs of the invention may be employed to suppress galectin 11 activity to treat abnormalities resulting from elevated galectin 11. The combination of these identified compounds with a pharmaceutically acceptable carrier (e.g., as described herein) and their administration to treat or prevent growth regulatory and immunomodulatory disorders, including, but not limited to, autoimmune diseases, cancer, and inflammatory diseases, are also encompassed by the invention.

Prophylactic and Therapeutic Methods

It is to be understood that although the following discussion is specifically directed to human patients, the teachings are also applicable to any animal that expresses galectin 11.

As noted above, galectin 11 shares significant homology with other galectins. Additionally, as disclosed herein, galectin 11, like galectin 1 induces apoptosis of T-cell lines. Further, as discussed above, galectin 1 has been demonstrated to play a role in regulating cell proliferation and some immune functions (e.g., therapeutic activity against autoimmune diseases in experimental myasthenia gravis and experimental autoimmune encephalomyelitis animal model systems). Thus, it is likely that galectin 11, like galectin 1, is active in modulating growth regulatory activities (e.g., cell differentiation and/or cell proliferation), immunomodulatory activity, cell-cell and cell-substrate interactions, and apoptosis.

Apoptosis, or programmed cell death, is a physiological mechanism involved in the deletion of peripheral T lymphocytes of the immune system, and its dysregulation can lead to a number of different pathogenic processes. Diseases associated with increased cell survival, or the inhibition of apoptosis, that could be treated or detected by galectin 11 polynucleotides or polypeptides, as well as antagonists or agonists of galectin 11, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, galectin 11 polynucleotides, polypeptides, and/or antagonists of the invention are used to inhibit growth, progression, and/or metasis of cancers, in particular those listed above.

Additional diseases or conditions associated with increased cell survival that could be treated or detected by galectin 11 polynucleotides or polypeptides, or agonists or antagonists of galectin 11, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated or detected by galectin 11 polynucleotides or polypeptides, as well as agonists or antagonists of galectin 11, include AIDS; neurodegenerative disorders (such as Alzheimer's disease, Parkinson's disease, Amyotrophic lateral sclerosis, Retinitis pigmentosa, Cerebellar degeneration and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Any method which neutralizes or enhances galectin 11 activity can be used to modulate growth regulatory activities (e.g., cell proliferation), immunomodulatory activity, cell-cell and cell-substrate interactions, and apoptosis.

Galectin 11 polypeptides or polynucleotides (including galectin 11 fragments, variants, derivatives, and anaologs, and galectin 11 agonists and antagonists as described herein) may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, galectin 11 polynucleotides or polypeptides can be used as a marker or detector of a particular immune system disease or disorder.

Galectin 11 polynucleotides or polypeptides (including galectin 11 fragments, variants, derivatives, and anaologs, and galectin 11 agonists and antagonists as described herein) may be useful in treating or detecting deficiencies or disorders of hematopoietic cells. As further discussed below, galectin 11 polypeptides or polynucleotides or agonists or antagonists of galectin 11, could be used to increase differentiation and proliferation of hematopoietic cells, including the pluripotent stem cells, in an effort to treat those disorders associated with a decrease in certain (or many) types hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, galectin 11 polypeptides or polynucleotides (including galectin 11 fragments, variants, derivatives, and anaologs, and galectin 11 agonists and antagonists as described herein) can also be used to modulate hemostatic (the stopping of bleeding) or thrombolytic activity (clot formation). For example, by increasing hemostatic or thrombolytic activity, galectin 11 polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, galectin 11 polynucleotides or polypeptides, or agonists or antagonists of galectin 11, that can decrease hemostatic or thrombolytic activity could be used to inhibit or dissolve clotting. These molecules could be important in the treatment of heart attacks (infarction), strokes, or scarring.

Galectin 11 polynucleotides or polypeptides (including galectin 11 fragments, variants, derivatives, and anaologs), and galectin 11 agonists or antagonists (as described herein) may also be useful in treating or detecting autoimmune disorders. As disclosed herein, galectin 11 induces apoptosis of T-cell lines (see Example 5, FIGS. 5A and 5B). Many autoimmune disorders result from inappropriate recognition of self as foreign material by immune cells. This inappropriate recognition results in an immune response leading to the destruction of the host tissue. Therefore, the administration of galectin 11 polypeptides or polynucleotides that can inhibit an immune response, particularly the proliferation, differentiation, or chemotaxis of T-cells, may be an effective therapy in preventing autoimmune disorders.

Examples of autoimmune disorders that can be treated or detected include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated by galectin 11 polypeptides or polynucleotides, or agonists or antagonists of galectin 11. Moreover, these molecules can be used to treat anaphylaxis, hypersensitivity to an antigenic molecule, or blood group incompatibility.

Galectin 11 polynucleotides or polypeptides (including galectin 11 fragments, variants, derivatives, and anaologs, and galectin 11 agonists or antagonists as described herein) may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of galectin 11 polypeptides or polynucleotides, or agonists or antagonists of galectin 11, that inhibits an immune response, particularly the proliferation, differentiation, or chemotaxis of T-cells, may be an effective therapy in preventing organ rejection or GVHD.

Similarly, galectin 11 polypeptides or polynucleotides (including galectin 11 fragments, variants, derivatives, and anaologs, and galectin 11 agonists or antagonists as described herein) may also be used to modulate inflammation. For example, galectin 11 polypeptides or polynucleotides, or agonists or antagonists of galectin 11, may inhibit the proliferation and differentiation of cells involved in an inflammatory response. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1).

Galectin 11 polypeptides or polynucleotides (including galectin 11 fragments, variants, derivatives, and anaologs, and galectin 11 agonists and antagonists as described herein) can be used to treat or detect hyperproliferative disorders, including neoplasms. Galectin 11 polypeptides or polynucleotides, or agonists or antagonists of galectin 11, may inhibit the proliferation of the disorder through direct or indirect interactions. Alternatively, galectin 11 polypeptides or polynucleotides, or agonists or antagonists of galectin 11, may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by galectin 11 polynucleotides or polypeptides include, but are not limited to, neoplasms located in the: colon, abdomen, bone, breast, digestive system, liver, pancreas, prostate, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative disorders can also be treated or detected by galectin 11 polynucleotides or polypeptides, or agonists or antagonists of galectin 11. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating cell proliferative disorders by inserting into an abnormally proliferating cell a polynucleotide of the present invention, wherein said polynucleotide represses said expression.

Another embodiment of the present invention provides a method of treating cell-proliferative disorders in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the poynucleotides of the present invention is inserted into cells to be treated utilizing a retrovirus, or more preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating one or more of the described disorders. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating a subject having or developing cell proliferative and/or differentiation disorders as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions, thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Moreover, polypeptides of the present invention are useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph IB, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et. al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuviants, such as apoptonin, galectins, thioredoxins, anti-inflammatory proteins (See for example, Mutat Res 400 (1–2):447–55 (1998), Med Hypotheses. 50(5):423–33 (1998), Chem Biol Interact. April 24; 111–112:23–34 (1998), J Mol Med. 76(6):402–12 (1998), Int J Tissue React; 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewere herein, or indirectly, such as activating the expression of proteins known to inhibit metastasis, for example alpha 4 integrins, (See, e.g., Curr Top Microbiol Immunol 1998; 231:125–41, which is hereby incorporated by reference). Such thereapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodes associated with heterologous polypeptides, heterologous nucleic acids, toxins, or pro-drugs) to targeted cells expressing the polypeptide of the present invention. Polypeptides or polypeptide antibodes of the invention may be associated with with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Galectin 11 polypeptides or polynucleotides (including galectin 11 fragments, variants, derivatives, and anaologs, and galectin 11 agonists and antagonists as described herein) can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, galectin 11 polypeptides or polynucleotides may also directly inhibit the infectious agent, without necessarily eliciting an immune response.

Viruses are one example of an infectious agent that can cause disease or symptoms that can be treated or detected by galectin 11 polynucleotides or polypeptides. Examples of viruses, include, but are not limited to, the following DNA and RNA viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. Galectin 11 polypeptides or polynucleotides, or agonists or antagonists of the invention, can be used to treat or detect any of these symptoms or diseases. In specific embodiments, polynucleotides, polypeptides, or agonists or antagonists of the invention are used to treat: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat AIDS.

Similarly, bacterial or fungal agents that can cause disease or symptoms and that can be treated or detected by galectin 11 polynucleotides or polypeptides and/or agonist or antagonists of the present invention, include, but are not limited to, the following Gram-Negative and Gram-positive bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g.,

*Borrelia burgdorferi*), Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Kiebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria*, Mycoplasmatales, *Mycobacterium leprae, Vibrio cholerae*, Neisseriaceae (e.g., Acinetobacter, Gonorrhea, Menigococcal), Meisseria meningitidis, Pasteurellacea Infections (e.g., Actinobacillus, Heamophilus (e.g., Heamophilus influenza type B), Pasteurella), Pseudomonas, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Galectin 11 polypeptides or polynucleotides, or agonists or antagonists of the invention, can be used to treat or detect any of these symptoms or diseases. In specific embodiments, polynucleotides, polypeptides, agonists or antagonists of the invention are used to treat: tetanus, Diptheria, botulism, and/or meningitis type B.

Moreover, parasitic agents causing disease or symptoms that can be treated or detected by galectin 11 polynucleotides or polypeptides, agonists or antagonists, include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. Galectin 11 polypeptides or polynucleotides, or agonists or antagonists, can be used to treat or detect any of these symptoms or diseases. In specific embodiments, polynucleotides, polypeptides, or agonists or antagonists of the invention are used to treat malaria.

Preferably, treatment using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Galectin 11 polynucleotides or polypeptides (including galectin 11 fragments, variants, derivatives, and anaologs, and galectin 11 agonists and antagonists as described herein) can be used to differentiate, proliferate, and attract cells, leading to the regeneration of tissues. (See, Science 276: 59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis.

Moreover, galectin 11 polynucleotides or polypeptides (including galectin 11 fragments, variants, derivatives, and anaologs, and galectin 11 agonists and antagonists as described herein) may increase regeneration of tissues difficult to heal. For example, increased tendon/ligament regeneration would quicken recovery time after damage. Galectin 11 polynucleotides or polypeptides, or agonists or antagonists of the present invention could also be used prophylactically in an effort to avoid damage. Specific diseases that could be treated include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using galectin 11 polynucleotides or polypeptides, or agonists or antagonists of the present invention, to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the galectin 11 polynucleotides or polypeptides or agonists or antagonists of galectin 11.

Galectin 11 polynucleotides or polypeptides, or agonists or antagonists of the present invention, may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

Galectin 11 polynucleotides or polypeptides, or agonists or antagonists of the present invention, may increase chemotaxic activity of particular cells. These chemotactic molecules can then be used to treat inflammation, infection, hyperproliferative disorders, or any immune system disorder by increasing the number of cells targeted to a particular location in the body. For example, chemotaxic molecules can be used to treat wounds and other trauma to tissues by attracting immune cells to the injured location. Chemotactic molecules of the present invention can also attract fibroblasts, which can be used to treat wounds.

It is also contemplated that galectin 11 polynucleotides or polypeptides, or agonists or antagonists of the present invention, may inhibit chemotactic activity. These molecules could also be used to treat disorders. Thus, galectin 11 polynucleotides or polypeptides, or agonists or antagonists of the present invention, could be used as an inhibitor of chemotaxis.

Nervous system disorders, which can be treated with the galectin 11 compositions of the invention (e.g., galectin 11 polypeptides, polynucleotides, and/or agonists or antagonists), include, but are not limited to, nervous system injuries, and diseases or disorders which result in either a disconnection of axons, a diminution or degeneration of neurons, or demyelination. Nervous system lesions which may be treated in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the galectin 11 polypeptides, polynucleotides, or agonists or antagonists of the present invention are used to protect neural cells from the damaging effects of cerebral hypoxia. According to this embodiment, the galectin 11 compositions of the invention are used to treat or prevent neural cell injury associated with cerebral hypoxia. In one aspect of this embodiment, the galectin 11 polypeptides, polynucleotides, or agonists or antagonists of the invention are used to treat or prevent neural cell injury associated with cerebral ischemia. In another aspect of this embodiment, the galectin 11 polypeptides, polynucleotides, or agonists or antagonists of the present invention are used to treat or prevent neural cell injury associated with cerebral infarction. In another aspect of this embodiment, the galectin 11 polypeptides, polynucleotides, or agonists or antagonists of the present invention are used to treat or prevent neural cell injury associated with a stroke. In a further aspect of this embodiment, the galectin 11 polypeptides, polynucleotides, or agonists or antagonists of the present invention are used to treat or prevent neural cell injury associated with a heart attack.

The compositions of the invention which are useful for treating or preventing a nervous system disorder may be selected by testing for biological activity in promoting the survival or differentiation of neurons. For example, and not by way of limitation, galectin 11 compositions of the invention which elicit any of the following effects may be useful according to the invention: (1) increased survival time, of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron disorders that may be treated according to the invention include, but are not limited to, disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease). Additional examples of neurologic diseases which can be treated or detected with polynucleotides, polypeptides, agonists, and/or antagonists of the present invention include brain diseases, such as metabolic brain diseases which includes phenylketonuria such as maternal phenylketonuria, pyruvate carboxylase deficiency, pyruvate dehydrogenase complex deficiency, Wernicke's Encephalopathy, brain edema, brain neoplasms such as cerebellar neoplasms which include infratentorial neoplasms, cerebral ventricle neoplasms such as choroid plexus neoplasms, hypothalamic neoplasms, supratentorial neoplasms, canavan disease, cerebellar diseases such as cerebellar ataxia which include spinocerebellar degeneration such as ataxia telangiectasia, cerebellar dyssynergia, Friederich's Ataxia, Machado-Joseph Disease, olivopontocerebellar atrophy, cerebellar neoplasms such as infratentorial neoplasms, diffuse cerebral sclerosis such as encephalitis periaxialis, globoid cell leukodystrophy, metachromatic leukodystrophy and subacute sclerosing panencephalitis, cerebrovascular disorders (such as carotid artery diseases which include carotid artery thrombosis, carotid stenosis and Moyamoya Disease, cerebral amyloid angiopathy, cerebral aneurysm, cerebral anoxia, cerebral arteriosclerosis, cerebral arteriovenous malformations, cerebral artery diseases, cerebral embolism and thrombosis such as carotid artery thrombosis, sinus thrombosis and Wallenberg's Syndrome, cerebral hemorrhage such as epidural hematoma, subdural hematoma and subarachnoid hemorrhage, cerebral infarction, cerebral ischemia such as transient cerebral ischemia, Subclavian Steal Syndrome and vertebrobasilar insufficiency, vascular dementia such as multi-infarct dementia, periventricular leukomalacia, vascular headache such as cluster headache, migraine, dementia such as AIDS Dementia Complex, presenile dementia such as Alzheimer's Disease and Creutzfeldt-Jakob Syndrome, senile dementia such as Alzheimer's Disease and progressive supranuclear palsy, vascular dementia such as multi-infarct dementia, encephalitis which include encephalitis periaxialis, viral encephalitis such as epidemic encephalitis, Japanese Encephalitis, St. Louis Encephalitis, tick-borne encephalitis and West Nile Fever, acute disseminated encephalomyelitis, meningoencephalitis such as uveomeningoencephalitic syndrome, Postencephalitic Parkinson Disease and subacute sclerosing panencephalitis, encephalomalacia such as periventricular leukomalacia, epilepsy such as generalized epilepsy which includes infantile spasms, absence epilepsy, myoclonic epilepsy which includes MERRF Syndrome, tonic-clonic epilepsy, partial epilepsy such as complex partial epilepsy, frontal lobe epilepsy and temporal lobe epilepsy, post-traumatic epilepsy, status epilepticus such as Epilepsia Partialis Continua, Hallervorden-Spatz Syndrome, hydrocephalus such as Dandy-Walker Syndrome and normal pressure hydrocephalus, hypothalamic diseases such as hypothalamic neoplasms, cerebral malaria, narcolepsy which includes cataplexy, bulbar poliomyelitis, cerebri pseudotumor, Rett Syndrome, Reye's Syndrome, thalamic diseases, cerebral toxoplasmosis, intracranial tuberculoma and Zellweger Syndrome, central nervous system infections such as AIDS Dementia Complex, Brain Abscess, subdural empyema, encephalomyelitis such as Equine Encephalomyelitis, Venezuelan Equine Encephalomyelitis, Necrotizing Hemorrhagic Encephalomyelitis, Visna, cerebral malaria, meningitis such as arachnoiditis, aseptic meningitis such as viral meningitis which includes lymphocytic choriomeningitis. Bacterial meningitis which includes Haemophilus Meningtitis, Listeria Meningtitis, Meningococcal Meningtitis such as Waterhouse-Friderichsen Syndrome, Pneumococcal Meningtitis and meningeal tuberculosis, fungal meningitis such as Cryptococcal Meningtitis, subdural effusion, meningoencephalitis such as uvemeningoencephalitic syndrome, myelitis such as transverse myelitis, neurosyphilis such as tabes dorsalis, poliomyelitis which includes bulbar poliomyelitis and postpoliomyelitis syndrome, prion diseases (such as Creutzfeldt-Jakob Syndrome, Bovine Spongiform Encephalopathy, Gerstmann-Straussler Syndrome, Kuru, Scrapie) cerebral toxoplasmosis, central nervous system neoplasms such as brain neoplasms that include cerebellear neoplasms such as infratentorial neoplasms, cerebral ventricle neoplasms such as choroid plexus neoplasms, hypothalamic neoplasms and supratentorial neoplasms, meningeal neoplasms, spinal cord neoplasms which include epidural neoplasms, demyelinating diseases such as Canavan Diseases, diffuse cerebral sceloris which includes adrenoleukodystrophy, encephalitis periaxialis, globoid cell leukodystrophy, diffuse cerebral sclerosis such as metachromatic leukodystrophy, allergic encephalomyelitis, necrotizing hemorrhagic encephalomyelitis, progressive multifocal leukoencephalopathy, multiple sclerosis, central pontine myelinolysis, transverse myelitis, neuromyelitis optica, Scrapie, Swayback, Chronic Fatigue Syndrome, Visna, High Pressure Nervous Syndrome, Meningism, spinal cord diseases such as amyotonia congenita, amyotrophic lateral sclerosis, spinal muscular atrophy such as Werdnig-Hoffmann Disease, spinal cord compression, spinal cord neoplasms such as epidural neoplasms, syringomyelia, Tabes Dorsalis, Stiff-Man Syndrome, mental retardation such as Angelman Syndrome, Cri-du-Chat Syndrome, De Lange's Syndrome, Down Syndrome, Gangliosidoses such as gangliosidoses G(M1), Sandhoff Disease, Tay-Sachs Disease, Hartnup Disease, homocystinuria, Laurence-Moon-Biedl Syndrome, Lesch-Nyhan Syndrome, Maple Syrup Urine Disease, mucolipidosis such as fucosidosis, neuronal ceroid-lipofuscinosis, oculocerebrorenal syndrome, phenylketonuria such as maternal phenylketonuria, Prader-Willi Syndrome, Rett Syndrome, Rubinstein-Taybi Syndrome, Tuberous Sclerosis, WAGR Syndrome, nervous system abnormalities such as holoprosencephaly, neural tube defects such as anencephaly which includes hydrangencephaly, Arnold-Chairi Deformity, encephalocele, meningocele, meningomyelocele, spinal dysraphism such as spina bifida cystica and spina bifida occulta, hereditary motor and sensory neuropathies which include Charcot-Marie Disease, Hereditary optic atrophy, Refsum's Disease, hereditary spastic paraplegia, Werdnig-Hoffmann Disease, Hereditary Sensory and Autonomic Neuropathies such as Congenital Analgesia and Familial Dysautonomia, Neurologic manifestations (such as agnosia that include Gerstmann's Syndrome, Amnesia such as retrograde amnesia, apraxia, neurogenic bladder, cataplexy, communicative disorders such as hearing disorders that includes deafness, partial hearing loss, loudness recruitment and tinnitus, language disorders such as aphasia which include agraphia, anomia, broca aphasia, and Wernicke Aphasia, Dyslexia such as Acquired Dyslexia, language development disorders, speech disorders such as aphasia which includes anomia, broca aphasia and Wernicke Aphasia, articulation disorders, communicative disorders such as speech disorders which include dysarthria, echolalia, mutism and stuttering, voice disorders such as aphonia and hoarseness, decerebrate state, delirium, fasciculation, hallucinations, meningism, movement disorders such as angelman syndrome, ataxia, athetosis, chorea, dystonia, hypokinesia, muscle hypotonia, myoclonus, tic, torticollis and tremor, muscle hypertonia such as muscle rigidity such as stiff-man syndrome, muscle spasticity, paralysis such as facial paralysis which includes Herpes Zoster Oticus, Gastroparesis, Hemiplegia, ophthalmoplegia such as diplopia, Duane's Syndrome, Horner's Syndrome, Chronic progressive external ophthalmoplegia such as Kearns Syndrome, Bulbar Paralysis, Tropical Spastic Paraparesis, Paraplegia such as Brown-Sequard Syndrome, quadriplegia, respiratory paralysis and vocal cord paralysis, paresis, phantom limb, taste disorders such as ageusia and dysgeusia, vision disorders such as amblyopia, blindness, color vision defects, diplopia, hemianopsia, scotoma and subnormal vision, sleep disorders such as hypersomnia which includes Kleine-Levin Syndrome, insomnia, and somnambulism, spasm such as trismus, unconsciousness such as coma, persistent vegetative state and syncope and vertigo, neuromuscular diseases such as amyotonia congenita, amyotrophic lateral sclerosis, Lambert-Eaton Myasthenic Syndrome, motor neuron disease, muscular atrophy such as spinal muscular atrophy, Charcot-Marie Disease and Werdnig-Hoffmann Disease, Postpoliomyelitis Syndrome, Muscular Dystrophy, Myasthenia Gravis, Myotonia Atrophica, Myotonia Confenita, Nemaline Myopathy, Familial Periodic Paralysis, Multiplex Paramyloclonus, Tropical Spastic Paraparesis and Stiff-Man Syndrome, peripheral nervous system diseases such as acrodynia, amyloid neuropathies, autonomic nervous system diseases such as Adie's Syndrome, Barre-Lieou Syndrome, Familial Dysautonomia, Horner's Syndrome, Reflex Sympathetic Dystrophy and Shy-Drager Syndrome, Cranial Nerve Diseases such as Acoustic Nerve Diseases such as Acoustic Neuroma which includes Neurofibromatosis 2, Facial Nerve Diseases such as Facial Neuralgia, Melkersson-Rosenthal Syndrome, ocular motility disorders which includes amblyopia, nystagmus, oculomotor nerve paralysis, ophthalmoplegia such as Duane's Syndrome, Homer's Syndrome, Chronic Progressive External Ophthalmoplegia which includes Kearns Syndrome, Strabismus such as Esotropia and Exotropia, Oculomotor Nerve Paralysis, Optic Nerve Diseases such as Optic Atrophy which includes Hereditary Optic Atrophy, Optic Disk Drusen, Optic Neuritis such as Neuromyelitis Optica, Papilledema, Trigeminal Neuralgia, Vocal Cord Paralysis, Demyelinating Diseases such as Neuromyelitis Optica and Swayback, Diabetic neuropathies such as diabetic foot, nerve compression syndromes such as carpal tunnel syndrome, tarsal tunnel syndrome, thoracic outlet syndrome such as cervical rib syndrome, ulnar nerve compression syndrome, neuralgia such as causalgia, cervico-brachial neuralgia, facial neuralgia and trigeminal neuralgia, neuritis such as experimental allergic neuritis, optic neuritis, polyneuritis, polyradiculoneuritis and radiculities such as polyradiculitis, hereditary motor and sensory neuropathies such as Charcot-Marie Disease, Hereditary Optic Atrophy, Refsum's Disease, Hereditary Spastic Paraplegia and Werdnig-Hoffmann Disease, Hereditary Sensory and Autonomic Neuropathies which include Congenital Analgesia and Familial Dysautonomia, POEMS Syndrome, Sciatica, Gustatory Sweating and Tetany).

In accordance with yet a further aspect of the present invention, there is provided a process for utilizing galectin 11 polynucleotides or polypeptides, as well as agonists or antagonists of galectin 11, for therapeutic purposes, for example, to stimulate epithelial cell proliferation and basal keratinocytes for the purpose of wound healing, and to stimulate hair follicle production and healing of dermal wounds. Galectin 11 polynucleotides or polypeptides, as well as agonists or antagonists of galectin 11, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associted with systemic treatment with steroids, radiation therapy and antineoplastic drugs and antimetabolites. Galectin 11 polynucleotides or polypeptides, as well as agonists or antagonists of galectin 11, could be used to promote dermal reestablishment subsequent to dermal loss.

Galectin 11 polynucleotides or polypeptides, as well as agonists or antagonists of galectin 11, could be used to increase the adherence of skin grafts to a wound bed and to stimulate re-epithelialization from the wound bed. The following are types of grafts that galectin 11 polynucleotides or polypeptides, agonists or antagonists of galectin 11, could be used to increase adherence to a wound bed: autografts, artificial skin, allografts, autodermic graft, autoepdermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. Galectin 11 polynucleotides or polypeptides, as well as agonists or antagonists of galectin 11, can be used to promote skin strength and to improve the appearance of aged skin.

It is believed that galectin 11 polynucleotides or polypeptides, as well as agonists or antagonists of galectin 11, will also produce changes in hepatocyte proliferation, and epithelial cell proliferation in the lung, breast, pancreas, stomach, small intesting, and large intestine. Galectin 11 polynucleotides or polypeptides, as well as agonists or antagonists of galectin 11, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. Galectin 11 polynucleotides or polypeptides, agonists or antagonists of galectin 11, may promote proliferation of endothelial cells, keratinocytes, and basal keratinocytes.

Galectin 11 polynucleotides or polypeptides, as well as agonists or antagonists of galectin 11, could also be used to reduce the side effects of gut toxicity that result from radiation, chemotherapy treatments or viral infections. Galectin 11 polynucleotides or polypeptides, as well as agonists or antagonists of galectin 11, may have a cytoprotective effect on the small intestine mucosa. Galectin 11 polynucleotides or polypeptides, as well as agonists or antagonists of galectin 11, may also stimulate healing of mucositis (mouth ulcers) that result from chemotherapy and viral infections.

Galectin 11 polynucleotides or polypeptides, as well as agonists or antagonists of galectin 11, could further be used in full regeneration of skin in full and partial thickness skin defects, including burns, (i.e., repopulation of hair follicles, sweat glands, and sebaceous glands), treatment of other skin defects such as psoriasis. Galectin 11 polynucleotides or polypeptides, as well as agonists or antagonists of galectin 11, could be used to treat epidermolysis bullosa, a defect in adherence of the epidermis to the underlying dermis which results in frequent, open and painful blisters by accelerating reepithelialization of these lesions. Galectin 11 polynucleotides or polypeptides, as well as agonists or antagonists of galectin 11, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, galectin 11 polynucleotides or polypeptides, as well as agonists or antagonists of galectin 11, could be used to promote the resurfacing of the mucosal surface to aid more rapid healing and to prevent progression of inflammatory bowel disease. Treatment with galectin 11 polynucleotides or polypeptides, agonists or antagonists of galectin 11, is expected to have a significant effect on the production of mucus throughout the gastrointestinal tract and could be used to protect the intestinal mucosa from injurious substances that are ingested or following surgery. Galectin 11 polynucleotides or polypeptides, as well as agonists or antagonists of galectin 11, could be used to treat diseases associate with the under expression of galectin 11.

Moreover, galectin 11 polynucleotides or polypeptides, as well as agonists or antagonists of galectin 11, could be used to prevent and heal damage to the lungs due to various pathological states. A growth factor such as galectin 11 polynucleotides or polypeptides, as well as agonists or antagonists of galectin 11, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated using galectin 11 polynucleotides or polypeptides, agonists or antagonists of galectin 11. Also, galectin 11 polynucleotides or polypeptides, as well as agonists or antagonists of galectin 11, could be used to stimulate the proliferation of and differentiation of type II pneumocytes, which may help treat or prevent disease such as hyaline membrane diseases, such as infant respiratory distress syndrome and bronchopulmonary displasia, in premature infants.

Galectin 11 polynucleotides or polypeptides, as well as agonists or antagonists of galectin 11, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, galectin 11 polynucleotides or polypeptides, as well as agonists or antagonists of galectin 11, could be used treat or prevent the onset of diabetes mellitus. In patients with newly diagnosed Types I and II diabetes, where some islet cell function remains, galectin 11 polynucleotides or polypeptides, as well as agonists or antagonists of galectin 11, could be used to maintain the islet function so as to alleviate, delay or prevent permanent manifestation of the disease. Also, galectin 11 polynucleotides or polypeptides, as well as agonists or antagonists of galectin 11, could be used as an auxiliary in islet cell transplantation to improve or promote islet cell function.

Galectin 11 polynucleotides or polypeptides, or agonists or antagonists of galectin 11, encoding galectin 11 may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic venoocclusive disease, hypertension, hypotension, ischemia, peripheral vascular diseases, phlebitis, pulmonary venoocclusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboanguitis obliterans, hypersensitivity vasculitis, Schoenlein-Henoch purpura, allergic cutaneous vasculitis, and Wegener's granulomatosis.

Galectin 11 polynucleotides or polypeptides, or agonists or antagonists of galectin 11, are especially effective for the treatment of critical limb ischemia and coronary disease. Galectin 11 polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Galectin 11 polypeptides may be administered as part of a Therapeutic, described in more detail below. Methods of delivering galectin 11 polynucleotides are described in more detail herein.

The naturally occurring balance between endogenous stimulators and inhibitors of angiogenesis is one in which inhibitory influences predominate. Rastinejad et al., *Cell* 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., *Biotech.* 9:630–634 (1991); Folkman et al., *N. Engl. J. Med.,* 333:1757–1763 (1995); Auerbach et al., *J. Microvasc. Res.* 29:401–411 (1985); Folkman, Advances in Cancer Research, eds. Klein and Weinhouse, Academic Press, New York, pp. 175–203 (1985); Patz, *Am. J. Opthalmol.* 94:715–743 (1982); and Folkman et al., *Science* 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, *Science* 235:442–447 (1987).

The present invention provides for treatment of diseases or disorders associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)). Thus, the present invention provides a method of treating an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists of the present invention may be utilized in a variety of additional methods in order to therapeutically treat a cancer or tumor. Cancers which may be treated with polynucleotides, polypeptides, antagonists and/or agonists of the present invention include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists of the present invention may be delivered topically, in order to treat cancers such as skin cancer, head and neck tumors, breast tumors, and Kaposi's sarcoma.

Within yet other aspects, polynucleotides, polypeptides, antagonists and/or agonists of the present invention may be utilized to treat superficial forms of bladder cancer by, for example, intravesical administration. Polynucleotides, polypeptides, antagonists and/or agonists of the present invention may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists of the present invention may be useful in treating other disorders, besides cancers, which involve angiogenesis. These disorders include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention, methods are provided for treating hypertrophic scars and keloids, comprising the step of administering a polynucleotide, polypeptide, antagonist and/or agonist of the invention to a hypertrophic scar or keloid.

Within one embodiment of the polynucleotides, polypeptides, antagonists and/or agonists of the present invention are injected directly into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating neovascular diseases of the eye, including for example, corneal neovascularization, neovascular glaucoma, proliferative diabetic retinopathy, retrolental fibroplasia and macular degeneration.

Moreover, Ocular disorders associated with neovascularization which can be treated with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., *Am. J. Ophthal.* 85:704–710 (1978) and Gartner et al., *Surv. Ophthal.* 22:291–312 (1978).

Thus, within one aspect of the present invention methods are provided for treating neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of disorders can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating neovascular glaucoma, comprising the step of administering to a patient a therapeutically effective amount of a polynucleotide, polypeptide, antagonist and/or agonist of the present invention to the eye, such that the formation of blood vessels is inhibited. In one embodiment, the compound may be administered topically to the eye in order to treat early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating retrolental fibroplasia, comprising the step of administering to a patient a therapeutically effective amount of a polynucleotide, polypeptide, antagonist and/or agonist of the present invention to the eye, such that the formation of blood vessels is inhibited. The compound may be administered topically, via intravitreous injection and/or via intraocular implants.

Additionally, disorders which can be treated with the polynucleotides, polypeptides, agonists and/or agonists of the present invention include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, disorders and/or states, which can be treated with be treated with the the polynucleotides, polypeptides, agonists and/or agonists of the present invention include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (*Helicobacter pylori*), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists of the present invention may also be used in controlling menstruation or administered as either a peritoneal lavage fluid or for peritoneal implantation in the treatment of endometnrosis.

Polynucleotides, polypeptides, agonists and/or agonists of the present invention may be incorporated into surgical sutures in order to prevent stitch granulomas.

Polynucleotides, polypeptides, agonists and/or agonists of the present invention may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist of the present invention to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists of the present invention may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG)

(the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Thus, in one aspect, the present invention is directed to a method for enhancing apoptosis, cell proliferation, cell differentiation, or other cell growth activity regulated by galectin 11, which involves administering to an individual in need of an increased level of galectin 11 functional or biological activity, a therapeutically effective amount of galectin 11 polypeptide, fragment, variant, derivative, or analog, or an agonist capable of increasing galectin 11 mediated cellular responses. In specific embodiments, galectin 11 mediated signaling is increased to treat a disease wherein decreased apoptosis is exhibited.

Given the activities modulated by galectin 11, it is readily apparent that a substantially altered (increased or decreased) level of expression of galectin 11 in an individual compared to the standard or "normal" level produces pathological conditions such as those described above. It will also be appreciated by one of ordinary skill that the galectin 11 polypeptides of the invention will exert its modulating activities on any of its target cells. Therefore, it will be appreciated that conditions caused by a decrease in the standard or normal level of galectin 11 activity in an individual, can be treated by administration of galectin 11 protein or an agonist thereof.

In addition to treating diseases associated with elevated or decreased levels of galectin 11 activity, the invention encompasses methods of administering galectin 11 polypeptides or polynucleotides (including fragments, variants, derivatives and analogs, and agonists and antagonists as described herein) to elevate galectin 11 associated biological activity.

For example, any method which elevates galectin 11 concentration and/or activity can be used to stimulate hematopoiesis. Using these methods, the galectin 11 polypeptide and nucleotide sequences described herein may be used to stimulate hematopoiesis. In a specific embodiment, galectin 11 polypeptides and polynucleotides are used in erythropoietin therapy, which is directed toward supplementing the oxygen carrying capacity of blood. Galectin 11 treatment within the scope of the invention includes, but is not limited, to patients generally requiring blood transfusions, such as, for example, trauma victims, surgical patients, dialysis patients, and patients with a variety of blood composition-affecting disorders, such as hemophilia, cystic fibrosis, pregnancy, menstrual disorders, early anemia of prematurity, spinal cord injury, space flight, aging, various neoplastic disease states, and the like. Examples of patient conditions that require supplementation of the oxygen carrying capacity of blood and which are within the scope of this invention, include but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions.

The invention also encompasses combining the galectin 11 polypeptides and polynucleotides described herein with other proposed or conventional hematopoietic therapies. Thus, for example, galectin 11 can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations with compounds generally used to treat aplastic anemia, such as methenolene, stanozolol, and nandrolone; to treat iron-deficiency anemia, such as iron preparations; to treat malignant anemia, such as vitamin B12 and/or folic acid; and to treat hemolytic anemia, such as adrenocortical steroids, e.g., corticoids. See e.g., Resegotti et al., 1981, Panminerva Medica, 23:243–248; Kurtz, 1982, FEBS Letters, 14a: 105–108; McGonigle et al., 1984, Kidney Int., 25:437–444; and Pavlovic-Kantera, 1980, Expt. Hematol., 8(supp. 8) 283–291.

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Weiland et al., 1982, Blut, 44:173–175; Kalmani, 1982, Kidney Int., 22:383–391; Shahidi, 1973, New Eng. J. Med., 289:72–80; Urabe et al., 1979, J. Exp. Med., 149:1314–1325; Billat et al., 1982, Expt. Hematol., 10:133–140; Naughton et al., 1983, Acta Haemat, 69:171–179; Cognote et al. in abstract 364, Proceedings 7th Intl. Cong. of Endocrinology (Quebec City, Quebec, Jul. 1–7, 1984); and Rothman et al., 1982, J. Surg. Oncol., 20:105–108.

Methods for stimulating hematopoiesis comprise administering a hematopoietically effective amount (i.e, an amount which effects the formation of blood cells) of a pharmaceutical composition containing galectin 11 to a patient. The galectin 11 is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin B12, folic acid and/or adrenocortical steroids. The galectin 11 and cotreatment drug(s) are suitably delivered by separate or by the same administration route, and at the same or at different times, depending, e.g., on dosing, the clinical condition of the patient, etc.

For treating abnormal conditions related to an underexpression of galectin 11 and its activity, or in which elevated or decreased levels of galectin 11 are desired, several approaches are available. One approach comprises administering to an individual in need of an increased level of galectin 11 in the body, a therapeutically effective amount of an isolated galectin 11 polypeptide, fragment, variant, derivative or analog of the invention, or a compound which activates galectin 11, i.e., an agonist as described above, optionally in combination with a pharmaceutically acceptable carrier. Alternatively, gene therapy may be employed to effect the endogenous production of galectin 11 by the relevant cells in the subject. For example, a polynucleotide of the invention may be engineered for expression in a replication defective retroviral vector using techniques known in the art. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For a overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Further, treatment can be administered, for example, in the form of gene replacement therapy. Specifically, one or more copies of a galectin 11 nucleotide sequence of the invention that directs the production of a galectin 11 gene product exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the galectin 11 gene is expressed in neutrophils, such gene replacement techniques should be capable of delivering galectin 11 gene sequence to these cells within patients, or, alternatively, should involve direct administration of such galectin 11 polynucleotide sequences to the site of the cells in which the galectin 11 gene sequences are to be expressed. Alternatively, targeted homologous recombination can be utilized to correct the defective endogenous galectin 11 gene and/or regulatory sequences thereof (e.g., promoter and enhancer sequences), or alternatively, to "turn on" other dormant galectin 11 activity in the appropriate tissue or cell type.

Additional methods which may be utilized to increase the overall level of galectin 11 expression and/or galectin 11 activity include the introduction of appropriate galectin 11-expressing cells, preferably autologous cells, into a patient at positions and in numbers which are sufficient to ameliorate the symptoms of abnormalities in cells growth regulation. Such cells may be either recombinant or non-recombinant. Among the cells which can be administered to increase the overall level of galectin 11 gene expression in a patient are normal cells, which express the galectin 11 gene. Cell-based gene therapy techniques are well known to those skilled in the art, see, e.g., Anderson et al., U.S. Pat. No. 5,399,349; and Mulligan & Wilson, U.S. Pat. No. 5,460,959.

If the activity of galectin 11 is in excess, several approaches are available to reduce or inhibit galectin 11 activity using molecules derived from the polypeptide and polynucleotide sequences described above. Accordingly, a further aspect of the invention is related to a method for treating an individual in need of a decreased level of galectin 11 activity in the body comprising, administering to such an individual a composition comprising a therapeutically effective amount of a galectin 11 polypeptide, fragment, variant, derivative or analog of the invention which acts as a galectin 11 antagonist, optionally, in combination with a pharmaceutically acceptable carrier. Preferably, galectin 11 activity is decreased to treat a disease wherein increased apoptosis or other cell growth activity regulated by galectin 11 is exhibited. Polypeptides, derivatives, variants and analogs of the invention which function as antagonists of galectin 11 can routinely be identified using the assays described infra and other techniques known in the art. Preferred antagonists for use in the present invention are galectin 11-specific antibodies.

Thus, one embodiment of the invention comprises administering to a subject an inhibitor compound (antagonist), such as for example, an antibody or fragment, variant, derivative or analog of the invention, along with a pharmaceutically acceptable carrier in an amount effective to suppress (i.e. lower) galectin 11 activity.

In another approach, galectin 11 activity can be reduced or inhibited by decreasing the level of galectin 11 gene expression. In specific embodiments, antagonists according to the present invention are nucleic acids corresponding to the sequences contained in SEQ ID NO:1, or the complementary strand thereof, and/or to nucleotide sequences contained in the deposited-clone 209053. In one embodiment, this is accomplished through the use of antisense sequences, either internally generated, by the organism, or separately administered (see, for example, O'Connor, J. Neurochem. (1991) 56:560 in Oligodeoxynucleotides as Antisense Inhibitors of Gene Expression, CRC Press, Boca Raton, Fla. (1988). Antisense technology can be used to control gene expression through antisense DNA or RNA or through triple-helix formation. Antisense techniques are discussed, for example, in Okano, J. Neurochem. 56:560 (1991); *Oligodeoxynucleotides as dehydroproline, Antisense Inhibitors of Gene Expression*, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes galectin 11 polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the galectin 11 polypeptide.

The antisense RNA oligonucleotide hybridizes to the mRNA in vivo and blocks translation of the mRNA molecule into polypeptide.

In one embodiment, the galectin 11 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the galectin 11 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding galectin 11, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981)), the regulatory sequences of the metallothionein gene (Brinster et al., Nature 296:39–42 (1982)), etc.

The antisense nucleic acids of the invention comprise a sequence complementary to at least a portion of an RNA transcript of a galectin 11 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded galectin 11 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a galectin 11 RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'- non-translated, non-coding regions of galectin 11 shown in FIG. 1 could be used in an antisense approach to inhibit translation of endogenous galectin 11 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of galectin 11 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the present invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

While antisense nucleotides complementary to the galectin 11 coding region sequence could be used, those complementary to the transcribed untranslated region are most preferred.

Potential galectin 11 antagonists according to the invention also include catalytic RNA, or a ribozyme (See, e.g., PCT International Publication WO 90/11364, published Oct. 4, 1990; Sarver et al., Science 247:1222–1225 (1990). While ribozymes that cleave mRNA at site specific recognition sequences can be used to destroy galectin 11 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). There are numerous potential hammerhead ribozyme cleavage sites within the nucleotide sequence of galectin 11 (FIG. 1; SEQ ID NO:1). Preferably, the ribozyme is engineered so that the cleavage recognition site is located near the 5' end of the galectin 11 mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA.

As in the antisense approach, the ribozymes of the invention can be composed of modified oligonucleotides (e.g. for improved stability, targeting, etc.) and should be delivered to cells which express galectin 11 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous galectin 11 messages and inhibit translation. Since ribozymes, unlike antisense molecules are catalytic, a lower intracellular concentration is required for efficiency.

Endogenous galectin 11 gene expression can also be reduced by inactivating or "knocking out" the galectin 11 gene or its promoter using targeted homologous recombination (e.g., see Smithies et al., Nature 317:330–234 (1985); Thomas et al., Cell 51:503–512 (1987); Thompson et al., Cell 5:313–321 (1989); each of which is incorporated by reference herein in its entirety). Such approach can be adapted for use in humans provided the recombinant DNA constructs are directly administered or targeted to the required site in vivo using appropriate viral vectors.

Alternatively, endogenous galectin 11 gene expression can be reduced by targeted deoxyribonucleotide sequences complementary to the regulatory region of the galectin 11 gene (i.e., the galectin 11 promoter and/or enhancers) to form triple helical structures that prevent transcription of the galectin 11 gene in target cells in the body, see generally, Helene et al., Ann, N.Y. Acad. Sci. 660:27–36 (1992); Helene, C., Anticancer Drug Des., 6(6):569–584 (1991); and Maher, L. J., Bioassays 14(12):807–815 (1992)).

In yet another embodiment of the invention, the activity of galectin 11 can be reduced using a "dominant negative". To this end, constructs which encode defective galectin 11, such as, for example, mutants lacking all or a portion of region of galectin 11 that binds β-galactosides, can be used in gene therapy approaches to diminish the activity of galectin 11 on appropriate target cells. For example, nucleotide sequences that direct host cell expression of galectin 11 in which all or a portion of the region of galectin 11 that binds β-galactoside is altered or missing can be introduced into neutrophil cells, or other cells or tissue which express galectin 11 (either by in vivo or ex vivo gene therapy methods as for example, described herein). Alternatively, targeted homologous recombination can be utilized to introduce such deletions or mutations into the subjects endogenous galectin 11 gene in neutrophils or other cells expressing galectin 11.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Formulation and Administration

It will be appreciated that conditions caused by a decrease in the standard or normal level of galectin 11 activity in an individual, can be treated by administration of galectin 11 polypeptide or fragment, variant, derivative, or analog of the invention or an agonist thereof. Thus, the invention further provides a method of treating an individual in need of an increased level of galectin 11 activity comprising administering to such an individual a pharmaceutical composition comprising an effective amount of an isolated galectin 11 polypeptide or fragment, variant, derivative, or analog of the invention, such as for example, the full length form of the galectin 11, effective to increase the galectin 11 activity level in such an individual.

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

The dosage range required depends on the choice of peptide, the route of administration, the nature of the formulation, the nature of the subject's condition, and the judgment of the attending practitioner. As a general proposition, the total pharmaceutically effective amount of galectin 11 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans this dose is in the range of 0.1–100 mg/kg of subject, or between about 0.01 and 1 mg/kg/day. If given continuously, the galectin 11 polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Pharmaceutical compositions containing the galectin 11 polypeptides and polynucleotides of the invention (including fragments, variants, derivatives or analogs), and galectin 11 agonists and antagonists may be routinely formulated in combination with a pharmaceutically acceptable carrier. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water, saline, buffered saline, glycerol, ethanol, and oils, including those of petroleum, animal, vegetable or synthetic origin, such as peanut oil, soybean oil, mineral oil, sesame oil and the like. Formulation should suit the mode of administration, and is well within the skill of the art. For example, water is a preferred carrier when the pharmaceutical composition is administered intravenously. Saline solutions and aqueous dextrose and glycerol solutions can be employed as liquid carriers, particularly for injectable solutions. The invention additionally relates to pharmaceutical packs and kits comprising one or more containers filled with one or more of the ingredients of the aforementioned compositions of the invention.

Polypeptides and other compounds of the present invention may be administered alone or in conjunction with other compounds, such as therapeutic compounds. The pharmaceutical composition of the invention may be administered orally, rectally, parenterally, intracisternally, intravaginally, intraperitoneally, topically (as by powders, ointments, drops or transdermal patch), bucally, or as an oral or nasal spray. Preferred forms of systemic administration of the pharmaceutical compositions include parenteral injection, typically by intravenous injection. Other injection routes, such as subcutaneous, intramuscular, intrasternal, intraarticular or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl.

J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. Diagnosis and Imaging Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Assaying galectin 11 polypeptide levels in a biological sample can occur using antibody-based techniques. For example, galectin 11 polypeptide expression in tissues can be studied with classical immunohistological methods (Jalkanen, M., et al., *J. Cell. Biol.* 101:976–985 (1985); Jalkanen, M., et al., *J. Cell. Biol.* 105:3087–3096 (1987)). Other antibody-based methods useful for detecting galectin 11 polypeptide gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

A galectin 11 polypeptide-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{112}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, 149Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for cell proliferation disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain galectin 11 protein. In vivo tumor imaging is described in S. W. Burchiel et al., "Immunopharmacokinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Additionally, to detect galectin 11 ligand, any galectin 11 polypeptide whose presence can be detected, can be administered. For example, galectin 11 polypeptides labeled with a radio-opaque or other appropriate compound can be administered and visualized in vivo, as discussed, above for labeled antibodies. Further such galectin 11 polypeptides can be utilized for in vitro diagnostic procedures.

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Chromosome Assays

The nucleic acid molecules of the present invention are also valuable for chromosome identification. The sequence is specifically targeted to and can hybridize with a particular location on human chromosome 11. The mapping of DNAs to chromosomes according to the present invention is an important first step in correlating those sequences with genes associated with disease.

Since the galectin 11 gene has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of Galectin 11 in *E. coli*

The DNA sequence encoding the galectin 11 protein in the deposited cDNA clone is amplified using PCR oligonucleotide primers specific to the amino terminal sequences of the galectin 11 protein and to vector sequences 3' to the gene. Additional nucleotides containing restriction sites to facilitate cloning are added to the 5' and 3' sequences respectively.

The 5' galectin 11 oligonucleotide primer has the sequence 5' cgc CCATGGATGAGCCCCAGGCTGGAGGTG 3' (SEQ ID NO:23) containing the underlined NcoI restriction site and nucleotides 49 to 69 of the galectin 11 nucleotide sequence depicted in FIG. 1 (SEQ ID NO:1).

The 3' galectin 11 primer has the sequence 5' cgc AAGCTTTCAGGAGTGGACACAGTAG 3' (SEQ ID NO:6) containing the underlined HindIII restriction site followed by nucleotides complementary to position 431 to 451 of the galectin 11 nucleotide sequence depicted in FIG. 1 (SEQ ID NO:1).

The restriction sites are convenient to restriction enzyme sites in the bacterial expression vector pQE60 which are used for bacterial expression in these examples. (Qiagen, Inc. 9259 Eton Avenue, Chatsworth, Calif., 91311). pQE60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified galectin 11 DNA and the pQE60 vector is digested with NcoI and HindIII and the digested DNAs are then ligated together. Insertion of the galectin 11 polypeptide DNA into the restricted pQE60 vector places the galectin 11 polypeptide coding region downstream of and operably linked to the vector's IPTG-inducible promoter and in-frame with an initiating AUG appropriately positioned for translation of galectin 11.

The ligation mixture is transformed into competent *E. coli* cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kanr"), is used in carrying out the example described herein. This strain, which is only one of many that are suitable for expressing galectin 11 protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight (O/N) in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside (IPTG) is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized polypeptide is passed over a PD-10 column in 2× phosphate-buffered saline ("PBS"), thereby removing the urea, exchanging the buffer and refolding the protein. The polypeptide is purified by a further step of chromatography to remove endotoxin. Then, it is sterile filtered. The sterile filtered protein preparation was stored in 2× PBS at a concentration of 95 μ/ml.

Example 2

Cloning and Expression of Galectin 11 Protein in a Baculovirus Expression System The cDNA sequence encoding the full length galectin 11 protein in the deposited clone is amplified using PCR oligonucleotide primers corresponding to the 5' and 3' sequences of the gene:

The 5' galectin 11 oligonucleotide primer has the sequence 5' cgc CCCGGG GCCT ATGAGCCCCAG-GCTGGAGG 3' (SEQ ID NO:7) containing the underlined SmaI restriction site and nucleotides 49 to 66 of the galectin 11 nucleotide sequence depicted in FIG. 1 (SEQ ID NO:1).

The 3' Galectin 11 primer has the sequence 5' cgc GGTACC TCAGGAGTGGACACAGTAG 3' (SEQ ID NO:8) containing the underlined Asp718 restriction site followed by nucleotides complementary to position 432 to 450 of the galectin 11 nucleotide sequence depicted in FIG. 1 (SEQ ID NO:1).

An efficient signal for initiation of translation in eukaryotic cells, as described by Kozak, M., J. Mol. Biol. 196: 947–950 (1987) is appropriately located in the vector portion of the construct.

The amplified fragment is isolated from a 1% agarose gel using a commercially available kit ("Geneclean," BIO 101 Inc., La Jolla, Calif.). The fragment then is digested with XbaI and again is purified on a 1% agarose gel. This fragment is designated herein F2.

The vector pA2-GP is used to express the galectin 11 protein in the baculovirus expression system, using standard methods, as described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzyme SmaI and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein V2.

Fragment F2 and the dephosphorylated plasmid V2 are ligated together with T4 DNA ligase. E. coli HB101 cells are transformed with ligation mix and spread on culture plates. Bacteria are identified that contain the plasmid with the human galectin 11 gene by digesting DNA from individual colonies using XbaI and then analyzing the digestion product by gel electrophoresis. The sequence of the cloned fragment is confirmed by DNA sequencing. This plasmid is designated herein pBacgalectin 11.

5 µg of the plasmid pBacgalectin 11 is co-transfected with 1.0 µg of a commercially available linearized baculovirus DNA ("BaculoGold baculovirus DNA", Pharmingen, San Diego, Calif.), using the lipofection method described by Felgner et al., Proc. Natl. Acad. Sci. USA 84: 7413–7417 (1987). 1 µg of BaculoGold virus DNA and 5 µg of the plasmid pBacgalectin 11 are mixed in a sterile well of a microtiter plate containing 50 µl of serum-free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted hESSB I, II and III is identified by DNA analysis including restriction mapping and sequencing. This is designated herein as V-galectin 11.

Sf9 cells are grown in Grace's medium supplemented with 10% heat-inactivated FBS. The cells are infected with the recombinant baculovirus V-galectin 11 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 µCi of 35S-methionine and 5 µCi 35S-cysteine (available from Amersham) are added. The cells are further incubated for 16 hours and then they are harvested by centrifugation, lysed and the labeled proteins are visualized by SDS-PAGE and autoradiography.

Example 3

Cloning and Expression in Mammalian Cells

Most of the vectors used for the transient expression of the galectin 11 polypeptide gene sequence in mammalian cells should carry the SV40 origin of replication. This allows the replication of the vector to high copy numbers in cells (e.g. COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g. RSV, HTLVI, HIVI and the early promoter of the cytomegalovirus (CMV). However, cellular signals can also be used (e.g. human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkat cells, mouse NIH3T3 and C127 cells, Cos 1, Cos 7 and CV1, African green monkey cells, quail QC1–3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277–279 (1991); Bebbington et al., Bio/Technology 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438–4470 (March, 1985)) plus a fragment of the CMV-enhancer (Boshart et al., Cell 41:521–530 (1985)). Multiple cloning sites, e.g. with the restriction enzyme cleavage sites BamHI, XbaI and Asp718, facilitate the cloning of the gene of interest. The vectors contain in addition the 3 intron, the polyadenylation and termination signal of the rat preproinsulin gene.

Example 3(a)

Cloning and Expression in COS Cells

The expression plasmid, pgalectin 11, is made by cloning a cDNA encoding galectin 11 into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the galectin 11 protein and an HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows. The galectin 11 cDNA of the deposited clone is amplified using primers that contain convenient restriction sites, much as described above regarding the construction of expression vectors for expression of galectin 11 in *E. coli*. To facilitate detection, purification and characterization of the expressed galectin 11, one of the primers contains a hemagglutinin tag ("HA tag") as described above.

Suitable primers include the following, which are used in this example. The 5' galectin 11 primer has the sequence 5' cgc CCCGGG gcc atc ATG GCCTATC ATGAGCCCCAG-GCTGGAGG 3' (SEQ ID NO:9) containing the underlined SmaI restriction enzyme site followed by nucleotide sequence 49 to 66 of FIG. 1 (SEQ ID NO:1).

The 3' galectin 11 primer has the sequence 5' cgc GGTACC TCAGGAGTGGACACAGTAG 3' (SEQ ID NO:8) containing the Asp718 restriction followed by nucleotides complementary to nucleotides 432 to 450 of the galectin 11 nucleotide sequence depicted in FIG. 1 (SEQ ID NO:1).

The PCR amplified DNA fragment and the vector, pcD-NAI/Amp, are digested with HindIII and XhoI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the galectin 11-encoding fragment.

For expression of recombinant galectin 11, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989). Cells are incubated under conditions for expression of galectin 11 by the vector.

Expression of the galectin 11 HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC1 is used for the expression of galectin 11 protein. Plasmid pC1 is a derivative of the plasmid pSV2-dhfr [ATCC Accession No. 37146]. Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, PvuII, and NruI. Behind these cloning sites the plasmid contains translational stop codons in all three reading frames followed by the 3 intron and the polyadenylation site of the rat preproinsulin gene. Other high efficient promoters can also be used for the expression, e.g., the human-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphatase by procedures known in the art. The vector is then isolated from a 1% agarose gel.

The DNA sequence encoding galectin 11, ATCC Deposit No. 209053 is amplified using PCR oligonucleotide primers corresponding to the 5' and 3' sequences of the gene:

The 5' Galectin 11 primer has the sequence 5' cgc CCCGGG gcc atc ATG GCCTATC ATGAGCCCCAG-GCTGGAGG 3' (SEQ ID NO:9) containing the underlined SmaI restriction enzyme site followed by nucleotide sequence 49–66 of FIG. 1 (SEQ ID NO:1). Inserted into an expression vector, as described below, the 5' end of the amplified fragment encoding human galectin 11 provides an efficient signal peptide. An efficient signal for initiation of translation in eukaryotic cells, as described by Kozak, M., J. Mol. Biol. 196:947–950 (1987) is appropriately located in the vector portion of the construct.

The 3' Galectin 11 primer has the sequence 5' cgc GGTACC TCAGGAGTGGACACAGTAG 3' (SEQ ID NO:8) containing the Asp718 restriction followed by nucleotides complementary to nucleotides 432–450 of the galectin 11 nucleotide sequence depicted in FIG. 1 (SEQ ID NO:1).

The amplified fragments are isolated from a 1% agarose gel as described above and then digested with the endonucleases SmaI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme SmaI. The sequence of the inserted gene is confirmed by DNA sequencing.

Transfection of CHO-DHFR-Cells

Chinese hamster ovary cells lacking an active DHFR enzyme are used for transfection. 5 μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

Example 4

Tissue Distribution of Protein Expression

Northern blot analysis is carried out to examine galectin 11 gene expression in human tissues, using methods described by, among others, Sambrook et al., cited above. A cDNA probe containing the entire nucleotide sequence encoding galectin 11 protein (SEQ ID NO:1) is labeled with 32P using the rediprime DNA labeling system (Amersham Life Science), according to manufacturer's instructions. After labeling, the probe is purified using a CHROMA SPIN-100 column (Clontech Laboratories, Inc.), according to manufacturer's protocol number PT1200-1. The purified labeled probe is then used to examine various human tissues for galectin 11 mRNA.

Multiple Tissue Northern (MTN) blots containing various human tissues (H) or human immune system tissues (IM) are obtained from Clontech and are examined with labeled probe using ExpressHyb hybridization solution (Clontech) according to manufacturer's protocol number PT1190-1. Following hybridization and washing, the blots are mounted and exposed to film at −70° C. overnight, and films developed according to standard procedures.

It will be clear that the invention may be practiced otherwise than as particularly described in the foregoing description and examples.

Example 5

Galectin 11 Induced Apoptosis in Transfected Cells

This example presents data demonstrating that transfection of a constitutive galectin 11 expression construct into human Jurkat T-cells induces apoptosis of the transfected cells.

A T cell is a type of lymphocyte, or "white blood cell", that mediates the cellular immune response to foreign macromolecule, termed antigens. While T cells are necessary for normal mammalian immune responses, in some instances it is desirable to inhibit their activation: for example, in some autoimmune diseases, the T cells of a subject respond to "self-antigens", i.e., macromolecule produced by the subject, rather than foreign-made macromolecule, and damage the cells and tissues of the subject. Autoimmune T cell responses are found in subjects having systemic lupus erythematosus (SLE), rheumatoid arthritis (RA), insulin-dependent diabetes, myasthenia gravis, and multiple sclerosis (MS) and contribute to the pathophysiology of each. T cells also cause graft rejection and graft versus host disease (GVHD). Graft rejection is caused by an immune response against the transplanted tissues (the graft), which are recognized as "foreign" by T cells of the recipient (host). Graft versus host disease is caused by engrafted T cells, which recognize host-made macromolecule as "foreign."

Methods

The DNA sequence encoding the galectin 11 protein in the deposited cDNA clone was amplified using PCR oligonucleotide primers specific to the amino terminal sequences of the galectin 11 protein and to vector sequences 3' to the gene. The 5' galectin 11 oligonucleotide primer had the sequence 5° CGCCGCCACCATGAGCCCCAGGC 3' (SEQ ID NO:10) containing nucleotides 49 to 61 of the galectin 11 nucleotide sequence in FIG. 1 (SEQ ID NO:1). The 3' galectin 11 primer has the sequence 5' GGAA TCTAGATCAGGAGTGGAC 3' (SEQ ID NO:11) containing the underlined XbaI restriction site followed by nucleotide sequence complementary to position 439 to 450 of the galectin 11 nucleotide sequence in FIG. 1 (SEQ ID) NO:1).

The amplified galectin 11 fragments were isolated from a 1% agarose gel as described above, digested with the endonuclease XbaI, purified again on a 1% agarose gel, and ligated into the multiple cloning site of restricted pEF1 using T4 DNA ligase.

The pEF1 vector was generated by replacing the CMV promoter on pIRES1neo (Clontech) with the human elongation factor 1 a constitutive promoter from pEF-BOS. The EF1a promoter has been shown to be highly active in a variety of cell types (data not shown). This vector also contains a bovine growth hormone poly A signal and a ampicilin resistance gene, a ribosome binding site ("RBS"), a 6-His tag and restriction enzyme sites. This vector was digested with EcoRI, BamHI, and phosphatase using techniques known in the art.

Insertion of the isolated galectin 11 fragment into the restricted pEF1 vector placed the galectin 11 polypeptide coding region downstream of and operably associated with the vector's constitutive elongation factor-1 promoter and in-frame with an initiating AUG appropriately positioned for translation of galectin 11. E. coli cells were then transformed with the ligation reaction and those cells containing the desired construct (pEFLeg11) were identified using techniques known in the art. Cells containing the pEFLeg11 expression construct were then cultured under known conditions favoring high yield and the expression construct was isolated from the bacterial cell culture using techniques known in the art.

For detection of apoptosis, techniques known in the art were used to cotransfect human Jurkat T-cells with the pEFLeg11 expression construct together with a marker plasmid encoding green fluorescent protein (GFP). The transfected cells were then stained with MitoTracker Red (Molecular Probes) to determine the transmembrane potentials of mitochondria, and analyzed by two-color flow cytometry. Transfected populations were identified by emission of green fluorescence due to the expression of GFP. Apoptotic cells exhibit disrupted mitochondrial transmembrane potential and thus have lower red fluorescence emission because of their reduced ability to sequester the dye MitoTracker Red.

Results

Jurkat cells transfected with the constitutive expression plasmid for "galectin 11" underwent significant apoptosis 24h after transfection. Approximately 30% of "galectin 11" transfected cells showed reduced mitochondrial transmembrane potential compared to less than 10% in cells transfected with the control vector with no insert (pEFI) (FIG. 5A).

We also followed the number of GFP positive cells during a 4-day culture period after co-transfection with either the control vector pEF1 or the "galectin 11" expression vector pEF1-Leg11. There were about 4 times more surviving GFP positive cells after transfection with pEF1 than with pEF1-Leg11 (FIG. 5B).

Example 6

Construction of N-Terminal and/or C-Terminal Deletion Mutants

The following general approach may be used to clone a N-terminal or C-terminal deletion galectin 11 deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired galectin 11 polynucleotide fragment. An initiation and stop codon are added to the 5' and 3' primers respectively, if necessary, to express the galectin 11 polypeptide fragment encoded by the polynucleotide fragment. Preferred galectin 11 polynucleotide fragments are those encoding the N-terminal and C-terminal deletion mutants disclosed above in the "Galectin 11 Polypeptide and Fragments" section of the Specification.

Additional nucleotides containing restriction sites to facilitate cloning of the galectin 11 polynucleotide fragment in a desired vector may also be added to the 5' and 3' primer sequences. The galectin 11 polynucleotide fragment is amplified from genomic DNA or from the deposited cDNA clone using the appropriate PCR oligonucleotide primers and conditions discussed herein or known in the art. The galectin 11 polypeptide fragments encoded by the galectin 11 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the galectin 11 polypeptide fragment L-5 to L-128 is amplified and cloned as follows: A 5' primer is generated comprising a restriction enzyme site followed by an initiation codon in frame with the polynucleotide sequence encoding the N-terminal portion of the polypeptide fragment beginning with L-5. A complementary 3' primer is generated comprising a restriction enzyme site followed by a stop codon in frame with the polynucleotide sequence encoding C-terminal portion of the galectin 11 polypeptide fragment ending with L-128.

The amplified polynucleotide fragment and the expression vector are digested with restriction enzymes which recognize the sites in the primers. The digested polynucleotides are then ligated together. The galectin 11 polynucleotide fragment is inserted into the restricted expression vector, preferably in a manner which places the galectin 11 polypeptide fragment coding region downstream from the promoter. The ligation mixture is transformed into competent E. coli cells using standard procedures and as described in the Examples herein. Plasmid DNA is isolated from resistant colonies and the identity of the cloned DNA confirmed by restriction analysis, PCR and DNA sequencing.

Example 7

Protein Fusions of Galectin 11

Galectin 11 polypeptides are preferably fused to other proteins. These fusion proteins can be used for a variety of applications. For example, fusion of galectin 11 polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the halflife time in vivo. Nuclear localization signals fused to galectin 11 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 3.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and galectin 11 polynucleotide, isolated by the PCR protocol described in Example 1, is ligated into this Bamblo site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

GGGATCCGGAGCCCAAATCTTCTGACAAAACTCACACATGCCCACCGTGC

CCAGCACCTGAATTCGAGGGTGCACCGTCAGTCITCCTCAFIACCCCCA

AAACCCAAGGACACCCTCATGATCTCCCGGACTCCTGAGGTCACATGCGT

GGTGGTGGACGTAAGCCACGAAGACCCTGAGGTCAAGTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC

AACCCCCATCGAGAAAACCATCTCCAAAGCCAAAGGGCAGCCCCGAGAAC

CACAGGTGTACACCCTGCCCCCATCCCGGGATGAGCTGACCAAGAACCAG

GTCAGCCTGACCTGCCTGGTCAAAGGCTTCTATCCAAGCGACATCGCCGT

GGAGTGGGAGAGCAATGGGCAGCCGGAGAACAACTACAAGACCACGCCTC

CCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGTGCGACGGCCGCGACTCTAGAGGAT (SEQ ID NO:13)

Example 8

Production of an Antibody a) Hybridoma Technology

The antibodies of the present invention can be prepared by a variety of methods. (See, Current Protocols, Chapter 2.) As one example of such methods, cells expressing galectin 11 are administered to an animal to induce the production of sera containing polyclonal antibodies. In a preferred method, a preparation of galectin 11 protein is prepared and purified to render it substantially free of natural contaminants. Such a preparation is then introduced into an animal in order to produce polyclonal antisera of greater specific activity.

Monoclonal antibodies specific for galectin 11 protein are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with galectin 11 polypeptide or, more preferably, with a secreted galectin 11 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the galectin 11 polypeptide.

Alternatively, additional antibodies capable of binding to galectin 11 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the galectin 11 protein-specific antibody can be blocked by galectin 11. Such antibodies comprise anti-idiotypic antibodies to the galectin 11 protein-specific antibody and are used to immunize an animal to induce formation of further galectin 11 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation Of Antibody Fragments Directed Against Galectin 11 Polypeptides From a Library of scFvs Naturally occurring V-genes isolated from human PBLs are constructed into a library of antibody fragments which contain reactivities against Galectin 11 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log $E.$ $coli$ TG1 by incubating eluted phage with bacteria for 30 minutes at 37° C. The $E.$ $coli$ are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect $E.$ $coli$ HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 9

Production of Galectin 11 Protein for High-Throughput Screening Assays

The following protocol produces a supernatant containing galectin 11 polypeptide to be tested. This supernatant can then be used in the Screening Assays described in Examples 14–21.

First, dilute Poly-D-Lysine (644 587 Boehringer-Mannheim) stock solution (1 mg/ml in PBS) 1:20 in PBS (w/o calcium or magnesium 17-516F Biowhittaker) for a working solution of 50 ug/ml. Add 200 ul of this solution to each well (24 well plates) and incubate at RT for 20 minutes. Be sure to distribute the solution over each well (note: a 12-channel pipetter may be used with tips on every other channel). Aspirate off the Poly-D-Lysine solution and rinse with 1 ml PBS (Phosphate Buffered Saline). The PBS should remain in the well until just prior to plating the cells and plates may be poly-lysine coated in advance for up to two weeks.

Plate 293T cells (do not carry cells past P+20) at $2\times10^5$ cells/well in 0.5 ml DMEM(Dulbecco's Modified Eagle Medium)(with 4.5 G/L glucose and L-glutamine (12-604F Biowhittaker))/10% heat inactivated FBS(14-503F Biowhittaker)/1× Penstrep(17-602E Biowhittaker). Let the cells grow overnight.

The next day, mix together in a sterile solution basin: 300 ul Lipofectamine (18324-012 Gibco/BRL) and 5 ml Optimem I (31985070 Gibco/BRL)/96-well plate. With a small volume multi-channel pipetter, aliquot approximately 2 ug of an expression vector containing a polynucleotide insert, produced by the methods described in Examples 8–10, into an appropriately labeled 96-well round bottom plate. With a multi-channel pipetter, add 50 ul of the Lipofectamine/Optimem I mixture to each well. Pipette up and down gently to mix. Incubate at RT 15–45 minutes. After about 20 minutes, use a multi-channel pipetter to add 150 ul Optimem I to each well. As a control, one plate of vector DNA lacking an insert should be transfected with each set of transfections.

Preferably, the transfection should be performed by tag-teaming the following tasks. By tag-teaming, hands on time is cut in half, and the cells do not spend too much time on PBS. First, person A aspirates off the media from four 24-well plates of cells, and then person B rinses each well with 0.5–1 ml PBS. Person A then aspirates off PBS rinse, and person B, using a 12-channel pipetter with tips on every other channel, adds the 200 ul of DNA/Lipofectamine/Optimem I complex to the odd wells first, then to the even wells, to each row on the 24-well plates. Incubate at 37 degree C. for 6 hours.

While cells are incubating, prepare appropriate media, either 1%BSA in DMEM with 1× penstrep, or HGS CHO-5 media (116.6 mg/L of CaCl2 (anhyd); 0.00130 mg/L CuSO4-5H2O; 0.050 mg/L of Fe(NO3)3-9H2O; 0.417 mg/L of FeSO4-7H2O; 311.80 mg/L of Kcl; 28.64 mg/L of MgCl2; 48.84 mg/L of MgSO4; 6995.50 mg/L of NaCl; 2400.0 mg/L of NaHCO3; 62.50 mg/L of NaH2PO4-H2O; 71.02 mg/L of Na2HPO4; 0.4320 mg/L of ZnSO4-7H2O; 0.002 mg/L of Arachidonic Acid; 1.022 mg/L of Cholesterol; 0.070 mg/L of DL-alpha-Tocopherol-Acetate; 0.0520 mg/L of Linoleic Acid; 0.010 mg/L of Linolenic Acid; 0.010 mg/L of Myristic Acid; 0.010 mg/L of Oleic Acid; 0.010 mg/L of Palmitric Acid; 0.010 mg/L of Palmitic Acid; 100 mg/L of Pluronic F-68; 0.010 mg/L of Stearic Acid; 2.20 mg/L of Tween 80; 4551 mg/L of D-Glucose; 130.85 mg/ml of L-Alanine; 147.50 mg/ml of L-Arginine-HCL; 7.50 mg/ml of L-Asparagine-H2O; 6.65 mg/ml of L-Aspartic Acid; 29.56 mg/ml of L-Cystine-2HCL-H2O; 31.29 mg/ml of L-Cystine-2HCL; 7.35 mg/ml of L-Glutamic Acid; 365.0 mg/ml of L-Glutamine; 18.75 mg/ml of Glycine; 52.48 mg/ml of L-Histidine-HCL-H2O; 106.97 mg/ml of L-Isoleucine; 111.45 mg/ml of L-Leucine; 163.75 mg/ml of L-Lysine HCL; 32.34 mg/ml of L-Methionine; 68.48 mg/ml of L-Phenylalainine; 40.0 mg/ml of L-Proline; 26.25 mg/ml of L-Serine; 101.05 mg/ml of L-Threonine; 19.22 mg/ml of L-Tryptophan; 91.79 mg/ml of L-Tryrosine-2Na-2H2O; and 99.65 mg/ml of L-Valine; 0.0035 mg/L of Biotin; 3.24 mg/L of D-Ca Pantothenate; 11.78 mg/L of Choline Chloride; 4.65 mg/L of Folic Acid; 15.60 mg/L of i-Inositol; 3.02 mg/L of Niacinamide; 3.00 mg/L of Pyridoxal HCL; 0.031 mg/L of Pyridoxine HCL; 0.319 mg/L of Riboflavin; 3.17 mg/L of Thiamine HCL; 0.365 mg/L of Thymidine; 0.680 mg/L of Vitamin B12; 25 mM of HEPES Buffer; 2.39 mg/L of Na Hypoxanthine; 0.105 mg/L of Lipoic Acid; 0.081 mg/L of Sodium Putrescine-2HCL; 55.0 mg/L of Sodium Pyruvate; 0.0067 mg/L of Sodium Selenite; 20 uM of Ethanolamine; 0.122 mg/L of Ferric Citrate; 41.70 mg/L of Methyl-B-Cyclodextrin complexed with Linoleic Acid; 33.33 mg/L of Methyl-B-Cyclodextrin complexed with Oleic Acid; 10 mg/L of Methyl-B-Cyclodextrin complexed with Retinal Acetate. Adjust osmolarity to 327 mOsm) with 2 mm glutamine and 1× penstrep. (BSA (81-068-3 Bayer) 100 gm dissolved in 1L DMEM for a 10% BSA stock solution). Filter the media and collect 50 ul for endotoxin assay in 15 ml polystyrene conical.

The transfection reaction is terminated, preferably by tag-teaming, at the end of the incubation period. Person A aspirates off the transfection media, while person B adds 1.5 ml appropriate media to each well. Incubate at 37 degree C. for 45 or 72 hours depending on the media used: 1% BSA for 45 hours or CHO-5 for 72 hours.

On day four, using a 300 ul multichannel pipetter, aliquot 600 ul in one 1 ml deep well plate and the remaining supernatant into a 2 ml deep well. The supernatants from each well can then be used in the assays described in Examples 11–17.

It is specifically understood that when activity is obtained in any of the assays described below using a supernatant, the activity originates from either the galectin 11 polypeptide directly (e.g., as a secreted protein) or by galectin 11 inducing expression of other proteins, which are then secreted into the supernatant. Thus, the invention further provides a method of identifying the protein in the supernatant characterized by an activity in a particular assay.

Example 10

Construction of GAS Reporter Construct

One signal transduction pathway involved in the differentiation and proliferation of cells is called the Jaks-STATs pathway. Activated proteins in the Jaks-STATs pathway bind to gamma activation site "GAS" elements or interferon-sensitive responsive element ("ISRE"), located in the promoter of many genes. The binding of a protein to these elements alter the expression of the associated gene.

GAS and ISRE elements are recognized by a class of transcription factors called Signal Transducers and Activators of Transcription, or "STATs." There are six members of the STATs family. Stat1 and Stat3 are present in many cell types, as is Stat2 (as response to IFN-alpha is widespread). Stat4 is more restricted and is not in many cell types though it has been found in T helper class I, cells after treatment with IL-12. Stat5 was originally called mammary growth factor, but has been found at higher concentrations in other cells including myeloid cells. It can be activated in tissue culture cells by many cytokines.

The STATs are activated to translocate from the cytoplasm to the nucleus upon tyrosine phosphorylation by a set of kinases known as the Janus Kinase ("Jaks") family. Jaks represent a distinct family of soluble tyrosine kinases and include Tyk2, Jak1, Jak2, and Jak3. These kinases display significant sequence similarity and are generally catalytically inactive in resting cells.

The Jaks are activated by a wide range of receptors summarized in the Table below. (Adapted from review by Schidler and Darnell, Ann. Rev. Biochem. 64:621–51 (1995).) A cytokine receptor family, capable of activating Jaks, is divided into two groups: (a) Class 1 includes receptors for IL-2, IL-3, IL-4, IL-6, IL-7, IL-9, IL-11, EL-12, IL-15, Epo, PRL, GH, G-CSF, GM-CSF, LIF, CNTF, and thrombopoietin; and (b) Class 2 includes IFN-α, IFN-g, and IL-10. The Class 1 receptors share a conserved cysteine motif (a set of four conserved cysteines and one tryptophan) and a WSXWS motif (a membrane proximal region encoding Trp-Ser-Xxx-Trp-Ser (SEQ ID NO:5)).

Thus, on binding of a ligand to a receptor, Jaks are activated, which in turn activate STATs, which then translocate and bind to GAS elements. This entire process is encompassed in the Jaks-STATs signal transduction pathway.

Therefore, activation of the Jaks-STATs pathway, reflected by the binding of the GAS or the ISRE element, can be used to indicate proteins involved in the proliferation and differentiation of cells. For example, growth factors and cytokines are known to activate the Jaks-STATs pathway. (See Table below.) Thus, by using GAS elements linked to reporter molecules, activators of the Jaks-STATs pathway can be identified.

| Ligand | JAKs | | | | STATS | GAS (elements) or ISRE |
| --- | --- | --- | --- | --- | --- | --- |
| | tyk2 | Jak1 | Jak2 | Jak3 | | |
| IFN family | | | | | | |
| IFN-a/B | + | + | − | − | 1,2,3 | ISRE |
| IFN-g | | + | + | − | 1 | GAS (IRF1>Lys6>IFP) |
| Il-10 | + | ? | ? | − | 1,3 | |

-continued

| Ligand | JAKs | | | | STATS | GAS (elements) or ISRE |
|---|---|---|---|---|---|---|
| | tyk2 | Jak1 | Jak2 | Jak3 | | |
| gp130 family | | | | | | |
| IL-6 (Pleiotrohic) | + | + | + | ? | 1,3 | GAS (IRF1>Lys6>IFP) |
| Il-11 (Pleiotrohic) | ? | + | ? | ? | 1,3 | |
| OnM (Pleiotrohic) | ? | + | + | ? | 1,3 | |
| LIF (Pleiotrohic) | ? | + | + | ? | 1,3 | |
| CNTF (Pleiotrohic) | –/+ | + | + | ? | 1,3 | |
| G-CSF (Pleiotrohic) | ? | + | ? | ? | 1,3 | |
| IL-12 (Pleiotrohic) | + | – | + | + | 1,3 | |
| g-C family | | | | | | |
| IL-2 (lymphocytes) | – | + | – | + | 1,3,5 | GAS |
| IL-4 (lymph/myeloid) | – | + | – | + | 6 | GAS (IRF1 = IFP>>Ly6)(IgH) |
| IL-7 (lymphocytes) | – | + | – | + | 5 | GAS |
| IL-9 (lymphocytes) | – | + | – | + | 5 | GAS |
| IL-13 (lymphocyte) | – | + | ? | ? | 6 | GAS |
| IL-15 | ? | + | ? | + | 5 | GAS |
| gp140 family | | | | | | |
| IL-3 (myeloid) | – | – | + | – | 5 | GAS (IRF1>IFP>>Ly6) |
| IL-5 (myeloid) | – | – | + | – | 5 | GAS |
| GM-CSF (myeloid) | – | – | + | – | 5 | GAS |
| Growth hormone family | | | | | | |
| GH | ? | – | + | – | 5 | |
| PRL | ? | +/– | + | – | 1,3,5 | |
| EPO | ? | – | + | – | 5 | GAS(B-CAS>IRF1=IFP>>Ly6) |
| Receptor Tyrosine Kinases | | | | | | |
| EGF | ? | + | + | – | 1,3 | GAS (IRF1) |
| PDGF | ? | + | + | – | 1,3 | |
| CSF-1 | ? | + | + | – | 1,3 | GAS (not IRF1) |

To construct a synthetic GAS containing promoter element, which is used in the Biological Assays described in Examples 11–12, a PCR based strategy is employed to generate a GAS-SV40 promoter sequence. The 5' primer contains four tandem copies of the GAS binding site found in the IRF1 promoter and previously demonstrated to bind STATs upon induction with a range of cytokines (Rothman et al., Immunity 1:457–468 (1994).), although other GAS or ISRE elements can be used instead. The 5' primer also contains 18 bp of sequence complementary to the SV40 early promoter sequence and is flanked with an XhoI site. The sequence of the 5' primer is:
5':GCGCCTCGAGATTTCCCCGAAATCTA-GATTTCCCCGAAATGATTTCCCCGAA ATGATTTC-CCCGAAATATCTGCCATCTCAATTAG:3' (SEQ ID NO:14)

The downstream primer is complementary to the SV40 promoter and is flanked with a Hind III site: 5':GCG-GCAAGCTTTTTGCAAAGCCTAGGC:3' (SEQ ID NO:15)

PCR amplification is performed using the SV40 promoter template present in the B-gal:promoter plasmid obtained from Clontech. The resulting PCR fragment is digested with XhoI/Hind III and subcloned into BLSK2-. (Stratagene.) Sequencing with forward and reverse primers confirms that the insert contains the following sequence:

(SEQ ID NO:16)
5':<u>CTCGAG</u>ATTTCCCCGAAATCTAGATTCCCCGAAATGATTTCCCCGAA

ATGATTCCCCGAAATATCTGCCATCTCAATTAGTCAGCAACCATAGTCC

CGCCCCTAACTCCGCCCATCCCGCCCCTAACTCCGCCCAGTTCCGCCCAT

TCTCCGCCCCATGGCTGACTAATTTTTTTTATTTATGCAGAGGCCGAGGC

CGCCTCGGCCTCTGAGCTATTCCAGAAGTAGTGAGGAGGCTTTTTTGGAG

GCCTAGGCTTTTGCAA<u>AAGCTT</u>:3'

With this GAS promoter element linked to the SV40 promoter, a GAS:SEAP2 reporter construct is next engineered. Here, the reporter molecule is a secreted alkaline phosphatase, or "SEAP." Clearly, however, any reporter molecule can be instead of SEAP, in this or in any of the other Examples. Well known reporter molecules that can be used instead of SEAP include chloramphenicol acetyltransferase (CAT), luciferase, alkaline phosphatase, B-galactosidase, green fluorescent protein (GFP), or any protein detectable by an antibody.

The above sequence confirmed synthetic GAS-SV40 promoter element is subcloned into the pSEAP-Promoter vector obtained from Clontech using HindIII and XhoI, effectively replacing the SV40 promoter with the amplified GAS:SV40 promoter element, to create the GAS-SEAP vector. However, this vector does not contain a neomycin resistance gene, and therefore, is not preferred for mammalian expression systems.

Thus, in order to generate mammalian stable cell lines expressing the GAS-SEAP reporter, the GAS-SEAP cassette is removed from the GAS-SEAP vector using SalI and NotI, and inserted into a backbone vector containing the neomycin resistance gene, such as pGFP-1 (Clontech), using these restriction sites in the multiple cloning site, to create the GAS-SEAP/Neo vector. Once this vector is transfected into mammalian cells, this vector can then be used as a reporter molecule for GAS binding as described in Examples 11–12.

Other constructs can be made using the above description and replacing GAS with a different promoter sequence. For example, construction of reporter molecules containing NFK-B and EGR promoter sequences are described in Examples 14 and 13. However, many other promoters can be substituted using the protocols described in these Examples. For instance, SRE, IL-2, NFAT, or Osteocalcin promoters can be substituted, alone or in combination (e.g., GAS/NF-KB/EGR, GAS/NF-KB, I1-2/NFAT, or NF-KB/GAS). Similarly, other cell lines can be used to test reporter construct activity, such as HELA (epithelial), HUVEC (endothelial), Reh (B-cell), Saos-2 (osteoblast), HUVAC (aortic), or Cardiomyocyte.

Example 11

High-Throughput Screening Assay for T-cell Activity.

The following protocol is used to assess T-cell activity by identifying factors, and determining whether supernate containing a polypeptide of the invention proliferates and/or differentiates T-cells. T-cell activity is assessed using the GAS/SEAP/Neo construct produced in Example 10. Thus, factors that increase SEAP activity indicate the ability to activate the Jaks-STATS signal transduction pathway. The T-cell used in this assay is Jurkat T-cells (ATCC Accession No. TEB-152), although Molt-3 cells (ATCC Accession No. CRL-1552) and Molt-4 cells (ATCC Accession No. CRL-1582) cells can also be used.

Jurkat T-cells are lymphoblastic CD4+Th1 helper cells. In order to generate stable cell lines, approximately 2 million Jurkat cells are transfected with the GAS-SEAP/neo vector using DMRIE-C (Life Technologies)(transfection procedure described below). The transfected cells are seeded to a density of approximately 20,000 cells per well and transfectants resistant to 1 mg/ml genticin selected. Resistant colonies are expanded and then tested for their response to increasing concentrations of interferon gamma. The dose response of a selected clone is demonstrated.

Specifically, the following protocol will yield sufficient cells for 75 wells containing 200 ul of cells. Thus, it is either scaled up, or performed in multiple to generate sufficient cells for multiple 96 well plates. Jurkat cells are maintained in RPMI+10% serum with 1% Pen-Strep. Combine 2.5 mls of OPTI-MEM (Life Technologies) with 10 ug of plasmid DNA in a T25 flask. Add 2.5 ml OPTI-MEM containing 50 ul of DMRIE-C and incubate at room temperature for 15–45 mins.

During the incubation period, count cell concentration, spin down the required number of cells ($10^7$ per transfection), and resuspend in OPTI-MEM to a final concentration of $10^7$ cells/ml. Then add 1 ml of $1 \times 10^7$ cells in OPTI-MEM to T25 flask and incubate at 37 degree C. for 6 hrs. After the incubation, add 10 ml of RPMI+15% serum.P The Jurkat:GAS-SEAP stable reporter lines are maintained in RPMI+10% serum, 1 mg/ml Genticin, and 1% Pen-Strep. These cells are treated with supernatants containing galectin 11 polypeptides or galectin 11 induced polypeptides, as produced by the protocol described in Example 9.

On the day of treatment with the supernatant, the cells should be washed and resuspended in fresh RPMI+10% serum to a density of 500,000 cells per ml. The exact number of cells required will depend on the number of supernatants being screened. For one 96 well plate, approximately 10 million cells (for 10 plates, 100 million cells) are required.

Transfer the cells to a triangular reservoir boat, in order to dispense the cells into a 96 well dish, using a 12 channel pipette. Using a 12 channel pipette, transfer 200 ul of cells into each well (therefore adding 100,000 cells per well).

After all the plates have been seeded, 50 ul of the supernatants are transferred directly from the 96 well plate containing the supernatants into each well using a 12 channel pipette. In addition, a dose of exogenous interferon gamma (0.1, 1.0, 10 ng) is added to wells H9, H10, and H11 to serve as additional positive controls for the assay.

The 96 well dishes containing Jurkat cells treated with supernatants are placed in an incubator for 48 hrs (note: this time is variable between 48–72 hrs). 35 ul samples from each well are then transferred to an opaque 96 well plate using a 12 channel pipette. The opaque plates should be covered (using sellophene covers) and stored at −20 degree C. until SEAP assays are performed according to Example 15. The plates containing the remaining treated cells are placed at 4 degree C. and serve as a source of material for repeating the assay on a specific well if desired.

As a positive control, 100 Unit/ml interferon gamma can be used which is known to activate Jurkat T cells. Over 30 fold induction is typically observed in the positive control wells.

The above protocol may be used in the generation of both transient, as well as, stable transfected cells, which would be apparent to those of skill in the art.

Example 12

High-Throughput Screening Assay Identifying Myeloid Activity

The following protocol is used to assess myeloid activity of galectin 11 by determining whether galectin 11 proliferates and/or differentiates myeloid cells. Myeloid cell activity is assessed using the GAS/SEAP/Neo construct produced in Example 10. Thus, factors that increase SEAP activity indicate the ability to activate the Jaks-STATS signal transduction pathway. The myeloid cell used in this assay is U937, a pre-monocyte cell line, although TF-1, HL60, or KG1 can be used.

To transiently transfect U937 cells with the GAS/SEAP/Neo construct produced in Example 10, a DEAE-Dextran method (Kharbanda et. al., 1994, Cell Growth & Differentiation, 5:259–265) is used. First, harvest $2 \times 10e7$ U937 cells and wash with PBS. The U937 cells are usually grown in RPMI 1640 medium containing 10% heat-inactivated fetal bovine serum (FBS) supplemented with 100 units/ml penicillin and 100 mg/ml streptomycin.

Next, suspend the cells in 1 ml of 20 mM Tris-HCl (pH 7.4) buffer containing 0.5 mg/ml DEAE-Dextran, 8 ug GAS-SEAP2 plasmid DNA, 140 mM NaCl, 5 mM KCl, 375 uM Na2HPO4.7H2O, 1 mM MgCl2, and 675 uM CaCl2. Incubate at 37 degrees C. for 45 min.

Wash the cells with RPMI 1640 medium containing 10% FBS and then resuspend in 10 ml complete medium and incubate at 37 degree C. for 36 hr.

The GAS-SEAP/U937 stable cells are obtained by growing the cells in 400 ug/ml G418. The G418-free medium is used for routine growth but every one to two months, the cells should be re-grown in 400 ug/ml G418 for couple of passages.

These cells are tested by harvesting $1 \times 10^8$ cells (this is enough for ten 96-well plates assay) and wash with PBS.

Suspend the cells in 200 ml above described growth medium, with a final density of $5\times10^5$ cells/ml. Plate 200 ul cells per well in the 96-well plate (or $1\times10^5$ cells/well).

Add 50 ul of the supernatant prepared by the protocol described in Example 9. Incubate at 37 degee C. for 48 to 72 hr. As a positive control, 100 Unit/ml interferon gamma can be used which is known to activate U937 cells. Over 30 fold induction is typically observed in the positive control wells. SEAP assay the supernatant according to the protocol described in Example 15.

Example 13

High-Throughput Screening Assay Identifying Neuronal Activity.

When cells undergo differentiation and proliferation, a group of genes are activated through many different signal transduction pathways. One of these genes, EGR1 (early growth response gene 1), is induced in various tissues and cell types upon activation. The promoter of EGR1 is responsible for such induction. Using the EGR1 promoter linked to reporter molecules, activation of cells can be assessed by galectin 11.

Particularly, the following protocol is used to assess neuronal activity in PC12 cell lines. PC12 cells (rat phenochromocytoma cells) are known to proliferate and/or differentiate by activation with a number of mitogens, such as TPA (tetradecanoyl phorbol acetate), NGF (nerve growth factor), and EGF (epidermal growth factor). The EGR1 gene expression is activated during this treatment. Thus, by stably transfecting PC12 cells with a construct containing an EGR promoter linked to SEAP reporter, activation of PC12 cells by galectin 11 can be assessed.

The EGR/SEAP reporter construct can be assembled by the following protocol. The EGR-1 promoter sequence (−633 to +1)(Sakamoto K et al., Oncogene 6:867–871 (1991)) can be PCR amplified from human genomic DNA using the following primers:

```
                                        (SEQ ID NO:17)
5' GCGCTCGAGGGATGACAGCGATAGAACCCCGG-3'

(SEQ ID NO:18)
5' GCGAAGCTTCGCGACTCCCCGGATCCGCCTC-3'
```

Using the GAS:SEAP/Neo vector produced in Example 10, EGR1 amplified product can then be inserted into this vector. Linearize the GAS:SEAP/Neo vector using restriction enzymes XhoI/HindIII, removing the GAS/SV40 stuffer. Restrict the EGR1 amplified product with these same enzymes. Ligate the vector and the EGR1 promoter.

To prepare 96 well-plates for cell culture, two mls of a coating solution (1:30 dilution of collagen type I (Upstate Biotech Inc. Cat#08-115) in 30% ethanol (filter sterilized)) is added per one 10 cm plate or 50 ml per well of the 96-well plate, and allowed to air dry for 2 hr.

PC12 cells are routinely grown in RPMI-1640 medium (Bio Whittaker) containing 10% horse serum (JRH BIO-SCIENCES, Cat. # 12449-78P), 5% heat-inactivated fetal bovine serum (FBS) supplemented with 100 units/ml penicillin and 100 ug/ml streptomycin on a precoated 10 cm tissue culture dish. One to four split is done every three to four days. Cells are removed from the plates by scraping and resuspended with pipetting up and down for more than 15 times.

Transfect the EGR/SEAP/Neo construct into PC12 using the Lipofectamine protocol described in Example 11. EGR-SEAP/PC12 stable cells are obtained by growing the cells in 300 ug/ml G418. The G418-free medium is used for routine growth but every one to two months, the cells should be re-grown in 300 ug/ml G418 for couple of passages.

To assay for neuronal activity, a 10 cm plate with cells around 70 to 80% confluent is screened by removing the old medium. Wash the cells once with PBS (Phosphate buffered saline). Then starve the cells in low serum medium (RPMI-1640 containing 1% horse serum and 0.5% FBS with antibiotics) overnight.

The next morning, remove the medium and wash the cells with PBS. Scrape off the cells from the plate, suspend the cells well in 2 ml low serum medium. Count the cell number and add more low serum medium to reach final cell density as $5\times105$ cells/ml.

Add 200 ul of the cell suspension to each well of 96-well plate (equivalent to $1\times105$ cells/well). Add 50 ul supernatant produced by Example 9, 37 degree C. for 48 to 72 hr. As a positive control, a growth factor known to activate PC12 cells through EGR can be used, such as 50 ng/ul of Neuronal Growth Factor (NGF). Over fifty-fold induction of SEAP is typically seen in the positive control wells. A SEAP assay of the supernatant is performed according to Example 15.

Example 14

High-Throughput Screening Assay for T-cell Activity

NF-KB (Nuclear Factor KB) is a transcription factor activated by a wide variety of agents including the inflammatory cytokines IL-1 and TNF, CD30 and CD40, lymphotoxin-alpha and lymphotoxin-beta, by exposure to LPS or thrombin, and by expression of certain viral gene products. As a transcription factor, NF-KB regulates the expression of genes involved in immune cell activation, control of apoptosis (NF-KB appears to shield cells from apoptosis), B and T-cell development, anti-viral and antimicrobial responses, and multiple stress responses.

In non-stimulated conditions, NF-KB is retained in the cytoplasm with I-KB (Inhibitor KB). However, upon stimulation, I-KB is phosphorylated and degraded, causing NF-KB to shuttle to the nucleus, thereby activating transcription of target genes. Target genes activated by NF-KB include IL-2, IL-6, GM-CSF, ICAM-1 and class 1 MHC.

Due to its central role and ability to respond to a range of stimuli, reporter constructs utilizing the NF-KB promoter element are used to screen the supernatants produced in Example 9. Activators or inhibitors of NF-KB would be useful in treating diseases. For example, inhibitors of NF-KB could be used to treat those diseases related to the acute or chronic activation of NF-KB, such as rheumatoid arthritis.

To construct a vector containing the NF-KB promoter element, a PCR based strategy is employed. The upstream primer contains four tandem copies of the NF-KB binding site (GGGGACTTTCCC) (SEQ ID NO:19), 18 bp of sequence complementary to the 5' end of the SV40 early promoter sequence, and is flanked with an XhoI site:

```
                                                (SEQ ID NO:20)
5':GCGGCCTCGAGGGGACTTTCCCGGGGACTTTCCGGGGACTTTCCGGG
ACTTTCCATCCTGCCATCTCAATTAG:3'
```

The downstream primer is complementary to the 3' end of the SV40 promoter and is flanked with a Hind III site:

5':GCGGCAAGCTTTTTGCAAAGCCTAGGC:3' (SEQ ID NO:21)

PCR amplification is performed using the SV40 promoter template present in the pB-gal:promoter plasmid obtained from Clontech. The resulting PCR fragment is digested with XhoI and Hind III and subcloned into BLSK2-. (Stratagene) Sequencing with the T7 and T3 primers confirms the insert contains the following sequence:

```
                                              (SEQ ID NO:22)
5':CTCGAGGGGACTTTCCCGGGGACTTTCCGGGGACTTTTCCGGGACTT

TCCATCTGCCATCTCAATTAGTCAGCAACCATAGTCCCGCCCCTAACTCC

GCCCATCCCGCCCCTAACTCCGCCCAGTTCCGCCCATTCTCCGCCCCATG

GCTGACTAATTTTTTTTTATGCAGAGGCCGAGGCCGCCTCGGCCTCTGAG

CTATTCCAGAAGTAGTGAGGAGGCTTTTGGAGGCCTAGGCTTTTGCAAAA

AGC:3'
```

Next, replace the SV40 minimal promoter element present in the pSEAP2-promoter plasmid (Clontech) with this NF-KB/SV40 fragment using XhoI and HindIII. However, this vector does not contain a neomycin resistance gene, and therefore, is not preferred for mammalian expression systems.

In order to generate stable mammalian cell lines, the NF-KB/SV40/SEAP cassette is removed from the above NF-KB/SEAP vector using restriction enzymes SalI and NotI, and inserted into a vector containing neomycin resistance. Particularly, the NF-KB/SV40/SEAP cassette was inserted into pGFP-1 (Clontech), replacing the GFP gene, after restricting pGFP-1 with SalI and NotI.

Once NF-KB/SV40/SEAP/Neo vector is created, stable Jurkat T-cells are created and maintained according to the protocol described in Example 11. Similarly, the method for assaying supernatants with these stable Jurkat T-cells is also described in Example 11. As a positive control, exogenous TNF alpha (0.1, 1, 10 ng) is added to wells H9, H10, and H11, with a 5–10 fold activation typically observed.

Example 15

Assay for SEAP Activity

As a reporter molecule for the assays described in Examples 12 and 13, SEAP activity is assayed using the Tropix Phospho-light Kit (Cat. BP-400) according to the following general procedure. The Tropix Phospho-light Kit supplies the Dilution, Assay, and Reaction Buffers used below.

Prime a dispenser with the 2.5× Dilution Buffer and dispense 15 ul of 2.5× dilution buffer into Optiplates containing 35 ul of a supernatant. Seal the plates with a plastic sealer and incubate at 65 degree C. for 30 min. Separate the Optiplates to avoid uneven heating.

Cool the samples to room temperature for 15 minutes. Empty the dispenser and prime with the Assay Buffer. Add 50 ml Assay Buffer and incubate at room temperature 5 min. Empty the dispenser and prime with the Reaction Buffer (see the table below). Add 50 ul Reaction Buffer and incubate at room temperature for 20 minutes. Since the intensity of the chemiluminescent signal is time dependent, and it takes about 10 minutes to read 5 plates on luminometer, one should treat 5 plates at each time and start the second set 10 minutes later.

Read the relative light unit in the luminometer. Set H12 as blank, and print the results. An increase in chemiluminescence indicates reporter activity.

| Reaction Buffer Formulation: | | |
|---|---|---|
| # of plates | Rxn buffer diluent (ml) | CSPD (ml) |
| 10 | 60 | 3 |
| 11 | 65 | 3.25 |
| 12 | 70 | 3.5 |
| 13 | 75 | 3.75 |
| 14 | 80 | 4 |
| 15 | 85 | 4.25 |
| 16 | 90 | 4.5 |
| 17 | 95 | 4.75 |
| 18 | 100 | 5 |
| 19 | 105 | 5.25 |
| 20 | 110 | 5.5 |
| 21 | 115 | 5.75 |
| 22 | 120 | 6 |
| 23 | 125 | 6.25 |
| 24 | 130 | 6.5 |
| 25 | 135 | 6.75 |
| 26 | 140 | 7 |
| 27 | 145 | 7.25 |
| 28 | 150 | 7.5 |
| 29 | 155 | 7.75 |
| 30 | 160 | 8 |
| 31 | 165 | 8.25 |
| 32 | 170 | 8.5 |
| 33 | 175 | 8.75 |
| 34 | 180 | 9 |
| 35 | 185 | 9.25 |
| 36 | 190 | 9.5 |
| 37 | 195 | 9.75 |
| 38 | 200 | 10 |
| 39 | 205 | 10.25 |
| 40 | 210 | 10.5 |
| 41 | 215 | 10.75 |
| 42 | 220 | 11 |
| 43 | 225 | 11.25 |
| 44 | 230 | 11.5 |
| 45 | 235 | 11.75 |
| 46 | 240 | 12 |
| 47 | 245 | 12.25 |
| 48 | 250 | 12.5 |
| 49 | 255 | 12.75 |
| 50 | 260 | 13 |

Example 16

High-Throughput Screening Assay Identifying Changes in Small Molecule Concentration and Membrane Permeability Binding of a ligand to a receptor is known to alter intracellular levels of small molecules, such as calcium, potassium, sodium, and pH, as well as alter membrane potential. These alterations can be measured in an assay to identify supernatants which bind to receptors of a particular cell. Although the following protocol describes an assay for calcium, this protocol can easily be modified to detect changes in potassium, sodium, pH, membrane potential, or any other small molecule which is detectable by a fluorescent probe.

The following assay uses Fluorometric Imaging Plate Reader ("FLIPR") to measure changes in fluorescent molecules (Molecular Probes) that bind small molecules. Clearly, any fluorescent molecule detecting a small molecule can be used instead of the calcium fluorescent molecule, fluo-4 (Molecular Probes, Inc.; catalog no. F-14202), used here.

For adherent cells, seed the cells at 10,000–20,000 cells/well in a Co-star black 96-well plate with clear bottom. The plate is incubated in a $CO_2$ incubator for 20 hours. The adherent cells are washed two times in Biotek washer with 200 ul of HBSS (Hank's Balanced Salt Solution) leaving 100 ul of buffer after the final wash.

A stock solution of 1 mg/ml fluo-4 is made in 10% pluronic acid DMSO. To load the cells with fluo-4, 50 ul of 12 ug/ml fluo-4 is added to each well. The plate is incubated at 37 degrees C. in a $CO_2$ incubator for 60 min. The plate is washed four times in the Biotek washer with HBSS leaving 100 ul of buffer.

For non-adherent cells, the cells are spun down from culture media. Cells are re-suspended to $2–5 \times 10^6$ cells/ml with HBSS in a 50-ml conical tube. 4 ul of 1 mg/ml fluo-4 solution in 10% pluronic acid DMSO is added to each ml of cell suspension. The tube is then placed in a 37 degrees C. water bath for 30–60 min. The cells are washed twice with HBSS, resuspended to $1 \times 10^6$ cells/ml, and dispensed into a microplate, 100 ul/well. The plate is centrifuged at 1000 rpm for 5 min. The plate is then washed once in Denley CellWash with 200 ul, followed by an aspiration step to 100 ul final volume.

For a non-cell based assay, each well contains a fluorescent molecule, such as fluo-4. The supernatant is added to the well, and a change in fluorescence is detected.

To measure the fluorescence of intracellular calcium, the FLIPR is set for the following parameters: (1) System gain is 300–800 mW; (2) Exposure time is 0.4 second; (3) Camera F/stop is F/2; (4) Excitation is 488 nm; (5) Emission is 530 nm; and (6) Sample addition is 50 ul. Increased emission at 530 nm indicates an extracellular signaling event caused by the a molecule, either galectin 11 or a molecule induced by galectin 11, which has resulted in an increase in the intracellular Ca++ concentration.

Example 17

High-Throughput Screening Assay Identifying Tyrosine Kinase Activity

The Protein Tyrosine Kinases (PTK) represent a diverse group of transmembrane and cytoplasmic kinases. Within the Receptor Protein Tyrosine Kinase RPTK) group are receptors for a range of mitogenic and metabolic growth factors including the PDGF, FGF, EGF, NGF, HGF and Insulin receptor subfamilies. In addition there are a large family of RPTKs for which the corresponding ligand is unknown. Ligands for RPTKs include mainly secreted small proteins, but also membrane-bound and extracellular matrix proteins.

Activation of RPTK by ligands involves ligand-mediated receptor dimerization, resulting in transphosphorylation of the receptor subunits and activation of the cytoplasmic tyrosine kinases. The cytoplasmic tyrosine kinases include receptor associated tyrosine kinases of the src-family (e.g., src, yes, lck, lyn, fyn) and non-receptor linked and cytosolic protein tyrosine kinases, such as the Jak family, members of which mediate signal transduction triggered by the cytokine superfamily of receptors (e.g., the Interleukins, Interferons, GM-CSF, and Leptin).

Because of the wide range of known factors capable of stimulating tyrosine kinase activity, identifying whether galectin 11 or a molecule induced by galectin 11 is capable of activating tyrosine kinase signal transduction pathways is of interest. Therefore, the following protocol is designed to identify such molecules capable of activating the tyrosine kinase signal transduction pathways.

Seed target cells (e.g., primary keratinocytes) at a density of approximately 25,000 cells per well in a 96 well Loprodyne Silent Screen Plates purchased from Nalge Nunc (Naperville, Ill.). The plates are sterilized with two 30 minute rinses with 100% ethanol, rinsed with water and dried overnight. Some plates are coated for 2 hr with 100 ml of cell culture grade type I collagen (50 mg/ml), gelatin (2%) or polylysine (50 mg/ml), all of which can be purchased from Sigma Chemicals (St. Louis, Mo.) or 10% Matrigel purchased from Becton Dickinson (Bedford, Mass.), or calf serum, rinsed with PBS and stored at 4 degree C. Cell growth on these plates is assayed by seeding 5,000 cells/well in growth medium and indirect quantitation of cell number through use of alamarBlue as described by the manufacturer Alamar Biosciences, Inc. (Sacramento, Calif.) after 48 hr. Falcon plate covers #3071 from Becton Dickinson (Bedford, Mass.) are used to cover the Loprodyne Silent Screen Plates. Falcon Microtest III cell culture plates can also be used in some proliferation experiments.

To prepare extracts, A431 cells are seeded onto the nylon membranes of Loprodyne plates (20,000/200 ml/well) and cultured overnight in complete medium. Cells are quiesced by incubation in serum-free basal medium for 24 hr. After 5–20 minutes treatment with EGF (60 ng/ml) or 50 ul of the supernatant produced in Example 12, the medium was removed and 100 ml of extraction buffer ((20 mM HEPES pH 7.5, 0.15 M NaCl, 1% Triton X-100, 0.1% SDS, 2 mM Na3VO4, 2 mM Na4P2O7 and a cocktail of protease inhibitors (# 1836170) obtained from Boeheringer Mannheim (Indianapolis, Ind.) is added to each well and the plate is shaken on a rotating shaker for 5 minutes at 4° C. The plate is then placed in a vacuum transfer manifold and the extract filtered through the 0.45 mm membrane bottoms of each well using house vacuum. Extracts are collected in a 96-well catch/assay plate in the bottom of the vacuum manifold and immediately placed on ice. To obtain extracts clarified by centrifugation, the content of each well, after detergent solubilization for 5 minutes, is removed and centrifuged for 15 minutes at 4 degree C. at 16,000×g.

Test the filtered extracts for levels of tyrosine kinase activity. Although many methods of detecting tyrosine kinase activity are known, one method is described here.

Generally, the tyrosine kinase activity of a supernatant is evaluated by determining its ability to phosphorylate a tyrosine residue on a specific substrate (a biotinylated peptide). Biotinylated peptides that can be used for this purpose include PSK1 (corresponding to amino acids 6–20 of the cell division kinase cdc2-p34) and PSK2 (corresponding to amino acids 1–17 of gastrin). Both peptides are substrates for a range of tyrosine kinases and are available from Boehringer Mannheim.

The tyrosine kinase reaction is set up by adding the following components in order. First, add 10 ul of 5 uM Biotinylated Peptide, then 10 ul ATP/Mg2+ (5 mM ATP/50 mM MgCl2), then 10 ul of 5× Assay Buffer (40 mM imidazole hydrochloride, pH7.3, 40 mM beta-glycerophosphate, 1 mM EGTA, 100 mM MgCl2, 5 mM MnCl2, 0.5 mg/ml BSA), then 5 ul of Sodium Vanadate(1 mM), and then 5 ul of water. Mix the components gently and preincubate the reaction mix at 30 degree C. for 2 min. Initial the reaction by adding 10 ul of the control enzyme or the filtered supernatant.

The tyrosine kinase assay reaction is then terminated by adding 10 ul of 120 mm EDTA and place the reactions on ice.

Tyrosine kinase activity is determined by transferring 50 ul aliquot of reaction mixture to a microtiter plate (MTP) module and incubating at 37 degree C. for 20 min. This allows the streptavadin coated 96 well plate to associate with the biotinylated peptide. Wash the MTP module with 300 ul/well of PBS four times. Next add 75 ul of anti-phospotyrosine antibody conjugated to horse radish peroxidase (anti-P-Tyr-POD(0.5 u/ml)) to each well and incubate at 37 degree C. for one hour. Wash the well as above.

Next add 100 ul of peroxidase substrate solution (Boehringer Mannheim) and incubate at room temperature for at least 5 mins (up to 30 min). Measure the absorbance of the sample at 405 nm by using ELISA reader. The level of bound peroxidase activity is quantitated using an ELISA reader and reflects the level of tyrosine kinase activity.

Example 18

High-Throughput Screening Assay Identifying Phosphorylation Activity

As a potential alternative and/or compliment to the assay of protein tyrosine kinase activity described in Example 16, an assay which detects activation (phosphorylation) of major intracellular signal transduction intermediates can also be used. For example, as described below one particular assay can detect tyrosine phosphorylation of the Erk-1 and Erk-2 kinases. However, phosphorylation of other molecules, such as Raf, JNK, p38 MAP, Map kinase kinase (MEK), MEK kinase, Src, Muscle specific kinase (MuSK), IRAK, Tec, and Janus, as well as any other phosphoserine, phosphotyrosine, or phosphothreonine molecule, can be detected by substituting these molecules for Erk-1 or Erk-2 in the following assay.

Specifically, assay plates are made by coating the wells of a 96-well ELISA plate with 0.1 ml of protein G (1 ug/ml) for 2 hr at room temp, (RT). The plates are then rinsed with PBS and blocked with 3% BSA/PBS for 1 hr at RT. The protein G plates are then treated with 2 commercial monoclonal antibodies (100 ng/well) against Erk-1 and Erk-2 (1 hr at RT) (Santa Cruz Biotechnology). (To detect other molecules, this step can easily be modified by substituting a monoclonal antibody detecting any of the above described molecules.) After 3–5 rinses with PBS, the plates are stored at 4 degree C. until use.

A431 cells are seeded at 20,000/well in a 96-well Loprodyne filterplate and cultured overnight in growth medium. The cells are then starved for 48 hr in basal medium (DMEM) and then treated with EGF (6 ng/well) or 50 ul of the supernatants obtained in Example 9 for 5–20 minutes. The cells are then solubilized and extracts filtered directly into the assay plate.

After incubation with the extract for 1 hr at RT, the wells are again rinsed. As a positive control, a commercial preparation of MAP kinase (10 ng/well) is used in place of A431 extract. Plates are then treated with a commercial polyclonal (rabbit) antibody (1 ug/ml) which specifically recognizes the phosphorylated epitope of the Erk-1 and Erk-2 kinases (1 hr at RT). This antibody is biotinylated by standard procedures. The bound polyclonal antibody is then quantitated by successive incubations with Europium-streptavidin and Europium fluorescence enhancing reagent in the Wallac DELFIA instrument (time-resolved fluorescence). An increased fluorescent signal over background indicates a phosphorylation by galectin 11 or a molecule induced by galectin 11.

Example 19

Method of Determining Alterations in the Galectin 11 Gene

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degree C. for 30 seconds; 60–120 seconds at 52–58 degree C; and 60–120 seconds at 70 degree C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of galectin 11 is also determined and genomic PCR products analyzed to confirm the results. PCR products harboring suspected mutations in galectin 11 is then cloned and sequenced to validate the results of the direct sequencing.

PCR products of galectin 11 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in galectin 11 not present in unaffected individuals.

Genomic rearrangements are also observed as a method of determining alterations in a gene corresponding to galectin 11. The full length galectin 11 cDNA amplified according to Example 1 is nick-translated with digoxigenindeoxy-uridine 5'-triphosphate (Boehringer Manheim), and FISH performed as described in Johnson, Cg. et al., Methods Cell Biol. 35:73–99 (1991). Hybridization with the labeled probe is carried out using a vast excess of human cot-1 DNA for specific hybridization to the galectin 11 genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of galectin 11 (hybridized by the probe) are identified as insertions, deletions, and translocations. These galectin 11 alterations are used as a diagnostic marker for an associated disease.

Example 20

Method of Detecting Abnormal Levels of Galectin 11 in a Biological Sample

Galectin 11 polypeptides can be detected in a biological sample, and if an increased or decreased level of galectin 11 is detected, this polypeptide is a marker for a particular phenotype. Methods of detection are numerous, and thus, it is understood that one skilled in the art can modify the following assay to fit their particular needs.

For example, antibody-sandwich ELISAs are used to detect galectin 11 in a sample, preferably a biological sample. Wells of a microtiter plate are coated with specific antibodies to galectin 11, at a final concentration of 0.2 to 10 ug/ml. The antibodies are either monoclonal or polyclonal and are produced by the method described in Example 8. The wells are blocked so that non-specific binding of galectin 11 to the well is reduced.

The coated wells are then incubated for >2 hours at RT with a sample containing galectin 11. Preferably, serial dilutions of the sample should be used to validate results. The plates are then washed three times with deionized or distilled water to remove unbounded galectin 11.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot galectin 11 polypeptide concentration on the X-axis (log scale) and fluorescence or absorbance of the Y-axis (linear scale). Interpolate the concentration of the galectin 11 in the sample using the standard curve.

Example 21

Formulation

The invention also provides methods of treatment and/or prevention of diseases or disorders (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see generally, Langer, Science 249:1527–1533 (1990); Treat et al., in Liposomes in the Therapy of Infectious Disease and Cancer, Lopez-Berestein and Fidler (eds.), Liss, N.Y., pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chermical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multidose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal antiinflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD 154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP- 282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FELGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 22

Method of Treating Decreased Levels of Galectin 11

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of galectin 11 in an individual can be treated by administering a galectin 11 of the present invention, preferably in the secreted form. Thus, the invention also provides a method of treatment of an individual in need of an increased level of a galectin 11 polypeptide of the present invention comprising administering to such an individual a Therapeutic comprising an amount of that galectin 11 to increase the activity level of galectin 11 in such an individual.

For example, a patient with decreased levels of galectin 11 polypeptide receives a daily dose 0.1–100 ug/kg of the polypeptide for six consecutive days. Preferably, the polypeptide is in the secreted form. The exact details of the dosing scheme, based on administration and formulation, are provided in Example 20.

Example 23

Method of Treating Increased Levels of Galectin 11

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of galectin 11. This technology is one example of a method of decreasing levels of galectin 11 polypeptide, preferably a secreted form, due to a variety of etiologies, such as cancer.

For example, a patient diagnosed with abnormally increased levels of galectin 11 is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in Example 20.

Example 24

Method of Treatment Using Gene Therapy—Ex Vivo

One method of gene therapy transplants fibroblasts, which are capable of expressing galectin 11 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

A cDNA of the present invention encoding galectin 11 can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted galectin 11.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the galectin 11 gene is then added to the media and the packaging cells transduced with the vector. The packaging cells now produce infectious viral particles containing the galectin 11 gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether galectin 11 protein is produced.

The engineered fibroblasts are then transplanted onto the host, either alone or after having been grown to confluence on cytodex 3 microcarrier beads.

Example 25

Gene Therapy Using Endogenous Galectin 11 Gene

Another method of gene therapy according to the present invention involves operably associating the endogenous galectin 11 sequence with a promoter via homologous recombination as described, for example, in U.S. Patent No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous galectin 11, flanking the promoter. The targeting sequence will be sufficiently near the 5' end of galectin 11 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous galectin 11 sequence. This results in the expression of galectin 11 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the galectin 11 locus, plasmid pUC18 (MBI Fermentas, Amherst, N.Y.) is digested with HindIII. The CMV promoter is amplified by PCR with an XbaI site on the 5' end and a BamHI site on the 3'end. Two galectin 11 non-coding sequences are amplified via PCR: one galectin 11 non-coding sequence (galectin 11 fragment 1) is amplified with a HindIII site at the 5' end and an Xba site at the 3'end; the other galectin 11 non-coding sequence (Galectin 11 fragment 2) is amplified with a BamHI site at the 5'end and a HindIII site at the 3'end. The CMV promoter and galectin 11 fragments (1 and 2) are digested with the appropriate enzymes (CMV promoter—XbaI and BamHI; galectin 11 fragment 1—XbaI; galectin 11 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 26

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) galectin 11 sequences into an animal to increase or decrease the expression of the galectin 11 polypeptide. The galectin 11 polynucleotide may be operatively linked to a promoter or any other genetic elements necessary for the expression of the galectin 11 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al. (1997) Cardiovasc. Res. 35(3):470–479, Chao J et al. (1997) Pharmacol. Res. 35(6):517–522, Wolff J. A. (1997) Neuromuscul. Disord. 7(5):314–318, Schwartz B. et al. (1996) Gene Ther. 3(5):405–411, Tsurumi Y. et al. (1996) Circulation 94(12):3281–3290 (incorporated herein by reference).

The galectin 11 polynucleotide constructs may be delivered by any method that delivers injectable materials to the cells of an animal, such as, injection into the interstitial space of tissues (heart, muscle, skin, lung, liver, intestine and the like). The galectin 11 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the galectin 11 polynucleotides may also be delivered in liposome formulations (such as those taught in Feigner P. L. et al. (1995) Ann. NY Acad. Sci. 772:126–139 and Abdallah B. et al. (1995) Biol. Cell 85(1):1–7) which can be prepared by methods well known to those skilled in the art.

The galectin 11 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The galectin 11 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked galectin 11 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked galectin 11 polynucleotide constructs can be delivered to arteries during angioplasty by the catheter used in the procedure.

The dose response effects of injected galectin 11 polynucleotide in muscle in vivo is determined as follows. Suitable galectin 11 template DNA for production of mRNA coding for galectin 11 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The galectin 11 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for galectin 11 protein expression. A time course for galectin 11 protein expression may be done in a similar fashion except that quadriceps from different mice are harvested at different times. Persistence of galectin 11 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using galectin 11 naked DNA.

Example 27

Galectin 11 Transgenic Animals

The galectin 11 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Any of the galectin 11 polypeptides disclosed throughout this application can be used to generate transgenic animals. For example, the DNA encoding galectin 11 protein can be inserted into a vector using a primer, such as: A 5' primer containing the underlined SmaI restriction site shown: 5' cgc CCCGGG GCCT ATGAGCCCCAGGCTGGAGG 3' (SEQ ID NO:7) and a 3' primer sequence 5' cgc GGTACC TCAG-GAGTGGACACAGTAG 3' (SEQ ID NO:8) containing the underlined Asp718 restriction site followed by nucleotides complementary to position 432 to 450 of the galectin 11 nucleotide sequence depicted in FIG. 1 (SEQ ID NO:1).

Besides these two examples, other fragments of galectin 11 can also be inserted into a vector to create transgenics having ubiquitous expression.

Alternatively, polynucleotides of the invention can be inserted in a vector which controls tissue specific expression through a tissue specific promoter. For example, a construct having a transferrin promoter would express the galectin 11 polypeptide in the liver of transgenic animals. Therefore, DNA encoding the full length galectin 11 protein can also be inserted into a vector for tissue specific expression using the following primers: A 5' primer containing the underlined SmaI restriction site shown: 5' cgc CCCGGG GCCT ATGAGCCCCAGGCTGGAGG 3' (SEQ ID NO:7) and a 3' primer, containing the underlined Asp 178 restriction site shown: 5' cgc GGTACC TCAGGAGTGGACACAGTAG 3' (SEQ ID NO:8)

In addition to expressing the polypeptide of the present invention in a ubiquitous or tissue specific manner in transgenic animals, it would also be routine for one skilled in the art to generate constructs which regulate expression of the polypeptide by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of galectin 11 polypeptides, studying conditions and/or disorders associated with aberrant galectin 11 expression, and in screening for compounds effective in ameliorating such conditions and/or disorders.

Example 28

Galectin 11 Knock-Out Animals

Endogenous galectin 11 gene expression can also be reduced by inactivating or "knocking out" the galectin 11 gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the galectin 11 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Knock-out animals of the invention have uses which include, but are not limited to, animal model systems useful in elaborating the biological function of galectin 11 polypeptides, studying conditions and/or disorders associated with aberrant galectin 11 expression, and in screening for compounds effective in ameliorating such conditions and/or disorders.

Example 29

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay—Purified galectin 11 protein, or truncated forms thereof, is assessed for its ability to induce activation, proliferation, differentiation or inhibition and/or death in B-cell populations and their precursors. The activity of galectin 11 protein on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed *Staphylococcus aureus* Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R (B220).

Various dilutions of each sample are placed into individual wells of a 96-well plate to which are added $10^5$ B-cells suspended in culture medium (RPMI 1640 containing 10% FBS, $5\times10^{-5}$M 2ME, 100 U/ml penicillin, 10 ug/ml streptomycin, and $10^{-5}$ dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of Galectin 11 protein, or truncated forms thereof. Mice receive this treatment for 4 consecutive days, at which time they are sacrificed and various tissues and serum collected for analyses. Comparison of H&E sections from normal and galectin 11 protein-treated spleens identify the results of the activity of galectin 11 protein on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from galectin 11 protein-treated mice is used to indicate whether galectin 11 protein specifically increases the proportion of ThB+, CD45R(B220)dull B cells over that which is observed in control mice.

Likewise, a predicted consequence of increased mature B-cell representation in vivo is a relative increase in serum Ig titers. Accordingly, serum IgM and IgA levels are compared between buffer and galectin 11 protein-treated mice.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 30

T Cell Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells ($5\times10^4$/well) of mAb coated plates in RPMI containing 10% FCS and P/S in the presence of varying concentrations of Galectin 11 protein (total volume 200 μl). Relevant protein buffer and medium alone are controls. After 48 hr. culture at 37° C., plates are spun for 2 min. at 1000 rpm and 100 μl of supernatant is removed and stored –20° C. for measurement of IL-2 (or other cytokines) if effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of galectin 11 proteins.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 31

Effect of Galectin 11 on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1–3 days with increasing concentrations of galectin 11 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of galectin 11 for 24 hours. LPS (100 ng/ml) is added to the cell culture as positive control. Supernatants from the cell cultures are then collected and analyzed for IL-12 content using commercial ELISA kit (e.g, R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of galectin 11 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. galectin 11, agonists, or antagonists of galectin 11 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 μg/ml, and then incubaed at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of galectin 11 and under the same conditions, but in the absence of galectin 11. For IL-12 production, the cells are primed overnight with IFN (100 U/ml) in presence of galectin 11. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g, R & D Systems (Minneapolis, Minn.)) and applying the standard protocols provided with the kit.

Oxidative burst. Purified monocytes are plated in 96-w plate at $2–1\times10^5$ cell/well. Increasing concentrations of galectin 11 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 32

Galectin 11 Biological Effects

Astrocyte and Neuronal Assays.

Recombinant galectin 11, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate galectin 11's activity on these cells.

Moreover, previous reports describing the biological effects of FGF-2 (basic FGF) on cortical or hippocampal neurons in vitro have demonstrated increases in both neuron survival and neurite outgrowth (Walicke, P. et al., "Fibroblast growth factor promotes survival of dissociated hippocampal neurons and enhances neurite extension." *Proc. Natl. Acad. Sci. USA* 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of galectin 11 to induce neurite outgrowth can be compared to the response achieved with FGF-2 using, for example, a thymidine incorporation assay.

Fibroblast and Endothelial Cell Assays.

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or galectin 11 with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or galectin 11 with or without IL-1α for 24 hours. The supernatants are collected and assayed for IL-6 by ELISA kit (Endogen, Cambridge, Mass.).

Human lung fibroblasts are cultured with FGF-2 or galectin 11 for 3 days in basal medium before the addition of Alamar Blue to assess effects on growth of the fibroblasts. FGF-2 should show a stimulation at 10–2500 ng/ml which can be used to compare stimulation with galectin 11.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, galectin 11 can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of galectin 11 is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/$cm^2$ on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if galectin 11 acts to prolong the survival of dopaminergic neurons, it would suggest that galectin 11 may be involved in Parkinson's Disease.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 33

The Effect of Galectin 11 on the Growth of Vascular Endothelial Cells

On day 1, human umbilical vein endothelial cells (HUVEC) are seeded at $2–5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. Galectin 11 protein of SEQ ID NO. 2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that galectin 11 may proliferate vascular endothelial cells.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 34

Stimulatory Effect of Galectin 11 on the Proliferation of Vascular Endothelial Cells For evaluation of mitogenic activity of growth factors, the colorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, $VEGF_{165}$ or Galectin 11 in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. *In Vitro Cell. Dev. Biol.* 30A:512–518 (1994).

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 35

Inhibition of PDGF-Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4° C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., *J. Biol. Chem.* 6:271(36): 21985–21992 (1996).

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 36

Stimulation of Endothelial Migration

This example will be used to explore the possibility that galectin 11 may stimulate lymphatic endothelial cell migration.

Endothelial cell migration assays are performed using a 48 well microchemotaxis chamber (Neuroprobe Inc., Cabin John, M D; Falk, W., et al., *J. Immunological Methods* 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, $2.5 \times 10^5$ cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 37

Stimulation of Nitric Oxide Production by Endothelial Cells

Nitric oxide released by the vascular endothelium is believed to be a mediator of vascular endothelium relaxation. Thus, galectin 11 activity can be assayed by determining nitric oxide production by endothelial cells in response to galectin 11.

Nitric oxide is measured in 96-well plates of confluent microvascular endothelial cells after 24 hours starvation and a subsequent 4 hr exposure to various levels of a positive control (such as VEGF-1) and galectin 11. Nitric oxide in the medium is determined by use of the Griess reagent to measure total nitrite after reduction of nitric oxide-derived nitrate by nitrate reductase. The effect of galectin 11 on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

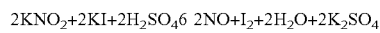
$$2KNO_2 + 2KI + 2H_2SO_4 \rightarrow 2NO + I_2 + 2H_2O + 2K_2SO_4$$

The standard calibration curve is obtained by adding graded concentrations of $KNO_2$ (0, 5, 10, 25, 50, 100, 250, and 500 nmol/L) into the calibration solution containing KI and $H_2SO_4$. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per $1 \times 10^6$ endothelial cells. All values reported are means of four to six measurements in each group (number of cell culture wells). See, Leak et al. *Biochem. and Biophys. Res. Comm.* 217: 96–105 (1995).

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 38

Effect of Galectin 11 on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or galectin 11 (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 39

Angiogenic Effect on Chick Chorioallantoic Membrane

Chick chorioallantoic membrane (CAM) is a well-established system to examine angiogenesis. Blood vessel formation on CAM is easily visible and quantifiable. The ability of Galectin 11 to stimulate angiogenesis in CAM can be examined.

Fertilized eggs of the White Leghorn chick (Gallus gallus) and the Japanese qual (Coturnix coturnix) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nune, Naperville, Ill.) are cut into disks of about 5 mm in diameter. Sterile and salt-free growth factors are dissolved in distilled water and about 3.3 mg/5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 40

Angiogenesis Assay Using a Matrigel Implant in Mouse

In vivo angiogenesis assay of galectin 11 measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with galectin 11 at 150 ng/ml at 4 degree C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 41

Rescue of Ischemia in Rabbit Lower Limb Model

To study the in vivo effects of galectin 11 on ischemia, a rabbit hindlimb ischemia model is created by surgical removal of one femoral arteries as described previously (Takeshita, S. et al., Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshita, S. et al. Am J. Pathol 147: 1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked galectin 11 expression plasmid by arterial gene transfer technology using a hydrogel-coated balloon catheter as described (Riessen, R. et al. Hum Gene Ther. 4:749–758 (1993); Leclerc, G. et al. J. Clin. Invest. 90: 936–944 (1992)). When galectin II is used in the treatment, a single bolus of 500 mg galectin 11 protein or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score—This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 42

Effect of Galectin 11 on Vasodilation

Since dilation of vascular endothelium is important in reducing blood pressure, the ability of galectin 11 to affect the blood pressure in spontaneously hypertensive rats (SHR) is examined. Increasing doses (0, 10, 30, 100, 300, and 900 mg/kg) of the galectin 11 are administered to 13–14 week old spontaneously hypertensive rats (SHR). Data are expressed as the mean +/−SEM. Statistical analysis is performed with a paired t-test and statistical significance is defined as $p<0.05$ vs. the response to buffer alone.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 43

Rat Ischemic Skin Flap Model

The evaluation parameters include skin blood flow, skin temperature, and factor VIII immunohistochemistry or endothelial alkaline phosphatase reaction. Galectin 11 expression, during the skin ischemia, is studied using in situ hybridization.

The study in this model is divided into three parts as follows:
a) Ischemic skin
b) Ischemic skin wounds
c) Normal wounds The experimental protocol includes:
a) Raising a 3×4 cm, single pedicle full-thickness random skin flap (myocutaneous flap over the lower back of the animal).
b) An excisional wounding (4–6 mm in diameter) in the ischemic skin (skin-flap).
c) Topical treatment with galectin 11 of the excisional wounds (day 0, 1, 2, 3, 4 post-wounding) at the following various dosage ranges: 1 mg to 100 mg.
d) Harvesting the wound tissues at day 3, 5, 7, 10, 14 and 21 post-wounding for histological, immunohistochemical, and in situ studies.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 44

Peripheral Arterial Disease Model

Angiogenic therapy using galectin 11 is a novel therapeutic strategy to obtain restoration of blood flow around the ischemia in case of peripheral arterial diseases. The experimental protocol includes:
a) One side of the femoral artery is ligated to create ischemic muscle of the hindlimb, the other side of hindlimb serves as a control.
b) Galectin 11 protein, in a dosage range of 20 mg–500 mg, is delivered intravenously and/or intramuscularly 3 times (perhaps more) per week for 2–3 weeks.
c) The ischemic muscle tissue is collected after ligation of the femoral artery at 1, 2, and 3 weeks for the analysis of galectin 11 expression and histology. Biopsy is also performed on the other side of normal muscle of the contralateral hindlimb.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 45

Ischemic Myocardial Disease Model

Galectin 11 is evaluated as a potent mitogen capable of stimulating the development of collateral vessels, and restructuring new vessels after coronary artery occlusion. Alteration of galectin 11 expression is investigated in situ. The experimental protocol includes:

a) The heart is exposed through a left-side thoracotomy in the rat. Immediately, the left coronary artery is occluded with a thin suture (6-0) and the thorax is closed.

b) Galectin 11 protein, in a dosage range of 20 mg–500 mg, is delivered intravenously and/or intramuscularly 3 times (perhaps more) per week for 2–4 weeks.

c) Thirty days after the surgery, the heart is removed and cross-sectioned for morphometric and in situ analyzes.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 46

Rat Corneal Wound Healing Model

This animal model shows the effect of galectin 11 on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of galectin 11, within the pocket.

e) Galectin 11 treatment can also be applied topically to the corneal wounds in a dosage range of 20 mg–500 mg (daily treatment for five days).

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 47

Diabetic Mouse and Glucocorticoid-Impaired Wound Healing Models

A. Diabetic db+/db+ Mouse Model.

To demonstrate that galectin 11 accelerates the healing process, the genetically diabetic mouse model of wound healing is used. The full thickness wound healing model in the db+/db+ mouse is a well characterized, clinically relevant and reproducible model of impaired wound healing. Healing of the diabetic wound is dependent on formation of granulation tissue and re-epithelialization rather than contraction (Gartner, M. H. et al., *J. Surg. Res.* 52:389 (1992); Greenhalgh, D. G. et al., *Am. J. Pathol.* 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. *Proc. Natl. Acad. Sci. USA* 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., *J. Immunol.* 120:1375 (1978); Debray-Sachs, M. et al., *Clin. Exp. Immunol.* 51(1):1–7 (1983); Leiter et al., *Am. J. of Pathol.* 114:46–55 (1985)). Peripheral neuropathy, myocardial complications, and microvascular lesions, basement membrane thickening and glomerular filtration abnormalities have been described in these animals (Norido, F. et al., *Exp. Neurol.* 83(2):221–232 (1984); Robertson et al., *Diabetes* 29(1):60–67 (1980); Giacomelli et *Lab Invest.* 40(4): 460–473 (1979); Coleman, D. L., *Diabetes* 31 (*Suppl*):1–6 (1982)). These homozygous diabetic mice develop hyperglycemia that is resistant to insulin analogous to human type II diabetes (Mandel et al., *J. Immunol.* 120:1375–1377 (1978)).

The characteristics observed in these animals suggests that healing in this model may be similar to the healing observed in human diabetes (Greenhalgh, et al., *Am. J. of Pathol.* 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Human Genome Sciences, Inc. Institutional Animal Care and Use Committee and the Guidelines for the Care and Use of Laboratory Animals.

Wounding protocol is performed according to previously reported methods (Tsuboi, R. and Rifkin, D. B., *J. Exp. Med.* 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

Galectin 11 is administered using at a range different doses of galectin 11, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated; and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm², the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with galectin 11. This assessment included verification of the presence of cell accumulation, inflammatory cells, capillaries, fibroblasts, re-epithelialization and epidermal maturity (Greenhaigh, D. G. et al., *Am. J. Pathol.* 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, S. M. Glucocorticoids and Wound healing. In: Anti-Inflammatory Steroid Action: Basic and Clinical Aspects. 280–302 (1989); Wahl, S. M. et al., *J. Immunol.* 115: 476–481 (1975); Werb, Z. et al., *J. Exp. Med.* 147:1684–1694 (1978)). Glucocorticoids retard wound healing by inhibiting angiogenesis, decreasing vascular permeability (Ebert, R. H., et al., *An. Intern. Med.* 37:701–705 (1952)), fibroblast proliferation, and collagen synthesis (Beck, L. S. et al., *Growth Factors.* 5: 295–304 (1991); Haynes, B. F. et al., *J. Clin. Invest.* 61: 703–797 (1978)) and producing a transient reduction of circulating monocytes (Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck, L. S. et al., *Growth Factors.* 5: 295–304 (1991); Haynes, B. F., et al., *J. Clin. Invest.* 61: 703–797 (1978); Wahl, S. M., "Glucocorticoids and wound healing", In: Antiinflammatory Steroid Action: Basic and Clinical Aspects, Academic Press, New York, pp. 280–302 (1989); Pierce, G. F. et al., *Proc. Natl. Acad. Sci. USA* 86: 2229–2233 (1989)).

To demonstrate that galectin 11 can accelerate the healing process, the effects of multiple topical applications of galectin 11 on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study is conducted according to the rules and guidelines of Human Genome Sciences, Inc. Institutional Animal Care and Use Committee and the Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

Galectin 11 is administered using at a range different doses of galectin 11, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) galectin 11 treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm², the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with galectin 11. A calibrated lens micrometer is used by a blinded observer to determine the distance of the wound gap.

Experimental data are analyzed using an unpaired t test. A p value of <0.05 is considered significant.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 48

Lymphadema Animal Model

The purpose of this experimental approach is to create an appropriate and consistent lymphedema model for testing the therapeutic effects of Galectin 11 in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated or suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle is observed under fluorescent microscopy for lymphatics.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 49

Suppression of TNF Alpha-Induced Adhesion Molecule Expression by Galectin 11

The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of galectin 11 to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM- 2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 μl of 0.1% paraformaldehyde-PBS (with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 μl of diluted primary antibody to the test and control wells. Anti-ICAM-1-Biotin, Anti-VCAM-1-Biotin and Anti-E-selectin-Biotin are used at a concentration of 10 μg/ml (1:10 dilution of 0.1 mg/ml stock antibody). Cells are incubated at 37° C. for 30 min. in a humidified environment. Wells are washed X3 with PBS (+Ca,Mg)+0.5% BSA.

Then add 20 μl of diluted ExtrAvidin-Alkaline Phosphotase (1:5,000 dilution) to each well and incubated at 37° C. for 30 min. Wells are washed X3 with PBS(+Ca,Mg)+0.5% BSA. 1 tablet of p-Nitrophenol Phosphate pNPP is dissolved in 5 ml of glycine buffer (pH 10.4). 100 μl of pNPP substrate in glycine buffer is added to each test well. Standard wells in triplicate are prepared from the working dilution of the ExtrAvidin-Alkaline Phosphotase in glycine buffer: 1:5,000 $(10^0)>10^{-0.5}>10^{-1}>10^{-1.5}$ 0.5 μl of each dilution is added to triplicate wells and the resulting AP content in each well is 5.50 ng, 1.74 ng, 0.55 ng, 0.18 ng. 100 μl of pNNP reagent must then be added to each of the standard wells. The plate must be incubated at 37° C. for 4 h. A volume of 50 μl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

The studies described in this example tested activity in galectin 11 protein. However, one skilled in the art could easily modify the exemplified studies to test the activity of galectin 11 polynucleotides (e.g., gene therapy), agonists, and/or antagonists of galectin 11.

Example 50

Galectin 11 Regulates Cell Cycle and Inhibits Cancer Cell Proliferation

Carbohydrate Binding

The amino acid sequence of the C-terminal domain of galectin 11 strays significantly from the conenseus sequence for galectins, and most of the conserved residues in the region that contact carbohydrate found in other galectins are not present in galectin 11. Thus, the ability of galectin 11 to bind carbohydrate was tested. Lysate from HeLa cells transfected with galectin 11 α or β cDNA were mixed with lactosyl-Sepaharose 4B and the bound proteins were eluted with the SDS sample buffer. Both unbound fractions and eluted materials were analyzed by immunoblotting using antibodies specific for an internal peptide of galectin 11. Galectin 11 did not bind to lacosyl-Sepharose 4B, while in the same experiment, lactose binding was obtained for galectin-3, as expected.

Tissue Distribution of Galectin 11 mRNA

Northern blot analysis showed that galectin 11 mRNA was nearly undetectable in many tissues tested, in contrast to galectin-3 mRNA, which was detected in almost all tissues. The results were not due to the quality of the galectin 11 cDNA probe, as strong signals were observed in Northern blot of mRNA from cells transfected with galectin 11 cDNA, using the same probe. However, using a more sensitive procedure, RT-PCR, galectin 11 mRNA was detectable in heart, spleen, thymus and peripheral blood leukocytes. It was also present at lower levels in lung, skeletal muscle, kidney, pancreas, prostate, testis, ovary and colon but virtually undetectable in brain and liver. Galectin 11 mRNA was not detected in many cell lines tested, but its expression was confirmed by RT-PCR in peripheral blood monocytes and polynucleated cells as well as myeloid cell lines, U937, HL-60 and KU-812, the B-cell line Wil-2, and breast cancer cell line HBL-100. Immunoblot analysis with the anti-peptide antibodies, however, failed to detect galectin 11 protein in these cell lines, although the procedures detected the protein in lysates from galectin 11 transfectants.

Induction of Galectin 11 Expression by Stress Signals

Since a galectin 11 clone was isolated from a Jurkat cell library arrested at G1, it was of interest to evaluate the expression of the message under these conditions, and other conditions that induce cell stasis. HeLa-S3 and Jurkat cells were treated with thymidine to synchronize cells at the G1-S border or theophylline and dibutyryl-cAMP for synchronizaion of cells at G1. Both treatments induced galectin 11 expression. AU-rich elements in galectin 11 mRNA and its restricted expression pattern suggest that galectin 11 gene product is inducible. Indeed, when HL-60 cells were treated with PMA plus ionomycin, galectin 11 mRNA was rapidly induced within 0.5 hr, but the message quickly diminished 2 hr after the treatment and was no longer detectable 4 hr later.

Cell Cycle Arrest by Ectopic Expression of Galectin 11

The fact that the galectin 11 was isolated from a cDNA library derived from a Jurkat cell line arrested at the G1 phase suggested that this protein may function in regulation of cell cycle. To test this possibility, a human cervical cancer cell line HeLa were cotransfected with vectors containing the complete cDNA for galectin 11 (both alpha and beta) and a plasmid containing green fluorescent protein (GFP) cDNA.

Compared with control vector-transfected HeLa cells, significantly higher percentage of cells expressing HA-tagged galectin 11 was found at the G1 phase of cell cycle, and compensatory lower percentages at the S and G2/M phases (data not shown). Similar results were obtained with a breast cancer cell line, MCF-7 (data not shown). The effects of the alpha and beta forms of galectin 11 were comparable.

Another member of the galectin family, galectin-9, which also contains two CRD, was studied for comparison. A hemagglutinin (HA)-tagged galectin-9 was used and galectin 11α so that their expression levels in transfected cells could be compared by immunoblotting using anti-HA antibodies. Galectin-9 levels were much higher than galectin 11 levels in the respective transfectants, even though an identical recipient cell line and procedure were used. Significantly, while galectin-9 expression did not have any notable effect on the cell cycle, galectin 11 induced G1 arrest in a dose-dependent manner.

To confirm the above findings, a transfection system based on adenovirus was employed, which is known to have a very high transfection efficiency in a variety of cell types. Thus, replication-defective adenoviruses containing galectin 11 were used to infect Arpe-19 cells. Initial experiments confirmed that close to 100% of the cells were infected, on the basis of expression of GFP, as measured by flow cytometry. A significantly higher percentage of cells tranfected with galectin 11 was in the G1 phase, compared with control transfectants. To demonstrate that the accumulation of cells at G1 was a result of G1 arrest rather than accelerated M to G1 transition, experiments were conducted in which nocodazole, a drug known to destroy spindle fibers and thus prevent he cells from exiting mitosis, was added to the cells after transfection. Forty-eight hr after the treatment, most cells infected with the control virus have exited G1 and were blocked at mitosis, while a significant portion of cells infected with viruses expressing either the α or β isoforms of galectin 11 remained at G1.

Inhibition of Cancer Cell Growth by Ectopic Expression of Galectin 11

Cell cycle arrest activity of galectin 11 indicated that cells transfected with galectin 11 would fail to proliferate. A colony formation assay was performed to formally demonstrate the suppression of cell growth resulting from the ectopic expression of galectin 11. HeLa cells were co-transfected with galectin 11 cDNA together with a construct for puromycin-resistance gene. While the control transfectants formed numerous colonies, galectin 11 transfectants formed only a few colonies, two weeks after selection in a puromycin-containing medium. The effect of galectin 11 expression on suppression of cell growth was measured more quantitatively by using a colorimertric assay. Significantly lower numbers of cells were obtained fromgalectin 11 transfectants as compared to control transfectants.

The present invention is not to be limited in scope by the specific embodiments described herein, which are intended as single illustrations of individual aspects of the invention. Indeed, various modifications of the invention, in addition to those shown and described herein will become apparent to those skilled in the art from the foregoing description and accompanying drawings. Such modifications are intended to fall within the scope of the appended claims.

The entire disclosure of all publications (including patents, patent applications, journal articles, laboratory manuals, books, or other documents) cited herein are hereby incorporated by reference.

Further, the Sequence Listing submitted herewith in paper and computer readable form is herein incorporated by reference in its entirely.

What is claimed is:

1. An isolated antibody or fragment thereof that specifically binds to a protein selected from the group consisting of:
   (a) a protein whose amino acid sequence consists of amino acid residues 1 to 133 of SEQ ID NO:2;
   (b) a protein whose amino acid sequence consists of a portion of SEQ ID NO:2, wherein said portion is at least 30 contiguous amino acid residues in length; and
   (c) a protein whose amino acid sequence consists of a portion of SEQ ID NO:2, wherein said portion is at least 50 contiguous amino acid residues in length.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 2 that specifically binds protein (b).

6. The antibody or fragment thereof of claim 2 wherein said protein bound by said antibody or fragment thereof is glycosylated.

7. The antibody or fragment thereof of claim 2 wherein said antibody is a human antibody.

8. The antibody or fragment thereof of claim 2 wherein said antibody is a polyclonal antibody.

9. The antibody or fragment thereof of claim 2 which is selected from the group consisting of:
   (a) a chimeric antibody or fragment thereof;
   (b) a humanized antibody or fragment thereof; and
   (c) a Fab fragment.

10. A labeled antibody or fragment thereof, wherein the antibody or fragment thereof of claim 2 is labeled.

11. An isolated cell that produces the antibody or fragment thereof of claim 2.

12. A hybridoma that produces the antibody of claim 2.

13. An isolated monoclonal antibody or fragment thereof that specifically binds to a protein selected from the group consisting of:
   (a) a protein whose amino acid sequence consists of amino acid residues 1 to 133 of SEQ ID NO:2;
   (b) a protein whose amino acid sequence consists of a portion of SEQ ID NO:2, wherein said portion is at least 30 contiguous amino acid residues in length; and
   (c) a protein whose amino acid sequence consists of a portion of SEQ ID NO:2, wherein said portion is at least 50 contiguous amino acid residues in length.

14. The antibody or fragment thereof of claim 13 that specifically binds protein (a).

15. The antibody or fragment thereof of claim 13 that specifically binds protein (b).

16. The antibody or fragment thereof of claim 13 that specifically binds protein (c).

17. The antibody or fragment thereof of claim 14 wherein said protein bound by said antibody or fragment thereof is glycosylated.

18. The antibody or fragment thereof of claim 14 wherein said antibody is a human antibody.

19. The antibody or fragment thereof of claim 14 which is selected from the group consisting of:
   (a) a chimeric antibody or fragment thereof;
   (b) a humanized antibody or fragment thereof; and
   (c) a Fab fragment.

20. A labeled antibody or fragment thereof, wherein the antibody or fragment thereof of claim 14 is labeled.

21. An isolated cell that produces the antibody or fragment thereof of claim 14.

22. A hybridoma that produces the antibody of claim 14.

23. An isolated antibody or fragment thereof that specifically binds to a protein selected from the group consisting of:
  (a) a protein whose amino acid sequence consists of the amino acid sequence of the Galectin-11 polypeptide encoded by the Galectin-11 cDNA contained in ATCC Deposit Number 209053;
  (b) a protein whose amino acid sequence consists of the amino acid sequence of a portion of the polypeptide encoded by the cDNA contained in ATCC Deposit Number 209053, wherein said portion is at least 30 contiguous amino acid residues in length; and
  (c) a protein whose amino acid sequence consists of the amino acid sequence of a portion of the polypeptide encoded by the cDNA contained in ATCC Deposit Number 209053, wherein said portion is at least 50 contiguous amino acid residues in length.

24. The antibody or fragment thereof of claim 23 that specifically binds protein (a).

25. The antibody or fragment thereof of claim 23 that specifically binds protein (b).

26. The antibody or fragment thereof of claim 23 that specifically binds protein (c).

27. The antibody or fragment thereof of claim 24 that specifically binds protein (b).

28. The antibody or fragment thereof of claim 24 wherein said protein bound by said antibody or fragment thereof is glycosylated.

29. The antibody or fragment thereof of claim 24 wherein said antibody is a human antibody.

30. The antibody or fragment thereof of claim 24 wherein said antibody is a polyclonal antibody.

31. The antibody or fragment thereof of claim 24 which is selected from the group consisting of:
  (a) a chimeric antibody or fragment thereof;
  (h) a humanized antibody or fragment thereof; and
  (c) a Fab fragment.

32. A labeled antibody or fragment thereof, wherein the antibody or fragment thereof of claim 24 is labeled.

33. An isolated cell that produces the antibody or fragment thereof of claim 24.

34. A hybridoma that produces the antibody of claim 24.

35. An isolated monoclonal antibody or fragment thereof that specifically binds to a protein selected from the group consisting of:
  (a) a protein whose amino acid sequence consists of the amino acid sequence of the Galectin-11 polypeptide encoded by the Galectin-11 cDNA contained in ATCC Deposit Number 209053;
  (b) a protein whose amino acid sequence consists of the amino acid sequence of a portion of the polypeptide encoded by the cDNA contained in ATCC Deposit Number 209053, wherein said portion is at least 30 contiguous amino acid residues in length; and
  (c) a protein whose amino acid sequence consists of the amino acid sequence of a portion of the polypeptide encoded by the cDNA contained in ATCC Deposit Number 209053, wherein said portion is at least 50 contiguous amino acid residues in length.

36. The antibody or fragment thereof of claim 35 that specifically binds protein (a).

37. The antibody or fragment thereof of claim 35 that specifically binds protein (b).

38. The antibody or fragment thereof of claim 35 that specifically binds protein (c).

39. The antibody or fragment thereof of claim 36 wherein said protein bound by said antibody or fragment thereof is glycosylated.

40. The antibody or fragment thereof of claim 36 wherein said antibody is a human antibody.

41. The antibody or fragment thereof of claim 36 which is selected from the group consisting of:
  (a) a chimeric antibody or fragment thereof;
  (b) a humanized antibody or fragment thereof; and
  (c) a Fab fragment.

42. A labeled antibody or fragment thereof, wherein the antibody or fragment thereof of claim 36 is labeled.

43. An isolated cell that produces the antibody or fragment thereof of claim 36.

44. A hybridoma that produces the antibody claim 36.

45. An isolated antibody or fragment thereof that specifically binds a Galectin-11 protein purified from a cell culture wherein said Galectin-11 protein is encoded by a polynucleotide encoding amino acids 1 to 133 of SEQ ID NO:2.

46. The antibody or fragment thereof of claim 45 wherein said antibody or fragment thereof is a monoclonal antibody.

47. The antibody or fragment thereof of claim 45 wherein said antibody is a polyclonal antibody.

48. The antibody or fragment thereof of claim 45 wherein said antibody is a human antibody.

49. The antibody or fragment thereof of claim 45 which is selected from the group consisting of:
  (a) a chimeric antibody or fragment thereof;
  (b) a humanized antibody or fragment thereof; and
  (d) a Fab fragment.

* * * * *